(12) United States Patent
Trusty et al.

(10) Patent No.: US 8,353,487 B2
(45) Date of Patent: Jan. 15, 2013

(54) USER INTERFACE SUPPORT DEVICES FOR ENDOSCOPIC SURGICAL INSTRUMENTS

(75) Inventors: Robert M. Trusty, Cincinnati, OH (US); Omar J. Vakharia, Cincinnati, OH (US); Gregory J. Bakos, Mason, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 371 days.

(21) Appl. No.: 12/640,469

(22) Filed: Dec. 17, 2009

(65) Prior Publication Data

US 2011/0152609 A1   Jun. 23, 2011

(51) Int. Cl.
*F16L 3/00* (2006.01)
(52) U.S. Cl. .................. 248/121; 248/74.1; 248/125.8
(58) Field of Classification Search .................. 600/102; 606/130; 248/121, 125.8, 75, 80, 81, 49, 248/73, 74.1, 68.1, 278.1
See application file for complete search history.

(56) References Cited

U.S. PATENT DOCUMENTS

| | | |
|---|---|---|
| 645,576 A | 3/1900 | Telsa |
| 649,621 A | 5/1900 | Tesla |
| 787,412 A | 4/1905 | Tesla |
| 1,127,948 A | 2/1915 | Wappler |
| 1,482,653 A | 2/1924 | Lilly |
| 1,625,602 A | 4/1927 | Gould et al. |
| 1,916,722 A | 7/1933 | Ende |
| 2,028,635 A | 1/1936 | Wappler |
| 2,031,682 A | 2/1936 | Wappler et al. |
| 2,113,246 A | 4/1938 | Wappler |
| 2,155,365 A | 4/1939 | Rankin |
| 2,191,858 A | 2/1940 | Moore |
| 2,196,620 A | 4/1940 | Attarian |
| 2,388,137 A | 10/1945 | Graumlich |
| 2,493,108 A | 1/1950 | Casey, Jr. |
| 2,504,152 A | 4/1950 | Riker et al. |
| 2,938,382 A | 5/1960 | De Graaf |
| 2,952,206 A | 9/1960 | Becksted |
| 3,069,195 A | 12/1962 | Buck |
| 3,070,088 A | 12/1962 | Brahos |
| 3,170,471 A | 2/1965 | Schnitzer |
| 3,435,824 A | 4/1969 | Gamponia |
| 3,470,876 A | 10/1969 | Barchilon |
| 3,595,239 A | 7/1971 | Petersen |
| 3,669,487 A | 6/1972 | Roberts et al. |
| 3,746,881 A | 7/1973 | Fitch et al. |

(Continued)

FOREIGN PATENT DOCUMENTS

AU    666310 B2    2/1996

(Continued)

OTHER PUBLICATIONS

Michael S. Kavic, M.D., "Natural Orifice Translumenal Endoscopic Surgery: "Notes"", JSLS, vol. 10, pp. 133-134 (2006).

(Continued)

*Primary Examiner* — Ramon Ramirez

(57) ABSTRACT

An interface system for interfacing between at least one endoscopic surgical instrument and a cable-controlled guide tube system. Various embodiments may include a tool docking assembly that is supportable relative to the cable-controlled guide system. The tool docking assembly may comprise one or more tool docking stations for retainingly supporting at least one endoscopic surgical instrument for selective pivotal travel about transverse axes. The system may further include cable attachment arrangements for coupling steering cables from the guide tube assembly to the various tool docking stations.

38 Claims, 42 Drawing Sheets

U.S. PATENT DOCUMENTS

| | | |
|---|---|---|
| 3,799,672 A | 3/1974 | Vurek |
| 3,854,473 A | 12/1974 | Matsuo |
| 3,946,740 A | 3/1976 | Bassett |
| 3,948,251 A | 4/1976 | Hosono |
| 3,994,301 A | 11/1976 | Agris |
| 4,011,872 A | 3/1977 | Komiya |
| 4,012,812 A | 3/1977 | Black |
| 4,085,743 A | 4/1978 | Yoon |
| 4,164,225 A | 8/1979 | Johnson et al. |
| 4,174,715 A | 11/1979 | Hasson |
| 4,178,920 A | 12/1979 | Cawood, Jr. et al. |
| 4,207,873 A | 6/1980 | Kruy |
| 4,235,238 A | 11/1980 | Ogiu et al. |
| 4,258,716 A | 3/1981 | Sutherland |
| 4,269,174 A | 5/1981 | Adair |
| 4,278,077 A | 7/1981 | Mizumoto |
| 4,285,344 A | 8/1981 | Marshall |
| 4,311,143 A | 1/1982 | Komiya |
| 4,329,980 A | 5/1982 | Terada |
| 4,396,021 A | 8/1983 | Baumgartner |
| 4,406,656 A | 9/1983 | Hattler et al. |
| 4,452,246 A | 6/1984 | Bader et al. |
| 4,461,281 A | 7/1984 | Carson |
| 4,491,132 A | 1/1985 | Aikins |
| 4,527,331 A | 7/1985 | Lasner et al. |
| 4,527,564 A | 7/1985 | Eguchi et al. |
| 4,538,594 A | 9/1985 | Boebel et al. |
| D281,104 S | 10/1985 | Davison |
| 4,569,347 A | 2/1986 | Frisbie |
| 4,580,551 A | 4/1986 | Siegmund et al. |
| 4,646,722 A | 3/1987 | Silverstein et al. |
| 4,653,476 A | 3/1987 | Bonnet |
| 4,655,219 A | 4/1987 | Petruzzi |
| 4,669,470 A | 6/1987 | Brandfield |
| 4,671,477 A | 6/1987 | Cullen |
| 4,685,447 A | 8/1987 | Iversen et al. |
| 4,711,240 A | 12/1987 | Goldwasser et al. |
| 4,712,545 A | 12/1987 | Honkanen |
| 4,721,116 A | 1/1988 | Schintgen et al. |
| 4,733,662 A | 3/1988 | DeSatnick et al. |
| D295,894 S | 5/1988 | Sharkany et al. |
| 4,763,669 A | 8/1988 | Jaeger |
| 4,770,188 A | 9/1988 | Chikama |
| 4,815,450 A | 3/1989 | Patel |
| 4,823,794 A | 4/1989 | Pierce |
| 4,829,999 A | 5/1989 | Auth |
| 4,867,140 A | 9/1989 | Hovis et al. |
| 4,869,238 A | 9/1989 | Opie et al. |
| 4,869,459 A | 9/1989 | Bourne |
| 4,873,979 A | 10/1989 | Hanna |
| 4,880,015 A | 11/1989 | Nierman |
| 4,911,148 A | 3/1990 | Sosnowski et al. |
| 4,926,860 A | 5/1990 | Stice et al. |
| 4,938,214 A | 7/1990 | Specht et al. |
| 4,950,273 A | 8/1990 | Briggs |
| 4,950,285 A | 8/1990 | Wilk |
| 4,960,133 A | 10/1990 | Hewson |
| 4,977,887 A | 12/1990 | Gouda |
| 4,979,950 A | 12/1990 | Transue et al. |
| 4,984,581 A | 1/1991 | Stice |
| 4,994,079 A | 2/1991 | Genese et al. |
| 5,007,917 A | 4/1991 | Evans |
| 5,010,876 A | 4/1991 | Henley et al. |
| 5,020,514 A | 6/1991 | Heckele |
| 5,020,535 A | 6/1991 | Parker et al. |
| 5,025,778 A | 6/1991 | Silverstein et al. |
| 5,033,169 A | 7/1991 | Bindon |
| 5,037,433 A | 8/1991 | Wilk et al. |
| 5,041,129 A | 8/1991 | Hayhurst et al. |
| 5,046,513 A | 9/1991 | Gatturna et al. |
| 5,050,585 A | 9/1991 | Takahashi |
| 5,052,372 A | 10/1991 | Shapiro |
| 5,065,516 A | 11/1991 | Dulebohn |
| 5,066,295 A | 11/1991 | Kozak et al. |
| 5,123,913 A | 6/1992 | Wilk et al. |
| 5,123,914 A | 6/1992 | Cope |
| 5,133,727 A | 7/1992 | Bales et al. |
| 5,147,374 A | 9/1992 | Fernandez |
| 5,174,300 A | 12/1992 | Bales et al. |
| 5,176,126 A | 1/1993 | Chikama |
| 5,190,050 A | 3/1993 | Nitzsche |
| 5,190,555 A | 3/1993 | Wetter et al. |
| 5,192,284 A | 3/1993 | Pleatman |
| 5,201,752 A | 4/1993 | Brown et al. |
| 5,201,908 A | 4/1993 | Jones |
| 5,203,785 A | 4/1993 | Slater |
| 5,203,787 A | 4/1993 | Noblitt et al. |
| 5,209,747 A | 5/1993 | Knoepfler |
| 5,217,003 A | 6/1993 | Wilk |
| 5,217,453 A | 6/1993 | Wilk |
| 5,219,357 A | 6/1993 | Honkanen et al. |
| 5,219,358 A | 6/1993 | Bendel et al. |
| 5,222,362 A | 6/1993 | Maus et al. |
| 5,222,965 A | 6/1993 | Haughton |
| 5,234,437 A | 8/1993 | Sepetka |
| 5,234,453 A | 8/1993 | Smith et al. |
| 5,235,964 A | 8/1993 | Abenaim |
| 5,242,456 A | 9/1993 | Nash et al. |
| 5,246,424 A | 9/1993 | Wilk |
| 5,259,366 A | 11/1993 | Reydel et al. |
| 5,263,958 A | 11/1993 | deGuillebon et al. |
| 5,273,524 A | 12/1993 | Fox et al. |
| 5,275,607 A | 1/1994 | Lo et al. |
| 5,284,128 A | 2/1994 | Hart |
| 5,284,162 A | 2/1994 | Wilk |
| 5,287,845 A | 2/1994 | Faul et al. |
| 5,287,852 A | 2/1994 | Arkinstall |
| 5,290,299 A | 3/1994 | Fain et al. |
| 5,290,302 A | 3/1994 | Pericic |
| 5,295,977 A | 3/1994 | Cohen et al. |
| 5,297,536 A | 3/1994 | Wilk |
| 5,301,061 A | 4/1994 | Nakada et al. |
| 5,312,333 A | 5/1994 | Churinetz et al. |
| 5,312,351 A | 5/1994 | Gerrone |
| 5,312,416 A | 5/1994 | Spaeth et al. |
| 5,312,423 A | 5/1994 | Rosenbluth et al. |
| 5,318,589 A | 6/1994 | Lichtman |
| 5,320,636 A | 6/1994 | Slater |
| 5,324,261 A | 6/1994 | Amundson et al. |
| 5,325,845 A | 7/1994 | Adair |
| 5,330,471 A | 7/1994 | Eggers |
| 5,330,486 A | 7/1994 | Wilk |
| 5,330,488 A | 7/1994 | Goldrath |
| 5,330,496 A | 7/1994 | Alferness |
| 5,330,502 A | 7/1994 | Hassler et al. |
| 5,331,971 A | 7/1994 | Bales et al. |
| 5,334,198 A | 8/1994 | Hart et al. |
| 5,344,428 A | 9/1994 | Griffiths |
| 5,350,391 A | 9/1994 | Iacovelli |
| 5,352,184 A | 10/1994 | Goldberg et al. |
| 5,352,222 A | 10/1994 | Rydell |
| 5,354,302 A | 10/1994 | Ko |
| 5,354,311 A | 10/1994 | Kambin et al. |
| 5,356,381 A | 10/1994 | Ensminger et al. |
| 5,356,408 A | 10/1994 | Rydell |
| 5,364,408 A | 11/1994 | Gordon |
| 5,364,410 A | 11/1994 | Failla et al. |
| 5,366,466 A | 11/1994 | Christian et al. |
| 5,366,467 A | 11/1994 | Lynch et al. |
| 5,368,605 A | 11/1994 | Miller, Jr. |
| 5,370,647 A | 12/1994 | Graber et al. |
| 5,370,679 A | 12/1994 | Atlee, III |
| 5,374,273 A | 12/1994 | Nakao et al. |
| 5,374,275 A | 12/1994 | Bradley et al. |
| 5,374,277 A | 12/1994 | Hassler |
| 5,377,695 A | 1/1995 | An Haack |
| 5,383,877 A | 1/1995 | Clarke |
| 5,383,888 A | 1/1995 | Zvenyatsky et al. |
| 5,386,817 A | 2/1995 | Jones |
| 5,391,174 A | 2/1995 | Weston |
| 5,392,789 A | 2/1995 | Slater et al. |
| 5,395,386 A | 3/1995 | Slater |
| 5,401,248 A | 3/1995 | Bencini |
| 5,403,328 A | 4/1995 | Shallman |
| 5,403,342 A | 4/1995 | Tovey et al. |
| 5,403,348 A | 4/1995 | Bonutti |
| 5,405,073 A | 4/1995 | Porter |

| Patent No. | Date | Inventor |
|---|---|---|
| 5,405,359 A | 4/1995 | Pierce |
| 5,409,478 A | 4/1995 | Gerry et al. |
| 5,417,699 A | 5/1995 | Klein et al. |
| 5,423,821 A | 6/1995 | Pasque |
| 5,433,721 A | 7/1995 | Hooven et al. |
| 5,439,471 A | 8/1995 | Kerr |
| 5,439,478 A | 8/1995 | Palmer |
| 5,441,059 A | 8/1995 | Dannan |
| 5,441,499 A | 8/1995 | Fritzsch |
| 5,443,463 A | 8/1995 | Stern et al. |
| 5,445,638 A | 8/1995 | Rydell et al. |
| 5,449,021 A | 9/1995 | Chikama |
| 5,454,827 A | 10/1995 | Aust et al. |
| 5,456,667 A | 10/1995 | Ham et al. |
| 5,456,684 A | 10/1995 | Schmidt et al. |
| 5,458,131 A | 10/1995 | Wilk |
| 5,458,583 A | 10/1995 | McNeely et al. |
| 5,460,168 A | 10/1995 | Masubuchi et al. |
| 5,460,629 A | 10/1995 | Shlain et al. |
| 5,462,561 A | 10/1995 | Voda |
| 5,465,731 A | 11/1995 | Bell et al. |
| 5,467,763 A | 11/1995 | McMahon et al. |
| 5,468,250 A | 11/1995 | Paraschac et al. |
| 5,470,308 A | 11/1995 | Edwards et al. |
| 5,470,320 A | 11/1995 | Tiefenbrun et al. |
| 5,478,347 A | 12/1995 | Aranyi |
| 5,480,404 A | 1/1996 | Kammerer et al. |
| 5,482,054 A | 1/1996 | Slater et al. |
| 5,484,451 A | 1/1996 | Akopov et al. |
| 5,489,256 A | 2/1996 | Adair |
| 5,496,347 A | 3/1996 | Hashiguchi et al. |
| 5,499,990 A | 3/1996 | Schülken et al. |
| 5,499,992 A | 3/1996 | Meade et al. |
| 5,501,692 A | 3/1996 | Riza |
| 5,503,616 A | 4/1996 | Jones |
| 5,505,686 A | 4/1996 | Willis et al. |
| 5,507,755 A | 4/1996 | Gresl et al. |
| 5,511,564 A | 4/1996 | Wilk |
| 5,514,157 A | 5/1996 | Nicholas et al. |
| 5,522,829 A | 6/1996 | Michalos |
| 5,522,830 A | 6/1996 | Aranyi |
| 5,527,321 A | 6/1996 | Hinchliffe |
| 5,536,248 A | 7/1996 | Weaver et al. |
| 5,538,509 A | 7/1996 | Dunlap et al. |
| 5,540,648 A | 7/1996 | Yoon |
| 5,554,151 A | 9/1996 | Hinchliffe |
| 5,555,883 A | 9/1996 | Avitall |
| 5,558,133 A | 9/1996 | Bortoli et al. |
| 5,562,693 A | 10/1996 | Devlin et al. |
| 5,569,243 A | 10/1996 | Kortenbach et al. |
| 5,569,298 A | 10/1996 | Schnell |
| 5,573,540 A | 11/1996 | Yoon |
| 5,578,030 A | 11/1996 | Levin |
| 5,582,611 A | 12/1996 | Tsuruta et al. |
| 5,582,617 A | 12/1996 | Klieman et al. |
| 5,584,845 A | 12/1996 | Hart |
| 5,591,179 A | 1/1997 | Edelstein |
| 5,593,420 A | 1/1997 | Eubanks, Jr et al. |
| 5,595,562 A | 1/1997 | Grier |
| 5,597,378 A | 1/1997 | Jervis |
| 5,601,573 A | 2/1997 | Fogelberg et al. |
| 5,601,588 A | 2/1997 | Tonomura et al. |
| 5,604,531 A | 2/1997 | Iddan et al. |
| 5,607,389 A | 3/1997 | Edwards et al. |
| 5,607,406 A | 3/1997 | Hernandez et al. |
| 5,607,450 A | 3/1997 | Zvenyatsky et al. |
| 5,613,975 A | 3/1997 | Christy |
| 5,618,303 A | 4/1997 | Marlow et al. |
| 5,620,415 A | 4/1997 | Lucey et al. |
| 5,624,399 A | 4/1997 | Ackerman |
| 5,624,431 A | 4/1997 | Gerry et al. |
| 5,626,578 A | 5/1997 | Tihon |
| 5,628,732 A | 5/1997 | Antoon, Jr. et al. |
| 5,630,782 A | 5/1997 | Adair |
| 5,643,283 A | 7/1997 | Younker |
| 5,643,292 A | 7/1997 | Hart |
| 5,643,294 A | 7/1997 | Tovey et al. |
| 5,644,798 A | 7/1997 | Shah |
| 5,645,083 A | 7/1997 | Essig et al. |
| 5,645,565 A | 7/1997 | Rudd et al. |
| 5,649,372 A | 7/1997 | Souza |
| 5,653,677 A | 8/1997 | Okada et al. |
| 5,653,690 A | 8/1997 | Booth et al. |
| 5,653,722 A | 8/1997 | Kieturakis |
| 5,662,663 A | 9/1997 | Shallman |
| 5,669,875 A | 9/1997 | van Eerdenburg |
| 5,681,324 A | 10/1997 | Kammerer et al. |
| 5,681,330 A | 10/1997 | Hughett et al. |
| 5,685,820 A | 11/1997 | Riek et al. |
| 5,690,606 A | 11/1997 | Slotman |
| 5,690,656 A | 11/1997 | Cope et al. |
| 5,690,660 A | 11/1997 | Kauker et al. |
| 5,695,448 A | 12/1997 | Kimura et al. |
| 5,695,505 A | 12/1997 | Yoon |
| 5,695,511 A | 12/1997 | Cano et al. |
| 5,700,275 A | 12/1997 | Bell et al. |
| 5,702,438 A | 12/1997 | Avitall |
| 5,704,892 A | 1/1998 | Adair |
| 5,709,708 A | 1/1998 | Thal |
| 5,716,326 A | 2/1998 | Dannan |
| 5,730,740 A | 3/1998 | Wales et al. |
| 5,735,849 A | 4/1998 | Baden et al. |
| 5,741,234 A | 4/1998 | Aboul-Hosn |
| 5,741,278 A | 4/1998 | Stevens |
| 5,741,285 A | 4/1998 | McBrayer et al. |
| 5,741,429 A | 4/1998 | Donadio, III et al. |
| 5,746,759 A | 5/1998 | Meade et al. |
| 5,749,826 A | 5/1998 | Faulkner |
| 5,749,881 A | 5/1998 | Sackier et al. |
| 5,749,889 A | 5/1998 | Bacich et al. |
| 5,752,951 A | 5/1998 | Yanik |
| 5,755,731 A | 5/1998 | Grinberg |
| 5,766,167 A | 6/1998 | Eggers et al. |
| 5,766,170 A | 6/1998 | Eggers |
| 5,766,205 A | 6/1998 | Zvenyatsky et al. |
| 5,769,849 A | 6/1998 | Eggers |
| 5,779,701 A | 7/1998 | McBrayer et al. |
| 5,779,716 A | 7/1998 | Cano et al. |
| 5,779,727 A | 7/1998 | Orejola |
| 5,782,859 A | 7/1998 | Nicholas et al. |
| 5,782,861 A | 7/1998 | Cragg et al. |
| 5,782,866 A | 7/1998 | Wenstrom, Jr. |
| 5,791,022 A | 8/1998 | Bohman |
| 5,792,113 A | 8/1998 | Kramer et al. |
| 5,792,153 A | 8/1998 | Swain et al. |
| 5,792,165 A | 8/1998 | Klieman et al. |
| 5,797,835 A | 8/1998 | Green |
| 5,797,928 A | 8/1998 | Kogasaka |
| 5,797,939 A | 8/1998 | Yoon |
| 5,797,941 A | 8/1998 | Schulze et al. |
| 5,803,903 A | 9/1998 | Athas et al. |
| 5,808,665 A | 9/1998 | Green |
| 5,810,806 A | 9/1998 | Ritchart et al. |
| 5,810,849 A | 9/1998 | Kontos |
| 5,810,865 A | 9/1998 | Koscher et al. |
| 5,810,876 A | 9/1998 | Kelleher |
| 5,810,877 A | 9/1998 | Roth et al. |
| 5,813,976 A | 9/1998 | Filipi et al. |
| 5,814,058 A | 9/1998 | Carlson et al. |
| 5,817,061 A | 10/1998 | Goodwin et al. |
| 5,817,107 A | 10/1998 | Schaller |
| 5,817,119 A | 10/1998 | Klieman et al. |
| 5,819,736 A | 10/1998 | Avny et al. |
| 5,823,947 A | 10/1998 | Yoon et al. |
| 5,824,071 A | 10/1998 | Nelson et al. |
| 5,827,281 A | 10/1998 | Levin |
| 5,827,299 A | 10/1998 | Thomason et al. |
| 5,830,231 A | 11/1998 | Geiges, Jr. |
| 5,833,700 A | 11/1998 | Fogelberg et al. |
| 5,833,703 A | 11/1998 | Manushakian |
| 5,843,017 A | 12/1998 | Yoon |
| 5,843,121 A | 12/1998 | Yoon |
| 5,849,022 A | 12/1998 | Sakashita et al. |
| 5,853,374 A | 12/1998 | Hart et al. |
| 5,855,585 A | 1/1999 | Kontos |
| 5,860,913 A | 1/1999 | Yamaya et al. |
| 5,860,995 A | 1/1999 | Berkelaar |
| 5,868,762 A | 2/1999 | Cragg et al. |

| | | | | | | |
|---|---|---|---|---|---|---|
| 5,876,411 A | 3/1999 | Kontos | | 6,117,158 A | 9/2000 | Measamer et al. |
| 5,882,331 A | 3/1999 | Sasaki | | 6,139,555 A | 10/2000 | Hart et al. |
| 5,882,344 A | 3/1999 | Stouder, Jr. | | 6,141,037 A | 10/2000 | Upton et al. |
| 5,893,846 A | 4/1999 | Bales et al. | | 6,146,391 A | 11/2000 | Cigaina |
| 5,893,874 A | 4/1999 | Bourque et al. | | 6,148,222 A | 11/2000 | Ramsey, III |
| 5,893,875 A | 4/1999 | O'Connor et al. | | 6,149,653 A | 11/2000 | Deslauriers |
| 5,897,487 A | 4/1999 | Ouchi | | 6,149,662 A | 11/2000 | Pugliesi et al. |
| 5,899,919 A | 5/1999 | Eubanks, Jr. et al. | | 6,156,006 A | 12/2000 | Brosens et al. |
| 5,902,254 A | 5/1999 | Magram | | 6,159,200 A | 12/2000 | Verdura et al. |
| 5,904,702 A | 5/1999 | Ek et al. | | 6,165,184 A | 12/2000 | Verdura et al. |
| 5,908,420 A | 6/1999 | Parins et al. | | 6,168,570 B1 | 1/2001 | Ferrera |
| 5,908,429 A | 6/1999 | Yoon | | 6,168,605 B1 | 1/2001 | Measamer et al. |
| 5,911,737 A | 6/1999 | Lee et al. | | 6,170,130 B1 | 1/2001 | Hamilton et al. |
| 5,916,146 A | 6/1999 | Allotta et al. | | 6,179,776 B1 | 1/2001 | Adams et al. |
| 5,916,147 A | 6/1999 | Boury | | 6,179,837 B1 | 1/2001 | Hooven |
| 5,921,993 A | 7/1999 | Yoon | | 6,183,420 B1 | 2/2001 | Douk et al. |
| 5,921,997 A | 7/1999 | Fogelberg et al. | | 6,190,353 B1 | 2/2001 | Makower et al. |
| 5,922,008 A | 7/1999 | Gimpelson | | 6,190,384 B1 | 2/2001 | Ouchi |
| 5,925,052 A | 7/1999 | Simmons | | 6,190,399 B1 | 2/2001 | Palmer et al. |
| 5,928,255 A | 7/1999 | Meade et al. | | 6,203,533 B1 | 3/2001 | Ouchi |
| 5,928,266 A | 7/1999 | Kontos | | 6,206,872 B1 | 3/2001 | Lafond et al. |
| 5,936,536 A | 8/1999 | Morris | | 6,206,877 B1 | 3/2001 | Kese et al. |
| 5,944,718 A | 8/1999 | Austin et al. | | 6,206,904 B1 | 3/2001 | Ouchi |
| 5,951,547 A | 9/1999 | Gough et al. | | 6,214,007 B1 | 4/2001 | Anderson |
| 5,951,549 A | 9/1999 | Richardson et al. | | 6,228,096 B1 | 5/2001 | Marchand |
| 5,954,720 A | 9/1999 | Wilson et al. | | 6,234,958 B1 | 5/2001 | Snoke et al. |
| 5,954,731 A | 9/1999 | Yoon | | 6,245,079 B1 | 6/2001 | Nobles et al. |
| 5,957,936 A | 9/1999 | Yoon et al. | | 6,246,914 B1 | 6/2001 | de la Rama et al. |
| 5,957,943 A | 9/1999 | Vaitekunas | | 6,258,064 B1 | 7/2001 | Smith et al. |
| 5,957,953 A | 9/1999 | DiPoto et al. | | 6,261,242 B1 | 7/2001 | Roberts et al. |
| 5,964,782 A | 10/1999 | Lafontaine et al. | | 6,264,664 B1 | 7/2001 | Avellanet |
| 5,971,995 A | 10/1999 | Rousseau | | 6,270,497 B1 | 8/2001 | Sekino et al. |
| 5,972,002 A | 10/1999 | Bark et al. | | 6,270,505 B1 | 8/2001 | Yoshida et al. |
| 5,976,074 A | 11/1999 | Moriyama | | 6,277,136 B1 | 8/2001 | Bonutti |
| 5,976,075 A | 11/1999 | Beane et al. | | 6,283,963 B1 | 9/2001 | Regula |
| 5,976,130 A | 11/1999 | McBrayer et al. | | 6,293,909 B1 | 9/2001 | Chu et al. |
| 5,976,131 A | 11/1999 | Guglielmi et al. | | 6,293,952 B1 | 9/2001 | Brosens et al. |
| 5,980,539 A | 11/1999 | Kontos | | 6,296,630 B1 | 10/2001 | Altman et al. |
| 5,980,556 A | 11/1999 | Giordano et al. | | 6,314,963 B1 | 11/2001 | Vaska et al. |
| 5,984,938 A | 11/1999 | Yoon | | 6,322,578 B1 | 11/2001 | Houle et al. |
| 5,984,939 A | 11/1999 | Yoon | | 6,326,177 B1 | 12/2001 | Schoenbach et al. |
| 5,984,950 A | 11/1999 | Cragg et al. | | 6,328,730 B1 | 12/2001 | Harkrider, Jr. |
| 5,989,182 A | 11/1999 | Hori et al. | | 6,350,267 B1 | 2/2002 | Stefanchik |
| 5,993,447 A | 11/1999 | Blewett et al. | | 6,350,278 B1 | 2/2002 | Lenker et al. |
| 5,993,474 A | 11/1999 | Ouchi | | 6,352,503 B1 | 3/2002 | Matsui et al. |
| 5,997,555 A | 12/1999 | Kontos | | 6,352,543 B1 | 3/2002 | Cole |
| 6,001,120 A | 12/1999 | Levin | | 6,355,013 B1 | 3/2002 | van Muiden |
| 6,004,269 A | 12/1999 | Crowley et al. | | 6,355,035 B1 | 3/2002 | Manushakian |
| 6,004,330 A | 12/1999 | Middleman et al. | | 6,361,534 B1 | 3/2002 | Chen et al. |
| 6,007,566 A | 12/1999 | Wenstrom, Jr. | | 6,371,956 B1 | 4/2002 | Wilson et al. |
| 6,010,515 A | 1/2000 | Swain et al. | | 6,379,366 B1 | 4/2002 | Fleischman et al. |
| 6,012,494 A | 1/2000 | Balazs | | 6,383,195 B1 | 5/2002 | Richard |
| 6,017,356 A | 1/2000 | Frederick et al. | | 6,383,197 B1 | 5/2002 | Conlon et al. |
| 6,019,770 A | 2/2000 | Christoudias | | 6,387,671 B1 | 5/2002 | Rubinsky et al. |
| 6,024,708 A | 2/2000 | Bales et al. | | 6,391,029 B1 | 5/2002 | Hooven et al. |
| 6,024,747 A | 2/2000 | Kontos | | 6,398,708 B1 | 6/2002 | Hastings et al. |
| 6,027,522 A | 2/2000 | Palmer | | 6,402,735 B1 | 6/2002 | Langevin |
| 6,030,365 A | 2/2000 | Laufer | | 6,406,440 B1 | 6/2002 | Stefanchik |
| 6,030,634 A | 2/2000 | Wu et al. | | 6,409,727 B1 | 6/2002 | Bales et al. |
| 6,033,399 A | 3/2000 | Gines | | 6,409,733 B1 | 6/2002 | Conlon et al. |
| 6,036,685 A | 3/2000 | Mueller | | 6,419,641 B1 | 7/2002 | Mark et al. |
| 6,053,927 A | 4/2000 | Hamas | | 6,427,089 B1 | 7/2002 | Knowlton |
| 6,066,160 A | 5/2000 | Colvin et al. | | 6,431,500 B1 | 8/2002 | Jacobs et al. |
| 6,068,603 A | 5/2000 | Suzuki | | 6,436,107 B1 | 8/2002 | Wang et al. |
| 6,068,629 A | 5/2000 | Haissaguerre et al. | | 6,443,970 B1 | 9/2002 | Schulze et al. |
| 6,071,233 A | 6/2000 | Ishikawa et al. | | 6,443,988 B2 | 9/2002 | Felt et al. |
| 6,074,408 A | 6/2000 | Freeman | | 6,447,511 B1 | 9/2002 | Slater |
| 6,086,530 A | 7/2000 | Mack | | 6,447,523 B1 | 9/2002 | Middleman et al. |
| 6,090,105 A | 7/2000 | Zepeda et al. | | 6,454,783 B1 | 9/2002 | Piskun |
| 6,090,108 A | 7/2000 | McBrayer et al. | | 6,454,785 B2 | 9/2002 | De Hoyos Garza |
| 6,090,129 A | 7/2000 | Ouchi | | 6,458,076 B1 | 10/2002 | Pruitt |
| 6,096,046 A | 8/2000 | Weiss | | 6,464,701 B1 | 10/2002 | Hooven et al. |
| 6,102,926 A | 8/2000 | Tartaglia et al. | | 6,464,702 B2 | 10/2002 | Schulze et al. |
| 6,106,473 A | 8/2000 | Violante et al. | | 6,470,218 B1 | 10/2002 | Behl |
| 6,109,852 A | 8/2000 | Shahinpoor et al. | | 6,475,104 B1 | 11/2002 | Lutz et al. |
| 6,110,154 A | 8/2000 | Shimomura et al. | | 6,485,411 B1 | 11/2002 | Konstorum et al. |
| 6,110,183 A | 8/2000 | Cope | | 6,489,745 B1 | 12/2002 | Koreis |
| 6,113,593 A | 9/2000 | Tu et al. | | 6,491,626 B1 | 12/2002 | Stone et al. |
| 6,117,144 A | 9/2000 | Nobles et al. | | 6,491,627 B1 | 12/2002 | Komi |

| | | |
|---|---|---|
| 6,491,691 B1 | 12/2002 | Morley et al. |
| 6,493,590 B1 | 12/2002 | Wessman et al. |
| 6,494,893 B2 | 12/2002 | Dubrul et al. |
| 6,500,176 B1 | 12/2002 | Truckai et al. |
| 6,503,192 B1 | 1/2003 | Ouchi |
| 6,506,190 B1 | 1/2003 | Walshe |
| 6,508,827 B1 | 1/2003 | Manhes |
| 6,514,239 B2 * | 2/2003 | Shimmura et al. ............ 606/1 |
| 6,520,954 B2 | 2/2003 | Ouchi |
| 6,527,782 B2 | 3/2003 | Hogg et al. |
| 6,543,456 B1 | 4/2003 | Freeman |
| 6,551,270 B1 | 4/2003 | Bimbo et al. |
| 6,554,766 B2 | 4/2003 | Maeda et al. |
| 6,554,829 B2 | 4/2003 | Schulze et al. |
| 6,558,384 B2 | 5/2003 | Mayenberger |
| 6,562,035 B1 | 5/2003 | Levin |
| 6,562,052 B2 | 5/2003 | Nobles et al. |
| 6,569,159 B1 | 5/2003 | Edwards et al. |
| 6,572,629 B2 | 6/2003 | Kalloo et al. |
| 6,572,635 B1 | 6/2003 | Bonutti |
| 6,575,988 B2 | 6/2003 | Rousseau |
| 6,579,311 B1 | 6/2003 | Makower |
| 6,581,889 B2 | 6/2003 | Carpenter et al. |
| 6,585,642 B2 | 7/2003 | Christopher |
| 6,585,717 B1 | 7/2003 | Wittenberger et al. |
| 6,587,750 B2 * | 7/2003 | Gerbi et al. ............ 700/245 |
| 6,592,559 B1 | 7/2003 | Pakter et al. |
| 6,592,603 B2 | 7/2003 | Lasner |
| 6,602,262 B2 | 8/2003 | Griego et al. |
| 6,605,105 B1 | 8/2003 | Cuschieri et al. |
| 6,610,072 B1 | 8/2003 | Christy et al. |
| 6,610,074 B2 | 8/2003 | Santilli |
| 6,620,193 B1 | 9/2003 | Lau et al. |
| 6,623,448 B2 | 9/2003 | Slater |
| 6,626,919 B1 | 9/2003 | Swanstrom |
| 6,632,229 B1 | 10/2003 | Yamanouchi |
| 6,638,286 B1 | 10/2003 | Burbank et al. |
| 6,645,225 B1 | 11/2003 | Atkinson |
| 6,652,521 B2 | 11/2003 | Schulze |
| 6,652,551 B1 | 11/2003 | Heiss |
| 6,656,194 B1 | 12/2003 | Gannoe et al. |
| 6,663,641 B1 | 12/2003 | Kovac et al. |
| 6,663,655 B2 | 12/2003 | Ginn et al. |
| 6,666,854 B1 | 12/2003 | Lange |
| 6,672,338 B1 | 1/2004 | Esashi et al. |
| 6,673,058 B2 | 1/2004 | Snow |
| 6,673,087 B1 | 1/2004 | Chang et al. |
| 6,679,882 B1 | 1/2004 | Kornerup |
| 6,685,628 B2 | 2/2004 | Vu |
| 6,685,724 B1 | 2/2004 | Haluck |
| 6,692,445 B2 | 2/2004 | Roberts et al. |
| 6,692,462 B2 | 2/2004 | Mackenzie et al. |
| 6,699,180 B2 | 3/2004 | Kobayashi |
| 6,699,256 B1 | 3/2004 | Logan et al. |
| 6,699,263 B2 | 3/2004 | Cope |
| 6,706,018 B2 | 3/2004 | Westlund et al. |
| 6,708,066 B2 | 3/2004 | Herbst et al. |
| 6,709,445 B2 | 3/2004 | Boebel et al. |
| 6,716,226 B2 | 4/2004 | Sixto, Jr. et al. |
| 6,736,822 B2 | 5/2004 | McClellan et al. |
| 6,740,030 B2 | 5/2004 | Martone et al. |
| 6,743,166 B2 | 6/2004 | Berci et al. |
| 6,743,239 B1 | 6/2004 | Kuehn et al. |
| 6,743,240 B2 | 6/2004 | Smith et al. |
| 6,749,560 B1 | 6/2004 | Konstorum et al. |
| 6,749,609 B1 | 6/2004 | Lunsford et al. |
| 6,752,768 B2 | 6/2004 | Burdorff et al. |
| 6,752,811 B2 | 6/2004 | Chu et al. |
| 6,752,822 B2 | 6/2004 | Jespersen |
| 6,758,857 B2 | 7/2004 | Cioanta et al. |
| 6,761,685 B2 | 7/2004 | Adams et al. |
| 6,761,718 B2 | 7/2004 | Madsen |
| 6,761,722 B2 | 7/2004 | Cole et al. |
| 6,773,434 B2 | 8/2004 | Ciarrocca |
| 6,776,787 B2 | 8/2004 | Phung et al. |
| 6,780,151 B2 | 8/2004 | Grabover et al. |
| 6,780,352 B2 | 8/2004 | Jacobson |
| 6,783,491 B2 | 8/2004 | Saadat et al. |
| 6,786,864 B2 | 9/2004 | Matsuura et al. |
| 6,790,173 B2 | 9/2004 | Saadat et al. |
| 6,790,217 B2 | 9/2004 | Schulze et al. |
| 6,795,728 B2 | 9/2004 | Chornenky et al. |
| 6,800,056 B2 | 10/2004 | Tartaglia et al. |
| 6,808,491 B2 | 10/2004 | Kortenbach et al. |
| 6,817,974 B2 | 11/2004 | Cooper et al. |
| 6,824,548 B2 | 11/2004 | Smith et al. |
| 6,836,688 B2 | 12/2004 | Ingle et al. |
| 6,837,847 B2 | 1/2005 | Ewers et al. |
| 6,840,938 B1 | 1/2005 | Morley et al. |
| 6,843,794 B2 | 1/2005 | Sixto, Jr. et al. |
| 6,861,250 B1 | 3/2005 | Cole et al. |
| 6,866,627 B2 | 3/2005 | Nozue |
| 6,866,628 B2 | 3/2005 | Goodman et al. |
| 6,878,106 B1 | 4/2005 | Herrmann |
| 6,878,110 B2 | 4/2005 | Yang et al. |
| 6,881,216 B2 | 4/2005 | Di Caprio et al. |
| 6,884,213 B2 | 4/2005 | Raz et al. |
| 6,887,255 B2 | 5/2005 | Shimm |
| 6,889,089 B2 | 5/2005 | Behl et al. |
| 6,896,683 B1 | 5/2005 | Gadberry et al. |
| 6,896,692 B2 | 5/2005 | Ginn et al. |
| 6,908,427 B2 | 6/2005 | Fleener et al. |
| 6,908,476 B2 | 6/2005 | Jud et al. |
| 6,916,284 B2 | 7/2005 | Moriyama |
| 6,918,871 B2 | 7/2005 | Schulze |
| 6,918,908 B2 | 7/2005 | Bonner et al. |
| 6,926,725 B2 | 8/2005 | Cooke et al. |
| 6,932,810 B2 | 8/2005 | Ryan |
| 6,932,824 B1 | 8/2005 | Roop et al. |
| 6,932,827 B2 | 8/2005 | Cole |
| 6,932,834 B2 | 8/2005 | Lizardi et al. |
| 6,936,003 B2 | 8/2005 | Iddan |
| 6,939,327 B2 | 9/2005 | Hall et al. |
| 6,942,613 B2 | 9/2005 | Ewers et al. |
| 6,944,490 B1 | 9/2005 | Chow |
| 6,945,472 B2 | 9/2005 | Wuttke et al. |
| 6,945,979 B2 | 9/2005 | Kortenbach et al. |
| 6,955,683 B2 | 10/2005 | Bonutti |
| 6,958,035 B2 | 10/2005 | Friedman et al. |
| 6,960,162 B2 | 11/2005 | Saadat et al. |
| 6,960,163 B2 | 11/2005 | Ewers et al. |
| 6,962,587 B2 | 11/2005 | Johnson et al. |
| 6,964,662 B2 | 11/2005 | Kidooka |
| 6,966,909 B2 | 11/2005 | Marshall et al. |
| 6,966,919 B2 | 11/2005 | Sixto, Jr. et al. |
| 6,967,462 B1 | 11/2005 | Landis |
| 6,971,988 B2 | 12/2005 | Orban, III |
| 6,972,017 B2 | 12/2005 | Smith et al. |
| 6,974,411 B2 | 12/2005 | Belson |
| 6,976,992 B2 | 12/2005 | Sachatello et al. |
| 6,984,203 B2 | 1/2006 | Tartaglia et al. |
| 6,984,205 B2 | 1/2006 | Gazdzinski |
| 6,986,774 B2 | 1/2006 | Middleman et al. |
| 6,988,987 B2 | 1/2006 | Ishikawa et al. |
| 6,989,028 B2 | 1/2006 | Lashinski et al. |
| 6,991,627 B2 | 1/2006 | Madhani et al. |
| 6,991,631 B2 | 1/2006 | Woloszko et al. |
| 6,994,708 B2 | 2/2006 | Manzo |
| 6,997,931 B2 | 2/2006 | Sauer et al. |
| 7,000,818 B2 | 2/2006 | Shelton, IV et al. |
| 7,001,341 B2 | 2/2006 | Gellman et al. |
| 7,008,375 B2 | 3/2006 | Weisel |
| 7,009,634 B2 | 3/2006 | Iddan et al. |
| 7,010,340 B2 | 3/2006 | Scarantino et al. |
| 7,020,531 B1 | 3/2006 | Colliou et al. |
| 7,025,580 B2 | 4/2006 | Heagy et al. |
| 7,029,435 B2 | 4/2006 | Nakao |
| 7,029,438 B2 | 4/2006 | Morin et al. |
| 7,029,450 B2 | 4/2006 | Gellman |
| 7,032,600 B2 | 4/2006 | Fukuda et al. |
| 7,035,680 B2 | 4/2006 | Partridge et al. |
| 7,037,290 B2 | 5/2006 | Gardeski et al. |
| 7,041,052 B2 | 5/2006 | Saadat et al. |
| 7,052,489 B2 | 5/2006 | Griego et al. |
| 7,060,024 B2 | 6/2006 | Long et al. |
| 7,060,025 B2 | 6/2006 | Long et al. |
| 7,063,697 B2 | 6/2006 | Slater |
| 7,063,715 B2 | 6/2006 | Onuki et al. |

| | | |
|---|---|---|
| 7,066,879 B2 | 6/2006 | Fowler et al. |
| 7,066,936 B2 | 6/2006 | Ryan |
| 7,070,602 B2 | 7/2006 | Smith et al. |
| 7,076,305 B2 | 7/2006 | Imran et al. |
| 7,083,618 B2 | 8/2006 | Couture et al. |
| 7,083,620 B2 | 8/2006 | Jahns et al. |
| 7,083,629 B2 | 8/2006 | Weller et al. |
| 7,083,635 B2 | 8/2006 | Ginn |
| 7,087,071 B2 | 8/2006 | Nicholas et al. |
| 7,090,673 B2 | 8/2006 | Dycus et al. |
| 7,090,683 B2 | 8/2006 | Brock et al. |
| 7,090,685 B2 | 8/2006 | Kortenbach et al. |
| 7,093,518 B2 | 8/2006 | Gmeilbauer |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,105,000 B2 | 9/2006 | McBrayer |
| 7,105,005 B2 | 9/2006 | Blake |
| 7,108,696 B2 | 9/2006 | Daniel et al. |
| 7,108,703 B2 | 9/2006 | Danitz et al. |
| 7,112,208 B2 | 9/2006 | Morris et al. |
| 7,115,092 B2 | 10/2006 | Park et al. |
| 7,117,703 B2 | 10/2006 | Kato et al. |
| 7,118,531 B2 | 10/2006 | Krill |
| 7,118,578 B2 | 10/2006 | West, Jr. et al. |
| 7,118,587 B2 | 10/2006 | Dycus et al. |
| 7,128,708 B2 | 10/2006 | Saadat et al. |
| RE39,415 E | 11/2006 | Bales et al. |
| 7,131,978 B2 | 11/2006 | Sancoff et al. |
| 7,131,979 B2 | 11/2006 | DiCarlo et al. |
| 7,131,980 B1 | 11/2006 | Field et al. |
| 7,137,980 B2 | 11/2006 | Buysse et al. |
| 7,137,981 B2 | 11/2006 | Long |
| 7,146,984 B2 | 12/2006 | Stack et al. |
| 7,147,650 B2 | 12/2006 | Lee |
| 7,150,097 B2 | 12/2006 | Sremcich et al. |
| 7,150,655 B2 | 12/2006 | Mastrototaro et al. |
| 7,150,750 B2 | 12/2006 | Damarati |
| 7,153,321 B2 | 12/2006 | Andrews |
| 7,160,296 B2 | 1/2007 | Pearson et al. |
| 7,163,525 B2 | 1/2007 | Franer |
| 7,172,714 B2 | 2/2007 | Jacobson |
| 7,179,254 B2 | 2/2007 | Pendekanti et al. |
| 7,188,627 B2 | 3/2007 | Nelson et al. |
| 7,195,612 B2 | 3/2007 | van Sloten et al. |
| 7,195,631 B2 | 3/2007 | Dumbauld |
| 7,204,820 B2 | 4/2007 | Akahoshi |
| 7,208,005 B2 | 4/2007 | Frecker et al. |
| 7,211,092 B2 | 5/2007 | Hughett |
| 7,220,227 B2 | 5/2007 | Sasaki et al. |
| 7,223,272 B2 | 5/2007 | Francese et al. |
| 7,229,438 B2 | 6/2007 | Young |
| 7,232,414 B2 | 6/2007 | Gonzalez |
| 7,232,445 B2 | 6/2007 | Kortenbach et al. |
| 7,235,089 B1 | 6/2007 | McGuckin, Jr. |
| 7,241,290 B2 | 7/2007 | Doyle et al. |
| 7,244,228 B2 | 7/2007 | Lubowski |
| 7,250,027 B2 | 7/2007 | Barry |
| 7,252,660 B2 | 8/2007 | Kunz |
| 7,255,675 B2 | 8/2007 | Gertner et al. |
| 7,270,663 B2 | 9/2007 | Nakao |
| 7,294,139 B1 | 11/2007 | Gengler |
| 7,301,250 B2 | 11/2007 | Cassel |
| 7,306,597 B2 | 12/2007 | Manzo |
| 7,308,828 B2 | 12/2007 | Hashimoto |
| 7,318,802 B2 | 1/2008 | Suzuki et al. |
| 7,320,695 B2 | 1/2008 | Carroll |
| 7,322,934 B2 | 1/2008 | Miyake et al. |
| 7,323,006 B2 | 1/2008 | Andreas et al. |
| 7,329,256 B2 | 2/2008 | Johnson et al. |
| 7,329,257 B2 | 2/2008 | Kanehira et al. |
| 7,329,383 B2 | 2/2008 | Stinson |
| 7,344,536 B1 | 3/2008 | Lunsford et al. |
| 7,352,387 B2 | 4/2008 | Yamamoto |
| 7,364,582 B2 | 4/2008 | Lee |
| 7,371,215 B2 | 5/2008 | Colliou et al. |
| 7,381,216 B2 | 6/2008 | Buzzard et al. |
| 7,390,324 B2 | 6/2008 | Whalen et al. |
| 7,393,322 B2 | 7/2008 | Wenchell |
| 7,402,162 B2 | 7/2008 | Ouchi |
| 7,404,791 B2 | 7/2008 | Linares et al. |
| 7,410,483 B2 | 8/2008 | Danitz et al. |
| 7,413,563 B2 | 8/2008 | Corcoran et al. |
| 7,416,554 B2 | 8/2008 | Lam et al. |
| 7,422,590 B2 | 9/2008 | Kupferschmid et al. |
| 7,435,257 B2 | 10/2008 | Lashinski et al. |
| 7,452,327 B2 | 11/2008 | Durgin et al. |
| 7,455,208 B2 | 11/2008 | Wales et al. |
| 7,468,066 B2 | 12/2008 | Vargas et al. |
| 7,488,295 B2 | 2/2009 | Burbank et al. |
| 7,494,499 B2 | 2/2009 | Nagase et al. |
| 7,497,867 B2 | 3/2009 | Lasner et al. |
| 7,498,950 B1 | 3/2009 | Ertas et al. |
| 7,507,200 B2 | 3/2009 | Okada |
| 7,510,107 B2 | 3/2009 | Timm et al. |
| 7,511,733 B2 | 3/2009 | Takizawa et al. |
| 7,515,953 B2 | 4/2009 | Madar et al. |
| 7,520,876 B2 | 4/2009 | Ressemann et al. |
| 7,524,281 B2 | 4/2009 | Chu et al. |
| 7,524,302 B2 | 4/2009 | Tower |
| 7,534,228 B2 | 5/2009 | Williams |
| 7,540,872 B2 | 6/2009 | Schechter et al. |
| 7,544,203 B2 | 6/2009 | Chin et al. |
| 7,548,040 B2 | 6/2009 | Lee et al. |
| 7,549,564 B2 | 6/2009 | Boudreaux |
| 7,553,278 B2 | 6/2009 | Kucklick |
| 7,553,298 B2 | 6/2009 | Hunt et al. |
| 7,559,887 B2 | 7/2009 | Dannan |
| 7,559,916 B2 | 7/2009 | Smith et al. |
| 7,560,006 B2 | 7/2009 | Rakos et al. |
| 7,561,916 B2 | 7/2009 | Hunt et al. |
| 7,566,334 B2 | 7/2009 | Christian et al. |
| 7,575,144 B2 | 8/2009 | Ortiz et al. |
| 7,575,548 B2 | 8/2009 | Takemoto et al. |
| 7,579,550 B2 | 8/2009 | Dayton et al. |
| 7,582,096 B2 | 9/2009 | Gellman et al. |
| 7,588,177 B2 | 9/2009 | Racenet |
| 7,588,557 B2 | 9/2009 | Nakao |
| 7,597,229 B2 | 10/2009 | Boudreaux et al. |
| 7,604,150 B2 | 10/2009 | Boudreaux |
| 7,608,083 B2 | 10/2009 | Lee et al. |
| 7,618,398 B2 | 11/2009 | Holman et al. |
| 7,632,250 B2 | 12/2009 | Smith et al. |
| 7,635,373 B2 | 12/2009 | Ortiz |
| 7,637,903 B2 | 12/2009 | Lentz et al. |
| 7,650,742 B2 | 1/2010 | Ushijima |
| 7,651,483 B2 | 1/2010 | Byrum et al. |
| 7,654,431 B2 | 2/2010 | Hueil et al. |
| 7,655,004 B2 | 2/2010 | Long |
| 7,662,089 B2 | 2/2010 | Okada et al. |
| 7,666,180 B2 | 2/2010 | Holsten et al. |
| 7,666,203 B2 | 2/2010 | Chanduszko et al. |
| 7,674,259 B2 | 3/2010 | Shadduck |
| 7,678,043 B2 | 3/2010 | Gilad |
| 7,684,599 B2 | 3/2010 | Horn et al. |
| 7,697,970 B2 | 4/2010 | Uchiyama et al. |
| 7,699,835 B2 | 4/2010 | Lee et al. |
| 7,699,864 B2 | 4/2010 | Kick et al. |
| 7,713,189 B2 | 5/2010 | Hanke |
| 7,713,270 B2 | 5/2010 | Suzuki |
| 7,736,374 B2 | 6/2010 | Vaughan et al. |
| 7,744,615 B2 | 6/2010 | Couture |
| 7,753,933 B2 | 7/2010 | Ginn et al. |
| 7,758,577 B2 | 7/2010 | Nobis et al. |
| 7,762,949 B2 | 7/2010 | Nakao |
| 7,762,998 B2 | 7/2010 | Birk et al. |
| 7,763,012 B2 | 7/2010 | Petrick et al. |
| 7,771,416 B2 | 8/2010 | Spivey et al. |
| 7,780,683 B2 | 8/2010 | Roue et al. |
| 7,780,691 B2 | 8/2010 | Stefanchik |
| 7,784,663 B2 | 8/2010 | Shelton, IV |
| 7,794,409 B2 | 9/2010 | Damarati |
| 7,794,475 B2 | 9/2010 | Hess et al. |
| 7,798,386 B2 | 9/2010 | Schall et al. |
| 7,815,662 B2 | 10/2010 | Spivey et al. |
| 7,828,186 B2 | 11/2010 | Wales |
| 7,837,615 B2 | 11/2010 | Le et al. |
| 7,842,028 B2 | 11/2010 | Lee |

| | | |
|---|---|---|
| 7,842,068 B2 | 11/2010 | Ginn |
| 7,846,171 B2 | 12/2010 | Kullas et al. |
| 7,850,660 B2 | 12/2010 | Uth et al. |
| 7,857,183 B2 | 12/2010 | Shelton, IV |
| 7,862,546 B2 | 1/2011 | Conlon et al. |
| 7,867,216 B2 | 1/2011 | Wahr et al. |
| 7,892,220 B2 | 2/2011 | Faller et al. |
| 7,896,887 B2 | 3/2011 | Rimbaugh et al. |
| 7,905,828 B2 | 3/2011 | Brock et al. |
| 7,909,809 B2 | 3/2011 | Scopton et al. |
| 7,914,513 B2 | 3/2011 | Voorhees, Jr. |
| 7,918,869 B2 | 4/2011 | Saadat et al. |
| 7,931,624 B2 | 4/2011 | Smith et al. |
| 7,945,332 B2 | 5/2011 | Schechter |
| 7,947,000 B2 | 5/2011 | Vargas et al. |
| 7,955,298 B2 | 6/2011 | Carroll et al. |
| 7,963,975 B2 | 6/2011 | Criscuolo |
| 7,965,180 B2 | 6/2011 | Koyama |
| 7,967,808 B2 | 6/2011 | Fitzgerald et al. |
| 7,969,473 B2 | 6/2011 | Kotoda |
| 7,988,685 B2 | 8/2011 | Ziaie et al. |
| 8,048,067 B2 | 11/2011 | Davalos et al. |
| 8,057,510 B2 | 11/2011 | Ginn et al. |
| 8,066,632 B2 | 11/2011 | Dario et al. |
| 8,075,587 B2 | 12/2011 | Ginn |
| 8,088,062 B2 | 1/2012 | Zwolinski |
| 8,118,821 B2 | 2/2012 | Mouw |
| 8,147,424 B2 | 4/2012 | Kassab et al. |
| 2001/0023333 A1 | 9/2001 | Wise et al. |
| 2001/0049497 A1 | 12/2001 | Kalloo et al. |
| 2002/0022771 A1 | 2/2002 | Diokno et al. |
| 2002/0022857 A1 | 2/2002 | Goldsteen et al. |
| 2002/0023353 A1 | 2/2002 | Ting-Kung |
| 2002/0029055 A1 | 3/2002 | Bonutti |
| 2002/0042562 A1 | 4/2002 | Meron et al. |
| 2002/0049439 A1 | 4/2002 | Mulier et al. |
| 2002/0068945 A1 | 6/2002 | Sixto, Jr. et al. |
| 2002/0078967 A1 | 6/2002 | Sixto, Jr. et al. |
| 2002/0082516 A1 | 6/2002 | Stefanchik |
| 2002/0095164 A1 | 7/2002 | Andreas et al. |
| 2002/0107530 A1 | 8/2002 | Sauer et al. |
| 2002/0133115 A1 | 9/2002 | Gordon et al. |
| 2002/0138086 A1 | 9/2002 | Sixto, Jr. et al. |
| 2002/0147456 A1 | 10/2002 | Diduch et al. |
| 2002/0165592 A1 | 11/2002 | Glukhovsky et al. |
| 2002/0183591 A1 | 12/2002 | Matsuura et al. |
| 2003/0023255 A1 | 1/2003 | Miles et al. |
| 2003/0036679 A1 | 2/2003 | Kortenbach et al. |
| 2003/0069602 A1 | 4/2003 | Jacobs et al. |
| 2003/0083681 A1 | 5/2003 | Moutafis et al. |
| 2003/0114731 A1 | 6/2003 | Cadeddu et al. |
| 2003/0114732 A1 | 6/2003 | Webler et al. |
| 2003/0120257 A1 | 6/2003 | Houston et al. |
| 2003/0124009 A1 | 7/2003 | Ravi et al. |
| 2003/0130564 A1 | 7/2003 | Martone et al. |
| 2003/0130656 A1 | 7/2003 | Levin |
| 2003/0158521 A1 | 8/2003 | Ameri |
| 2003/0167062 A1 | 9/2003 | Gambale et al. |
| 2003/0171651 A1 | 9/2003 | Page et al. |
| 2003/0176880 A1 | 9/2003 | Long et al. |
| 2003/0216611 A1 | 11/2003 | Vu |
| 2003/0216615 A1 | 11/2003 | Ouchi |
| 2003/0220545 A1 | 11/2003 | Ouchi |
| 2003/0225312 A1 | 12/2003 | Suzuki et al. |
| 2003/0225332 A1 | 12/2003 | Okada et al. |
| 2003/0229269 A1 | 12/2003 | Humphrey |
| 2003/0229371 A1 | 12/2003 | Whitworth |
| 2003/0236549 A1 | 12/2003 | Bonadio et al. |
| 2004/0002683 A1 | 1/2004 | Nicholson et al. |
| 2004/0034369 A1 | 2/2004 | Sauer et al. |
| 2004/0054322 A1 | 3/2004 | Vargas |
| 2004/0098007 A1 | 5/2004 | Heiss |
| 2004/0101456 A1 | 5/2004 | Kuroshima et al. |
| 2004/0104999 A1 | 6/2004 | Okada |
| 2004/0116948 A1 | 6/2004 | Sixto, Jr. et al. |
| 2004/0127940 A1 | 7/2004 | Ginn et al. |
| 2004/0133077 A1 | 7/2004 | Obenchain et al. |
| 2004/0133089 A1 | 7/2004 | Kilcoyne et al. |
| 2004/0136779 A1 | 7/2004 | Bhaskar |
| 2004/0138525 A1 | 7/2004 | Saadat et al. |
| 2004/0138529 A1 | 7/2004 | Wiltshire et al. |
| 2004/0138587 A1 | 7/2004 | Lyons, IV |
| 2004/0161451 A1 | 8/2004 | Pierce et al. |
| 2004/0186350 A1 | 9/2004 | Brenneman et al. |
| 2004/0193009 A1 | 9/2004 | Jaffe et al. |
| 2004/0193146 A1 | 9/2004 | Lee et al. |
| 2004/0193186 A1 | 9/2004 | Kortenbach et al. |
| 2004/0193188 A1 | 9/2004 | Francese |
| 2004/0193189 A1 | 9/2004 | Kortenbach et al. |
| 2004/0193200 A1 | 9/2004 | Dworschak et al. |
| 2004/0199052 A1 | 10/2004 | Banik et al. |
| 2004/0199159 A1 | 10/2004 | Lee et al. |
| 2004/0206859 A1* | 10/2004 | Chong et al. ............. 248/121 |
| 2004/0210245 A1 | 10/2004 | Erickson et al. |
| 2004/0215058 A1 | 10/2004 | Zirps et al. |
| 2004/0225183 A1 | 11/2004 | Michlitsch et al. |
| 2004/0225186 A1 | 11/2004 | Horne, Jr. et al. |
| 2004/0230095 A1 | 11/2004 | Stefanchik et al. |
| 2004/0230096 A1 | 11/2004 | Stefanchik et al. |
| 2004/0230097 A1 | 11/2004 | Stefanchik et al. |
| 2004/0230161 A1 | 11/2004 | Zeiner |
| 2004/0244512 A1* | 12/2004 | Hedrich et al. ............ 73/866.5 |
| 2004/0249246 A1 | 12/2004 | Campos |
| 2004/0249367 A1 | 12/2004 | Saadat et al. |
| 2004/0249394 A1 | 12/2004 | Morris et al. |
| 2004/0249443 A1 | 12/2004 | Shanley et al. |
| 2004/0254572 A1 | 12/2004 | McIntyre et al. |
| 2005/0004515 A1 | 1/2005 | Hart et al. |
| 2005/0033265 A1 | 2/2005 | Engel et al. |
| 2005/0033277 A1 | 2/2005 | Clague et al. |
| 2005/0033319 A1 | 2/2005 | Gambale et al. |
| 2005/0033333 A1 | 2/2005 | Smith et al. |
| 2005/0043690 A1 | 2/2005 | Todd |
| 2005/0049616 A1 | 3/2005 | Rivera et al. |
| 2005/0065397 A1 | 3/2005 | Saadat et al. |
| 2005/0065517 A1 | 3/2005 | Chin |
| 2005/0070754 A1 | 3/2005 | Nobis et al. |
| 2005/0070763 A1 | 3/2005 | Nobis et al. |
| 2005/0070764 A1 | 3/2005 | Nobis et al. |
| 2005/0080413 A1 | 4/2005 | Canady |
| 2005/0085693 A1 | 4/2005 | Belson et al. |
| 2005/0085832 A1 | 4/2005 | Sancoff et al. |
| 2005/0090837 A1 | 4/2005 | Sixto, Jr. et al. |
| 2005/0090838 A1 | 4/2005 | Sixto, Jr. et al. |
| 2005/0101837 A1 | 5/2005 | Kalloo et al. |
| 2005/0101838 A1 | 5/2005 | Camillocci et al. |
| 2005/0101984 A1 | 5/2005 | Chanduszko et al. |
| 2005/0107663 A1 | 5/2005 | Saadat et al. |
| 2005/0107664 A1 | 5/2005 | Kalloo et al. |
| 2005/0110881 A1 | 5/2005 | Glukhovsky et al. |
| 2005/0113847 A1 | 5/2005 | Gadberry et al. |
| 2005/0119613 A1 | 6/2005 | Moenning et al. |
| 2005/0124855 A1 | 6/2005 | Jaffe et al. |
| 2005/0125010 A1 | 6/2005 | Smith et al. |
| 2005/0131279 A1 | 6/2005 | Boulais et al. |
| 2005/0131457 A1 | 6/2005 | Douglas et al. |
| 2005/0137454 A1 | 6/2005 | Saadat et al. |
| 2005/0143647 A1 | 6/2005 | Minai et al. |
| 2005/0143690 A1 | 6/2005 | High |
| 2005/0143774 A1 | 6/2005 | Polo |
| 2005/0143803 A1 | 6/2005 | Watson et al. |
| 2005/0149087 A1 | 7/2005 | Ahlberg et al. |
| 2005/0149096 A1 | 7/2005 | Hilal et al. |
| 2005/0159648 A1 | 7/2005 | Freed |
| 2005/0165272 A1 | 7/2005 | Okada et al. |
| 2005/0165378 A1 | 7/2005 | Heinrich et al. |
| 2005/0165411 A1 | 7/2005 | Orban, III |
| 2005/0165429 A1 | 7/2005 | Douglas et al. |
| 2005/0182429 A1 | 8/2005 | Yamanouchi |
| 2005/0192478 A1 | 9/2005 | Williams et al. |
| 2005/0192598 A1 | 9/2005 | Johnson et al. |
| 2005/0192602 A1 | 9/2005 | Manzo |
| 2005/0192654 A1 | 9/2005 | Chanduszko et al. |
| 2005/0209624 A1 | 9/2005 | Vijay |
| 2005/0215858 A1 | 9/2005 | Vail, III |
| 2005/0216050 A1 | 9/2005 | Sepetka et al. |
| 2005/0228406 A1 | 10/2005 | Bose |
| 2005/0234297 A1 | 10/2005 | Devierre et al. |

| | | |
|---|---|---|
| 2005/0250983 A1 | 11/2005 | Tremaglio et al. |
| 2005/0250990 A1 | 11/2005 | Le et al. |
| 2005/0250993 A1 | 11/2005 | Jaeger |
| 2005/0251166 A1 | 11/2005 | Vaughan et al. |
| 2005/0251176 A1 | 11/2005 | Swanstrom et al. |
| 2005/0261674 A1 | 11/2005 | Nobis et al. |
| 2005/0267492 A1 | 12/2005 | Poncet et al. |
| 2005/0272975 A1 | 12/2005 | McWeeney et al. |
| 2005/0272977 A1 | 12/2005 | Saadat et al. |
| 2005/0273084 A1 | 12/2005 | Hinman et al. |
| 2005/0274935 A1 | 12/2005 | Nelson |
| 2005/0277945 A1 | 12/2005 | Saadat et al. |
| 2005/0277951 A1 | 12/2005 | Smith et al. |
| 2005/0277952 A1 | 12/2005 | Arp et al. |
| 2005/0277954 A1 | 12/2005 | Smith et al. |
| 2005/0277955 A1 | 12/2005 | Palmer et al. |
| 2005/0277956 A1 | 12/2005 | Francese et al. |
| 2005/0277957 A1 | 12/2005 | Kuhns et al. |
| 2005/0283118 A1 | 12/2005 | Uth et al. |
| 2005/0283119 A1 | 12/2005 | Uth et al. |
| 2005/0288555 A1 | 12/2005 | Binmoeller |
| 2006/0004406 A1 | 1/2006 | Wehrstein et al. |
| 2006/0004409 A1 | 1/2006 | Nobis et al. |
| 2006/0004410 A1 | 1/2006 | Nobis et al. |
| 2006/0015009 A1 | 1/2006 | Jaffe et al. |
| 2006/0020167 A1 | 1/2006 | Sitzmann |
| 2006/0020247 A1 | 1/2006 | Kagan et al. |
| 2006/0025654 A1 | 2/2006 | Suzuki et al. |
| 2006/0025781 A1 | 2/2006 | Young et al. |
| 2006/0025812 A1 | 2/2006 | Shelton, IV |
| 2006/0025819 A1 | 2/2006 | Nobis et al. |
| 2006/0036267 A1 | 2/2006 | Saadat et al. |
| 2006/0041188 A1 | 2/2006 | Dirusso et al. |
| 2006/0058582 A1 | 3/2006 | Maahs et al. |
| 2006/0058776 A1 | 3/2006 | Bilsbury |
| 2006/0069396 A1 | 3/2006 | Meade et al. |
| 2006/0069424 A1 | 3/2006 | Acosta et al. |
| 2006/0069425 A1 | 3/2006 | Hillis et al. |
| 2006/0069429 A1 | 3/2006 | Spence et al. |
| 2006/0074413 A1 | 4/2006 | Behzadian |
| 2006/0079890 A1 | 4/2006 | Guerra |
| 2006/0089528 A1 | 4/2006 | Tartaglia et al. |
| 2006/0095031 A1 | 5/2006 | Ormsby |
| 2006/0095060 A1 | 5/2006 | Mayenberger et al. |
| 2006/0100687 A1 | 5/2006 | Fahey et al. |
| 2006/0106423 A1 | 5/2006 | Weisel et al. |
| 2006/0111209 A1 | 5/2006 | Hinman et al. |
| 2006/0111210 A1 | 5/2006 | Hinman |
| 2006/0111704 A1 | 5/2006 | Brenneman et al. |
| 2006/0129166 A1 | 6/2006 | Lavelle |
| 2006/0135962 A1 | 6/2006 | Kick et al. |
| 2006/0135971 A1 | 6/2006 | Swanstrom et al. |
| 2006/0135984 A1 | 6/2006 | Kramer et al. |
| 2006/0142644 A1 | 6/2006 | Mulac et al. |
| 2006/0142652 A1 | 6/2006 | Keenan |
| 2006/0142790 A1 | 6/2006 | Gertner |
| 2006/0142798 A1 | 6/2006 | Holman et al. |
| 2006/0149131 A1 | 7/2006 | Or |
| 2006/0149132 A1 | 7/2006 | Iddan |
| 2006/0149135 A1 | 7/2006 | Paz |
| 2006/0161190 A1 | 7/2006 | Gadberry et al. |
| 2006/0167416 A1 | 7/2006 | Mathis et al. |
| 2006/0167482 A1 | 7/2006 | Swain et al. |
| 2006/0178560 A1 | 8/2006 | Saadat et al. |
| 2006/0183975 A1 | 8/2006 | Saadat et al. |
| 2006/0184161 A1 | 8/2006 | Maahs et al. |
| 2006/0189844 A1 | 8/2006 | Tien |
| 2006/0189845 A1 | 8/2006 | Maahs et al. |
| 2006/0190027 A1 | 8/2006 | Downey |
| 2006/0195084 A1 | 8/2006 | Slater |
| 2006/0200005 A1 | 9/2006 | Bjork et al. |
| 2006/0200121 A1 | 9/2006 | Mowery |
| 2006/0200169 A1 | 9/2006 | Sniffin |
| 2006/0200170 A1 | 9/2006 | Aranyi |
| 2006/0200199 A1 | 9/2006 | Bonutti et al. |
| 2006/0217665 A1 | 9/2006 | Prosek |
| 2006/0217697 A1 | 9/2006 | Lau et al. |
| 2006/0217742 A1 | 9/2006 | Messerly et al. |
| 2006/0217743 A1 | 9/2006 | Messerly et al. |
| 2006/0229639 A1 | 10/2006 | Whitfield |
| 2006/0229640 A1 | 10/2006 | Whitfield |
| 2006/0237022 A1 | 10/2006 | Chen et al. |
| 2006/0237023 A1 | 10/2006 | Cox et al. |
| 2006/0241570 A1 | 10/2006 | Wilk |
| 2006/0247576 A1 | 11/2006 | Poncet |
| 2006/0247673 A1 | 11/2006 | Voegele et al. |
| 2006/0253004 A1 | 11/2006 | Frisch et al. |
| 2006/0253039 A1 | 11/2006 | McKenna et al. |
| 2006/0258907 A1 | 11/2006 | Stefanchik et al. |
| 2006/0258908 A1 | 11/2006 | Stefanchik et al. |
| 2006/0258910 A1 | 11/2006 | Stefanchik et al. |
| 2006/0258954 A1 | 11/2006 | Timberlake et al. |
| 2006/0258955 A1 | 11/2006 | Hoffman et al. |
| 2006/0259010 A1 | 11/2006 | Stefanchik et al. |
| 2006/0264752 A1 | 11/2006 | Rubinsky et al. |
| 2006/0264904 A1 | 11/2006 | Kerby et al. |
| 2006/0264930 A1 | 11/2006 | Nishimura |
| 2006/0270902 A1 | 11/2006 | Igarashi et al. |
| 2006/0271042 A1 | 11/2006 | Latterell et al. |
| 2006/0271102 A1 | 11/2006 | Bosshard et al. |
| 2006/0276835 A1 | 12/2006 | Uchida |
| 2006/0281970 A1 | 12/2006 | Stokes et al. |
| 2006/0282106 A1 | 12/2006 | Cole et al. |
| 2006/0285732 A1 | 12/2006 | Horn et al. |
| 2006/0287644 A1 | 12/2006 | Inganas et al. |
| 2006/0287666 A1 | 12/2006 | Saadat et al. |
| 2006/0293626 A1 | 12/2006 | Byrum et al. |
| 2007/0002135 A1 | 1/2007 | Glukhovsky |
| 2007/0005019 A1 | 1/2007 | Okishige |
| 2007/0010801 A1 | 1/2007 | Chen et al. |
| 2007/0015965 A1 | 1/2007 | Cox et al. |
| 2007/0016225 A1 | 1/2007 | Nakao |
| 2007/0032700 A1 | 2/2007 | Fowler et al. |
| 2007/0032701 A1 | 2/2007 | Fowler et al. |
| 2007/0043261 A1 | 2/2007 | Watanabe et al. |
| 2007/0043345 A1 | 2/2007 | Davalos et al. |
| 2007/0049800 A1 | 3/2007 | Boulais |
| 2007/0049902 A1 | 3/2007 | Griffin et al. |
| 2007/0051375 A1 | 3/2007 | Milliman |
| 2007/0060880 A1 | 3/2007 | Gregorich et al. |
| 2007/0067017 A1 | 3/2007 | Trapp |
| 2007/0073102 A1 | 3/2007 | Matsuno et al. |
| 2007/0073269 A1 | 3/2007 | Becker |
| 2007/0079924 A1 | 4/2007 | Saadat et al. |
| 2007/0088370 A1 | 4/2007 | Kahle et al. |
| 2007/0100376 A1 | 5/2007 | Mikkaichi et al. |
| 2007/0106118 A1 | 5/2007 | Moriyama |
| 2007/0112251 A1 | 5/2007 | Nakhuda |
| 2007/0112331 A1 | 5/2007 | Weber et al. |
| 2007/0112342 A1 | 5/2007 | Pearson et al. |
| 2007/0112383 A1 | 5/2007 | Conlon et al. |
| 2007/0112384 A1 | 5/2007 | Conlon et al. |
| 2007/0112385 A1 | 5/2007 | Conlon |
| 2007/0112417 A1 | 5/2007 | Shanley et al. |
| 2007/0112425 A1 | 5/2007 | Schaller et al. |
| 2007/0118115 A1 | 5/2007 | Artale et al. |
| 2007/0122425 A1 | 5/2007 | Keeler et al. |
| 2007/0123840 A1 | 5/2007 | Cox |
| 2007/0129605 A1 | 6/2007 | Schaaf |
| 2007/0129719 A1 | 6/2007 | Kendale et al. |
| 2007/0129760 A1 | 6/2007 | Demarais et al. |
| 2007/0135709 A1 | 6/2007 | Rioux et al. |
| 2007/0135803 A1 | 6/2007 | Belson |
| 2007/0142706 A1 | 6/2007 | Matsui et al. |
| 2007/0142780 A1 | 6/2007 | Van Lue |
| 2007/0154460 A1 | 7/2007 | Kraft et al. |
| 2007/0156028 A1 | 7/2007 | Van Lue et al. |
| 2007/0156127 A1 | 7/2007 | Rioux et al. |
| 2007/0161855 A1 | 7/2007 | Mikkaichi et al. |
| 2007/0162101 A1 | 7/2007 | Burgermeister et al. |
| 2007/0167901 A1 | 7/2007 | Herrig et al. |
| 2007/0173691 A1 | 7/2007 | Yokoi et al. |
| 2007/0173869 A1 | 7/2007 | Gannoe et al. |
| 2007/0173870 A2 | 7/2007 | Zacharias |
| 2007/0173872 A1 | 7/2007 | Neuenfeldt |
| 2007/0179525 A1 | 8/2007 | Frecker et al. |
| 2007/0179530 A1 | 8/2007 | Tieu et al. |
| 2007/0197865 A1 | 8/2007 | Miyake et al. |

| Publication No. | Date | Name |
|---|---|---|
| 2007/0198057 A1 | 8/2007 | Gelbart et al. |
| 2007/0203398 A1 | 8/2007 | Bonadio et al. |
| 2007/0203487 A1 | 8/2007 | Sugita |
| 2007/0208336 A1 | 9/2007 | Kim et al. |
| 2007/0208364 A1 | 9/2007 | Smith et al. |
| 2007/0213754 A1 | 9/2007 | Mikkaichi et al. |
| 2007/0225554 A1 | 9/2007 | Maseda et al. |
| 2007/0233040 A1 | 10/2007 | Macnamara et al. |
| 2007/0244358 A1 | 10/2007 | Lee |
| 2007/0250038 A1 | 10/2007 | Boulais |
| 2007/0250057 A1 | 10/2007 | Nobis et al. |
| 2007/0255096 A1 | 11/2007 | Stefanchik et al. |
| 2007/0255100 A1 | 11/2007 | Barlow et al. |
| 2007/0255273 A1 | 11/2007 | Fernandez et al. |
| 2007/0255303 A1 | 11/2007 | Bakos et al. |
| 2007/0255306 A1 | 11/2007 | Conlon et al. |
| 2007/0260112 A1 | 11/2007 | Rahmani |
| 2007/0260117 A1 | 11/2007 | Zwolinski et al. |
| 2007/0260121 A1 | 11/2007 | Bakos et al. |
| 2007/0260242 A1 | 11/2007 | Dycus et al. |
| 2007/0260273 A1 | 11/2007 | Cropper et al. |
| 2007/0270629 A1 | 11/2007 | Charles |
| 2007/0270889 A1 | 11/2007 | Conlon et al. |
| 2007/0270895 A1 | 11/2007 | Nobis et al. |
| 2007/0270907 A1 | 11/2007 | Stokes et al. |
| 2007/0282371 A1 | 12/2007 | Lee et al. |
| 2007/0293727 A1 | 12/2007 | Goldfarb et al. |
| 2007/0299387 A1 | 12/2007 | Williams et al. |
| 2008/0004650 A1 | 1/2008 | George |
| 2008/0015409 A1 | 1/2008 | Barlow et al. |
| 2008/0015413 A1 | 1/2008 | Barlow et al. |
| 2008/0015552 A1 | 1/2008 | Doyle et al. |
| 2008/0021416 A1 | 1/2008 | Arai et al. |
| 2008/0022927 A1 | 1/2008 | Zhang et al. |
| 2008/0027387 A1 | 1/2008 | Grabinsky |
| 2008/0033451 A1 | 2/2008 | Rieber et al. |
| 2008/0051629 A1 | 2/2008 | Sugiyama et al. |
| 2008/0051735 A1 | 2/2008 | Measamer et al. |
| 2008/0058586 A1 | 3/2008 | Karpiel |
| 2008/0058854 A1 | 3/2008 | Kieturakis et al. |
| 2008/0065169 A1 | 3/2008 | Colliou et al. |
| 2008/0071264 A1 | 3/2008 | Azure |
| 2008/0086172 A1 | 4/2008 | Martin et al. |
| 2008/0097159 A1 | 4/2008 | Ishiguro |
| 2008/0097472 A1 | 4/2008 | Agmon et al. |
| 2008/0097483 A1 | 4/2008 | Ortiz et al. |
| 2008/0103527 A1 | 5/2008 | Martin et al. |
| 2008/0114384 A1 | 5/2008 | Chang et al. |
| 2008/0119870 A1 | 5/2008 | Williams |
| 2008/0119891 A1 | 5/2008 | Miles et al. |
| 2008/0125796 A1 | 5/2008 | Graham |
| 2008/0132892 A1 | 6/2008 | Lunsford et al. |
| 2008/0139882 A1 | 6/2008 | Fujimori |
| 2008/0140071 A1 | 6/2008 | Vegesna |
| 2008/0147113 A1 | 6/2008 | Nobis et al. |
| 2008/0171907 A1 | 7/2008 | Long et al. |
| 2008/0177135 A1 | 7/2008 | Muyari et al. |
| 2008/0188710 A1 | 8/2008 | Segawa et al. |
| 2008/0188868 A1 | 8/2008 | Weitzner et al. |
| 2008/0200755 A1 | 8/2008 | Bakos |
| 2008/0200762 A1 | 8/2008 | Stokes et al. |
| 2008/0200911 A1 | 8/2008 | Long |
| 2008/0200933 A1 | 8/2008 | Bakos et al. |
| 2008/0200934 A1 | 8/2008 | Fox |
| 2008/0208213 A1 | 8/2008 | Benjamin et al. |
| 2008/0221587 A1 | 9/2008 | Schwartz |
| 2008/0228213 A1 | 9/2008 | Blakeney et al. |
| 2008/0230972 A1 | 9/2008 | Ganley |
| 2008/0234696 A1 | 9/2008 | Taylor et al. |
| 2008/0243106 A1 | 10/2008 | Coe et al. |
| 2008/0243176 A1 | 10/2008 | Weitzner et al. |
| 2008/0249567 A1 | 10/2008 | Kaplan |
| 2008/0262513 A1 | 10/2008 | Stahler et al. |
| 2008/0262540 A1 | 10/2008 | Bangera et al. |
| 2008/0269782 A1 | 10/2008 | Stefanchik et al. |
| 2008/0269783 A1 | 10/2008 | Griffith |
| 2008/0275474 A1 | 11/2008 | Martin et al. |
| 2008/0275475 A1 | 11/2008 | Schwemberger et al. |
| 2008/0287737 A1 | 11/2008 | Dejima |
| 2008/0287983 A1 | 11/2008 | Smith et al. |
| 2008/0300461 A1 | 12/2008 | Shaw et al. |
| 2008/0300547 A1 | 12/2008 | Bakos |
| 2008/0309758 A1 | 12/2008 | Karasawa et al. |
| 2008/0312496 A1 | 12/2008 | Zwolinski |
| 2008/0312499 A1 | 12/2008 | Handa et al. |
| 2008/0312500 A1 | 12/2008 | Asada et al. |
| 2008/0312506 A1 | 12/2008 | Spivey et al. |
| 2008/0319436 A1 | 12/2008 | Daniel et al. |
| 2008/0319439 A1 | 12/2008 | Ootsubu |
| 2009/0054728 A1 | 2/2009 | Trusty |
| 2009/0062788 A1 | 3/2009 | Long et al. |
| 2009/0062792 A1 | 3/2009 | Vakharia et al. |
| 2009/0062795 A1 | 3/2009 | Vakharia et al. |
| 2009/0069634 A1 | 3/2009 | Larkin |
| 2009/0076499 A1 | 3/2009 | Azure |
| 2009/0078736 A1 | 3/2009 | Van Lue |
| 2009/0082776 A1 | 3/2009 | Cresina |
| 2009/0082779 A1 | 3/2009 | Nakao |
| 2009/0112059 A1 | 4/2009 | Nobis |
| 2009/0112062 A1 | 4/2009 | Bakos |
| 2009/0112063 A1 | 4/2009 | Bakos et al. |
| 2009/0125042 A1 | 5/2009 | Mouw |
| 2009/0131751 A1 | 5/2009 | Spivey et al. |
| 2009/0131932 A1 | 5/2009 | Vakharia et al. |
| 2009/0131933 A1 | 5/2009 | Ghabrial et al. |
| 2009/0143639 A1 | 6/2009 | Stark |
| 2009/0143649 A1 | 6/2009 | Rossi |
| 2009/0143794 A1 | 6/2009 | Conlon et al. |
| 2009/0143818 A1 | 6/2009 | Faller et al. |
| 2009/0149710 A1 | 6/2009 | Stefanchik et al. |
| 2009/0177031 A1 | 7/2009 | Surti et al. |
| 2009/0177219 A1 | 7/2009 | Conlon |
| 2009/0182332 A1 | 7/2009 | Long et al. |
| 2009/0192344 A1 | 7/2009 | Bakos et al. |
| 2009/0192534 A1 | 7/2009 | Ortiz et al. |
| 2009/0198231 A1 | 8/2009 | Esser et al. |
| 2009/0198253 A1* | 8/2009 | Omori ............................ 606/130 |
| 2009/0216248 A1* | 8/2009 | Uenohara et al. ............. 606/130 |
| 2009/0227828 A1 | 9/2009 | Swain et al. |
| 2009/0248055 A1 | 10/2009 | Spivey et al. |
| 2009/0269317 A1 | 10/2009 | Davalos |
| 2009/0281559 A1 | 11/2009 | Swain et al. |
| 2009/0287206 A1 | 11/2009 | Jun |
| 2009/0287236 A1 | 11/2009 | Bakos et al. |
| 2009/0292164 A1 | 11/2009 | Yamatani |
| 2009/0299135 A1 | 12/2009 | Spivey |
| 2009/0299143 A1 | 12/2009 | Conlon et al. |
| 2009/0299362 A1 | 12/2009 | Long et al. |
| 2009/0299385 A1 | 12/2009 | Stefanchik et al. |
| 2009/0299406 A1 | 12/2009 | Swain et al. |
| 2009/0299409 A1 | 12/2009 | Coe et al. |
| 2009/0306658 A1 | 12/2009 | Nobis et al. |
| 2009/0306683 A1 | 12/2009 | Zwolinski et al. |
| 2009/0322864 A1 | 12/2009 | Karasawa et al. |
| 2009/0326332 A1 | 12/2009 | Carter |
| 2009/0326561 A1 | 12/2009 | Carroll, II et al. |
| 2010/0010294 A1 | 1/2010 | Conlon et al. |
| 2010/0010298 A1 | 1/2010 | Bakos et al. |
| 2010/0010299 A1 | 1/2010 | Bakos et al. |
| 2010/0010303 A1 | 1/2010 | Bakos |
| 2010/0010510 A1 | 1/2010 | Stefanchik |
| 2010/0010511 A1 | 1/2010 | Harris et al. |
| 2010/0023032 A1 | 1/2010 | Granja Filho |
| 2010/0030211 A1 | 2/2010 | Davalos et al. |
| 2010/0036198 A1 | 2/2010 | Tacchino et al. |
| 2010/0042045 A1 | 2/2010 | Splvey |
| 2010/0048990 A1 | 2/2010 | Bakos |
| 2010/0049190 A1 | 2/2010 | Long et al. |
| 2010/0049223 A1 | 2/2010 | Granja Filho |
| 2010/0056861 A1 | 3/2010 | Spivey |
| 2010/0056862 A1 | 3/2010 | Bakos |
| 2010/0056864 A1 | 3/2010 | Lee |
| 2010/0057085 A1 | 3/2010 | Holcomb et al. |
| 2010/0057108 A1 | 3/2010 | Spivey et al. |
| 2010/0063538 A1 | 3/2010 | Spivey et al. |
| 2010/0076451 A1 | 3/2010 | Zwolinski et al. |
| 2010/0081877 A1 | 4/2010 | Vakharia |
| 2010/0087813 A1 | 4/2010 | Long |

| | | | | | | |
|---|---|---|---|---|---|---|
| 2010/0113872 A1 | 5/2010 | Asada et al. | EP | 1493391 A1 | 1/2005 | |
| 2010/0121362 A1 | 5/2010 | Clague et al. | EP | 0848598 B1 | 2/2005 | |
| 2010/0130817 A1 | 5/2010 | Conlon | EP | 1281360 B1 | 3/2005 | |
| 2010/0130975 A1 | 5/2010 | Long | EP | 1568330 A1 | 8/2005 | |
| 2010/0131005 A1 | 5/2010 | Conlon | EP | 1452143 B1 | 9/2005 | |
| 2010/0152539 A1 | 6/2010 | Ghabrial et al. | EP | 1616527 A2 | 1/2006 | |
| 2010/0152609 A1 | 6/2010 | Zwolinski et al. | EP | 1006888 B1 | 3/2006 | |
| 2010/0152746 A1 | 6/2010 | Ceniccola et al. | EP | 1629764 A1 | 3/2006 | |
| 2010/0179510 A1 | 7/2010 | Fox et al. | EP | 1013229 B1 | 6/2006 | |
| 2010/0179530 A1 | 7/2010 | Long et al. | EP | 1721561 A1 | 11/2006 | |
| 2010/0191050 A1 | 7/2010 | Zwolinski | EP | 1153578 B1 | 3/2007 | |
| 2010/0191267 A1 | 7/2010 | Fox | EP | 1334696 B1 | 3/2007 | |
| 2010/0198005 A1 | 8/2010 | Fox | EP | 1769766 A1 | 4/2007 | |
| 2010/0198149 A1 | 8/2010 | Fox | EP | 1836971 A2 | 9/2007 | |
| 2010/0198244 A1 | 8/2010 | Spivey et al. | EP | 1836980 A1 | 9/2007 | |
| 2010/0198248 A1 | 8/2010 | Vakharia | EP | 1854421 A2 | 11/2007 | |
| 2010/0249700 A1 | 9/2010 | Spivey | EP | 1857061 A1 | 11/2007 | |
| 2010/0261994 A1 | 10/2010 | Davalos et al. | EP | 1875876 A1 | 1/2008 | |
| 2010/0286791 A1 | 11/2010 | Goldsmith | EP | 1891881 A1 | 2/2008 | |
| 2010/0298642 A1 | 11/2010 | Trusty et al. | EP | 1902663 A1 | 3/2008 | |
| 2010/0312056 A1 | 12/2010 | Galperin et al. | EP | 1477106 B1 | 6/2008 | |
| 2010/0331622 A2 | 12/2010 | Conlon | EP | 1949844 A1 | 7/2008 | |
| 2010/0331758 A1 | 12/2010 | Davalos et al. | EP | 1518499 B1 | 8/2008 | |
| 2010/0331774 A2 | 12/2010 | Spivey | EP | 1582138 B1 | 9/2008 | |
| 2011/0093009 A1 | 4/2011 | Fox | EP | 1709918 B1 | 10/2008 | |
| 2011/0098694 A1 | 4/2011 | Long | EP | 1985226 A2 | 10/2008 | |
| 2011/0098704 A1 | 4/2011 | Long et al. | EP | 1994904 A1 | 11/2008 | |
| 2011/0105850 A1 | 5/2011 | Voegele et al. | EP | 1707130 B1 | 12/2008 | |
| 2011/0106221 A1 | 5/2011 | Neal, II et al. | EP | 0723462 A1 | 3/2009 | |
| 2011/0112434 A1 | 5/2011 | Ghabrial et al. | EP | 1769749 B1 | 11/2009 | |
| 2011/0115891 A1 | 5/2011 | Trusty | EP | 1493397 B1 | 9/2011 | |
| 2011/0124964 A1 | 5/2011 | Nobis | FR | 2731610 A1 | 9/1996 | |
| 2011/0152610 A1 | 6/2011 | Trusty et al. | GB | 330629 A | 6/1930 | |
| 2011/0152612 A1 | 6/2011 | Trusty et al. | GB | 2335860 A | 10/1999 | |
| 2011/0152858 A1 | 6/2011 | Long et al. | GB | 2403909 A | 1/2005 | |
| 2011/0152859 A1 | 6/2011 | Long et al. | GB | 2421190 A | 6/2006 | |
| 2011/0152878 A1 | 6/2011 | Trusty et al. | GB | 2443261 A | 4/2008 | |
| 2011/0152923 A1 | 6/2011 | Fox | JP | 56-46674 | 4/1981 | |
| 2011/0160514 A1 | 6/2011 | Long et al. | JP | 63309252 A | 12/1988 | |
| 2011/0190659 A1 | 8/2011 | Long et al. | JP | 4038960 A | 2/1992 | |
| 2011/0190764 A1 | 8/2011 | Long et al. | JP | 8-29699 A | 2/1996 | |
| 2011/0193948 A1 | 8/2011 | Amling et al. | JP | 2000245683 | * 9/2000 | |
| 2011/0245619 A1 | 10/2011 | Holcomb | JP | 2002-369791 A | 12/2002 | |
| 2011/0285488 A1 | 11/2011 | Scott et al. | JP | 2003-088494 A | 3/2003 | |
| 2011/0306971 A1 | 12/2011 | Long | JP | 2003-235852 A | 8/2003 | |
| 2012/0004502 A1* | 1/2012 | Weitzner et al. ............. 600/102 | JP | 2004-33525 A | 2/2004 | |
| 2012/0088965 A1 | 4/2012 | Stokes et al. | JP | 2004-065745 A | 3/2004 | |
| 2012/0089089 A1 | 4/2012 | Swain et al. | JP | 2005-121947 A | 5/2005 | |
| 2012/0089093 A1 | 4/2012 | Trusty | JP | 2005-261514 A | 9/2005 | |
| 2012/0116155 A1 | 5/2012 | Trusty | JP | 2006297005 A | 11/2006 | |
| 2012/0179148 A1 | 7/2012 | Conlon | NL | 1021295 C2 | 2/2004 | |
| 2012/0191075 A1 | 7/2012 | Trusty | SU | 194230 | 5/1967 | |
| 2012/0191076 A1 | 7/2012 | Voegele et al. | SU | 980703 | 12/1982 | |
| FOREIGN PATENT DOCUMENTS | | | WO | WO 84/01707 A1 | 5/1984 | |
| | | | WO | WO 92/13494 A1 | 8/1992 | |
| DE | 3008120 A1 | 9/1980 | WO | WO 93/10850 A1 | 6/1993 | |
| DE | 4323585 A1 | 1/1995 | WO | WO 93/20760 A1 | 10/1993 | |
| DE | 19713797 A1 | 10/1997 | WO | WO 93/20765 A1 | 10/1993 | |
| DE | 19757056 B4 | 8/2008 | WO | WO 95/09666 A1 | 4/1995 | |
| DE | 102006027873 B4 | 10/2009 | WO | WO 96/22056 A1 | 7/1996 | |
| EP | 0086338 A1 | 8/1983 | WO | WO 96/27331 A1 | 9/1996 | |
| EP | 0286415 A2 | 10/1988 | WO | WO 96/39946 A1 | 12/1996 | |
| EP | 0589454 A2 | 3/1994 | WO | WO 97/12557 A1 | 4/1997 | |
| EP | 0464479 B1 | 3/1995 | WO | WO 98/01080 A1 | 1/1998 | |
| EP | 0529675 B1 | 2/1996 | WO | WO 99/00060 A1 | 1/1999 | |
| EP | 0724863 B1 | 7/1999 | WO | WO 99/09919 A1 | 3/1999 | |
| EP | 0760629 B1 | 11/1999 | WO | WO 99/17661 A1 | 4/1999 | |
| EP | 0818974 B1 | 7/2001 | WO | WO 99/30622 A2 | 6/1999 | |
| EP | 1281356 A2 | 2/2003 | WO | WO 00/35358 A1 | 6/2000 | |
| EP | 0947166 B1 | 5/2003 | WO | WO 01/10319 A1 | 2/2001 | |
| EP | 0836832 B1 | 12/2003 | WO | WO 01/26708 A1 | 4/2001 | |
| EP | 1402837 A1 | 3/2004 | WO | WO 01/41627 A2 | 6/2001 | |
| EP | 0744918 B1 | 4/2004 | WO | WO 01/58360 A2 | 8/2001 | |
| EP | 0931515 B1 | 8/2004 | WO | WO 02/11621 A1 | 2/2002 | |
| EP | 0941128 B1 | 10/2004 | WO | WO 02/34122 A2 | 5/2002 | |
| EP | 1411843 B1 | 10/2004 | WO | WO 02/094082 A2 | 11/2002 | |
| EP | 1150614 B1 | 11/2004 | WO | WO 03/045260 A1 | 6/2003 | |
| EP | 1477104 A1 | 11/2004 | WO | WO 03/047684 A2 | 6/2003 | |
| EP | 1481642 A1 | 12/2004 | WO | WO 03/059412 A2 | 7/2003 | |

| | | |
|---|---|---|
| WO | WO 03/078721 A2 | 9/2003 |
| WO | WO 03/081761 A2 | 10/2003 |
| WO | WO 03/082129 A2 | 10/2003 |
| WO | WO 2004/006789 A1 | 1/2004 |
| WO | WO 2004/028613 A2 | 4/2004 |
| WO | WO 2004/037123 A1 | 5/2004 |
| WO | WO 2004/037149 A1 | 5/2004 |
| WO | WO 2004/052221 A1 | 6/2004 |
| WO | WO 2004/086984 A1 | 10/2004 |
| WO | WO 2005/009211 A2 | 2/2005 |
| WO | WO 2005/018467 A2 | 3/2005 |
| WO | WO 2005/037088 A2 | 4/2005 |
| WO | WO 2005/048827 A1 | 6/2005 |
| WO | WO 2005/065284 A2 | 7/2005 |
| WO | WO 2005/097019 A2 | 10/2005 |
| WO | WO 2005/097234 A2 | 10/2005 |
| WO | WO 2005/112810 A2 | 12/2005 |
| WO | WO 2005/120363 A1 | 12/2005 |
| WO | WO 2005/122866 A1 | 12/2005 |
| WO | WO 2006/007399 A1 | 1/2006 |
| WO | WO 2006/012630 A2 | 2/2006 |
| WO | WO 2006/040109 A1 | 4/2006 |
| WO | WO 2006/041881 A2 | 4/2006 |
| WO | WO 2006/060405 A2 | 6/2006 |
| WO | WO 2006/110733 A2 | 10/2006 |
| WO | WO 2006/113216 A2 | 10/2006 |
| WO | WO 2007/013059 A2 | 2/2007 |
| WO | WO 2007/014063 A2 | 2/2007 |
| WO | WO 2007/048085 A2 | 4/2007 |
| WO | WO 2007/063550 A2 | 6/2007 |
| WO | WO 2007/100067 A1 | 9/2007 |
| WO | WO 2007/109171 A2 | 9/2007 |
| WO | WO 2008/005433 A1 | 1/2008 |
| WO | WO 2008/033356 A2 | 3/2008 |
| WO | WO 2008/041225 A2 | 4/2008 |
| WO | WO 2008/076337 A1 | 6/2008 |
| WO | WO 2008/076800 A2 | 6/2008 |
| WO | WO 2008/079440 A2 | 7/2008 |
| WO | WO 2008/101075 A2 | 8/2008 |
| WO | WO 2008/102154 A2 | 8/2008 |
| WO | WO 2008/108863 A2 | 9/2008 |
| WO | WO 2008/151237 A1 | 12/2008 |
| WO | WO 2009/021030 A1 | 2/2009 |
| WO | WO 2009/027065 A1 | 3/2009 |
| WO | WO 2009/029065 A1 | 3/2009 |
| WO | WO 2009/032623 A2 | 3/2009 |
| WO | WO 2009/121017 A1 | 10/2009 |
| WO | WO 2010/027688 A1 | 3/2010 |
| WO | WO 2010/056716 A2 | 5/2010 |
| WO | WO 2010/080974 A1 | 7/2010 |
| WO | WO 2010/088481 A1 | 8/2010 |

OTHER PUBLICATIONS

Ethicon, Inc., "Wound Closure Manual: Chapter 3 (The Surgical Needle)," 15 pages, (1994).
Guido M. Sclabas, M.D., et al., "Endoluminal Methods for Gastrotomy Closure in Natural Orifice TransEnteric Surgery (NOTES)," Surgical Innovation, vol. 13, No. 1, pp. 23-30, Mar. 2006.
Fritscher-Ravens, et al., "Transgastric Gastropexy and Hiatal Hernia Repair for GERD Under EUS Control: a Porcine Model," Gastrointestinal Endoscopy, vol. 59, No. 1, pp. 89-95, 2004.
Ogando, "Prototype Tools That Go With the Flow," Design News, 2 pages, Jul. 17, 2006.
Edd, et al., "In Vivo Results of a New Focal Tissue Ablation Technique: Irreversible Electroporation," IEEE Trans Biomed Eng, vol. 53, pp. 1409-1415, 2006.
Kennedy, et al., "High-Burst-Strength, Feedback-Controlled Bipolar Vessel Sealing," Surgical Endoscopy, vol. 12, pp. 876-878 (1998).
Collins et al., "Local Gene Therapy of Solid Tumors with GM-CSF and B7-1 Eradicates Both Treated and Distal Tumors," Cancer Gene Therapy, vol. 13, pp. 1061-1071 (2006).
K. Sumiyama et al., "Transesophageal Mediastinoscopy by Submucosal Endoscopy With Mucosal Flap Safety Value Technique," Gastrointest Endosc., Apr. 2007, vol. 65(4), pp. 679-683 (Abstract).
K. Sumiyama et al., "Submucosal Endoscopy with Mucosal Flap Safety Valve," Gastrointest Endosc. Apr. 2007, vol. 65(4) pp. 694-695 (Abstract).
K. Sumiyama et al., "Transgastric Cholecystectomy: Transgastric Accessibility to the Gallbladder Improved with the SEMF Method and a Novel Multibending Therapeutic Endoscope," Gastrointest Endosc., Jun. 2007, vol. 65(7), pp. 1028-1034 (Abstract).
K. Sumiyama et al., "Endoscopic Caps," Tech. Gastrointest. Endosc., vol. 8, pp. 28-32, 2006.
"Z-Offset Technique Used in the Introduction of Trocar During Laparoscopic Surgery," M.S. Hershey Notes Presentation to EES Notes Development Team, Sep. 27, 2007.
F.N. Denans, Nouveau Procede Pour La Guerison Des Plaies Des Intestines. Extrait Des Seances De La Societe Royale De Medecine De Marseille, Pendant Le Mois De Decembre 1825, et le Premier Tremestre De 1826, Séance Du 24 Fevrier 1826. Recueil De La Societe Royale De Medecin De Marseille. Marseille: Impr. D'Achard, 1826; 1:127-31. (with English translation).
I. Fraser, "An Historical Perspective on Mechanical Aids in Intestinal Anastamosis," Surg. Gynecol. Obstet. (Oct. 1982), vol. 155, pp. 566-574.
M.E. Ryan et al., "Endoscopic Intervention for Biliary Leaks After Laparoscopic Cholecystectomy: A Multicenter Review," Gastrointest. Endosc., vol. 47(3), 1998, pp. 261-266.
C. Cope, "Creation of Compression Gastroenterostomy by Means of the Oral, Percutaneous, or Surgical Introduction of Magnets: Feasibility Study in Swine," J. Vasc Interv Radiol, (1995), vol. 6(4), pp. 539-545.
J.W. Hazey et al., "Natural Orifice Transgastric Endoscopic Peritoneoscopy in Humans: Initial Clinical Trial," Surg Endosc, (Jan. 2008), vol. 22(1), pp. 16-20.
N. Chopita et al., "Endoscopic Gastroenteric Anastamosis Using Magnets," Endoscopy, (2005), vol. 37(4), pp. 313-317.
C. Cope et al., "Long Term Patency of Experimental Magnetic Compression Gastroenteric Anastomoses Achieved with Covered Stents," Gastrointest Endosc, (2001), vol. 53, pp. 780-784.
H. Okajima et al., "Magnet Compression Anastamosis for Bile Duct Stenosis After Duct to Duct Biliary Reconstruction in Living Donor Liver Transplantation," Liver Transplantation (2005), pp. 473-475.
A. Fritscher-Ravens et al., "Transluminal Endosurgery: Single Lumen Access Anastamotic Device for Flexible Endoscopy," Gastrointestinal Endosc, (2003), vol. 58(4), pp. 585-591.
G.A. Hallenbeck, M.D. et al., "An Instrument for Colorectal Anastomosis Without Sutrues," Dis Col Rectum, (1963), vol. 5, pp. 98-101.
T. Hardy, Jr., M.D. et al., "A Biofragmentable Ring for Sutureless Bowel Anastomosis. An Experimental Study," Dis Col Rectum, (1985), vol. 28, pp. 484-490.
P. O'Neill, M.D. et al., "Nonsuture Intestinal Anastomosis," Am J. Surg, (1962), vol. 104, pp. 761-767.
C.P. Swain, M.D. et al., "Anastomosis at Flexible Endoscopy: An Experimental Study of Compression Button Gastrojejunostomy," Gastrointest Endosc, (1991), vol. 37, pp. 628-632.
J.B. Murphy, M.D., "Cholecysto-Intestinal, Gastro-Intestinal, Entero-Intestinal Anastomosis, and Approximation Without Sutures (original research)," Med Rec, (Dec. 10, 1892), vol. 42(24), pp. 665-676.
USGI® EndoSurgical Operating System—g-Prox® Tissue Grasper/ Approximation Device; [online] URL: http://www.usgimedical.com/eos/components-gprox.htm—accessed May 30, 2008 (2 pages).
Printout of web page—http://www.vacumed.com/zcom/product/Product.do?compid=27&prodid=852, #51XX Low-Cost Permanent Tubes 2MM ID, Smooth Interior Walls, VacuMed, Ventura, California, Accessed Jul. 24, 2007.
Endoscopic Retrograde Cholangiopancreatogram (ERCP); [online] URL: http://www.webmd.com/digestive-disorders/endoscopic-retrograde-cholangiopancreatogram-ercp.htm; last updated: Apr. 30, 2007; accessed: Feb. 21, 2008 (6 pages).
ERCP; Jackson Siegelbaum Gastroenterology; [online] URL: http://www.gicare.com/pated/epdgs20.htm; accessed Feb. 21, 2008 (3 pages).
D.G. Fong et al., "Transcolonic Ventral Wall Hernia Mesh Fixation in a Porcine Model," Endoscopy 2007; 39: 865-869.
B. Rubinsky, Ph.D., "Irreversible Electroporation in Medicine," Technology in Cancer Research and Treatment, vol. 6, No. 4, Aug. (2007), pp. 255-259.

D.B. Nelson, MD et al., "Endoscopic Hemostatic Devices," Gastrointestinal Endoscopy, vol. 54, No. 6, 2001, pp. 833-840.

CRE™ Pulmonary Balloon Dilator; [online] URL: http://www.bostonscientific.com/Device.bsci?page32 HCP_Overview&navRelId=1000.1003&method=D..., accessed Jul. 18, 2008 (4 pages).

J.D. Paulson, M.D., et al., "Development of Flexible Culdoscopy," The Journal of the American Association of Gynecologic Laparoscopists, Nov. 1999, vol. 6, No. 4, pp. 487-490.

H. Seifert, et al., "Retroperitoneal Endoscopic Debridement for Infected Peripancreatic Necrosis," The Lancet, Research Letters, vol. 356, Aug. 19, 2000, pp. 653-655.

K.E. Mönkemüller, M.D., et al., "Transmural Drainage of Pancreatic Fluid Collections Without Electrocautery Using the Seldinger Technique," Gastrointestinal Endoscopy, vol. 48, No. 2, 1998, pp. 195-200, (Received Oct. 3, 1997; Accepted Mar. 31, 1998).

D. Wilhelm et al., "An Innovative, Safe and Sterile Sigmoid Access (ISSA) for NOTES," Endoscopy 2007, vol. 39, pp. 401-406.

Nakazawa et al., "Radiofrequency Ablation of Hepatocellular Carcinoma: Correlation Between Local Tumor Progression After Ablation and Ablative Margin," AJR, 188, pp. 480-488 (Feb. 2007).

Miklavčič et al., "A validated model of in vivo electric field distribution in tissues for electrochemotherapy and for DNA electrotransfer for gene therapy," Biochimica et Biophysica Acta, 1523, pp. 73-83 (2000).

Evans, "Ablative and cathether-delivered therapies for colorectal liver metastases (CRLM)," EJSO, 33, pp. S64-S75 (2007).

Wong et al., "Combined Percutaneous Radiofrequency Ablation and Ethanol Injection for Hepatocellular Carcinoma in High-Risk Locations," AJR, 190, pp. W187-W195 (2008).

Heller et al., "Electrically mediated plasmid DNA delivery to hepatocellular carcinomas in vivo," Gene Therapy, 7, pp. 826-829 (2000).

Widera et al., "Increased DNA Vaccine Delivery and Immunogenicity by Electroporation In Vivo," The Journal of Immunology, 164, pp. 4635-4640 (2000).

Weaver et al., "Theory of electroporation: A review," Bioelectrochemistry and Bioenergetics, 41, pp. 135-160 (1996).

Mulier et al., "Radiofrequency Ablation Versus Resection for Resectable Colorectal Liver Metastases: Time for a Randomized Trial?" Annals of Surgical Oncology, 15(1), pp. 144-157 (2008).

Link et al., "Regional Chemotherapy of Nonresectable Colorectal Liver Metastases with Mitoxanthrone, 5-Fluorouracil, Folinic Acid, and Mitomycin C May Prolong Survival," Cancer, 92, pp. 2746-2753 (2001).

Guyton et al., "Membrane Potentials and Action Potentials," W.B. Sanders, ed. Textbook of Medical Physiology, p. 56 (2000).

Guyton et al., "Contraction of Skeletal Muscle," Textbook of Medical Physiology, pp. 82-84 (2000).

"Ethicon Endo-Surgery Novel Investigational Notes and SSL Devices Featured in 15 Presentations at Sages," Apr. 22, 2009 Press Release; URL http://www.jnj.com/connect/news/all/20090422_152000; accessed Aug. 28, 2009 (3 pages).

"Ethicon Endo-Surgery Studies Presented At DDW Demonstrate Potential of Pure NOTES Surgery With Company's Toolbox," Jun. 3, 2009 Press Release; URL http://www.jnj.com/connect/news/product/20090603_120000; accessed Aug. 28, 2009 (3 pages).

Castellvi et al., "Hybrid Transvaginal NOTES Sleeve Gastrectomy in a Porcine Model Using a Magnetically Anchored Camera and Novel Instrumentation," Abstract submitted along with Poster at SAGES Annual Meeting in Phoenix, AZ, Apr. 22, 2009 (1 page).

Castellvi et al., "Hybrid Transvaginal NOTES Sleeve Gastrectomy in a Porcine Model Using a Magnetically Anchored Camera and Novel Instrumentation," Poster submitted along with Abstract at SAGES Annual Meeting in Phoenix, AZ, Apr. 22, 2009 (1 page).

OCTO Port Modular Laparoscopy System for Single Incision Access, Jan. 4, 2010; URL http://www.medgadget.com/archives/2010/01/octo_port_modular_laparo...; accessed Jan. 5, 2010 (4 pages).

Hakko Retractors, obtained Aug. 25, 2009 (5 pages).

Zadno et al., "Linear Superelasticity in Cold-Worked NI-TIU," Engineering Aspects of Shape Memory Alloys, pp. 414-419.

U.S. Appl. No. 12/607,252, filed Oct. 28, 2009.
U.S. Appl. No. 12/580,400, filed Oct. 16, 2009.
U.S. Appl. No. 12/607,388, filed Oct. 28, 2009.
U.S. Appl. No. 12/612,911, filed Nov. 5, 2009.
U.S. Appl. No. 12/614,143, filed Nov. 6, 2009.
U.S. Appl. No. 12/617,998, filed Nov. 13, 2009.
U.S. Appl. No. 12/640,476, filed Dec. 17, 2009.
U.S. Appl. No. 12/640,492, filed Dec. 17, 2009.
U.S. Appl. No. 12/641,823, filed Dec. 18, 2009.
U.S. Appl. No. 12/641,853, filed Dec. 18, 2009.
U.S. Appl. No. 12/641,837, filed Dec. 18, 2009.
U.S. Appl. No. 12/651,181, filed Dec. 31, 2009.
U.S. Appl. No. 12/696,598, filed Jan. 29, 2010.
U.S. Appl. No. 12/696,626, filed Jan. 29, 2010.
U.S. Appl. No. 12/752,701, filed Apr. 1, 2010.
U.S. Appl. No. 12/640,440, filed Dec. 17, 2009.

International Search Report for PCT/US2010/060295, Jun. 22, 2011, included in the PCT Publication No. WO 2011/084422 A1 (96 sheets).

Zadno et al., "Linear Superelasticity in Cold-Worked NI-TI," Engineering Aspects of Shape Memory Alloys, pp. 414-419 (1990).

How Stuff Works "How Smart Structures Will Work," http://science.howstuffworks.com/engineering/structural/smart-structure1.htm; accessed online Nov. 1, 2011 (3 pages).

Instant Armor: Science Videos—Science News—ScienCentral; http://www.sciencentral.com/articles./view.php3?article_id=218392121; accessed online Nov. 1, 2011 (2 pages).

Stanway, Smart Fluids: Current and Future Developments. Material Science and Technology, 20, pp. 931-939, 2004; accessed online Nov. 1, 2011 at http://www.dynamics.group.shef.ac.uk/smart/smart.html (7 pages).

Jolly et at, Properties and Applications of Commercial Magnetorheological Fluids. SPIE 5th Annual Int. Symposium on Smart Structures and Materials, 1998 (18 pages).

U.S. Appl. No. 13/013,131, filed Jan. 25, 2011.
U.S. Appl. No. 13/013,147, filed Jan. 25, 2011.
U.S. Appl. No. 13/036,895, filed Feb. 28, 2011.
U.S. Appl. No. 13/036,908, filed Feb. 28, 2011.
U.S. Appl. No. 13/267,251, filed Oct. 6, 2011.
U.S. Appl. No. 13/325,791, filed Dec. 14, 2011.
U.S. Appl. No. 13/352,495, filed Jan. 18, 2012.
U.S. Appl. No. 13/399,358, filed Feb. 17, 2012.
U.S. Appl. No. 13/420,805, filed Mar. 15, 2012.
U.S. Appl. No. 13/420,818, filed Mar. 15, 2012.
U.S. Appl. No. 13/425,103, filed Mar. 20, 2012.

Written Opinion for PCT/US2010/060295, Jun. 22, 2011, (8 pages).
International Preliminary Report on Patentability for PCT/US2010/060295, Jun. 19, 2012 (8 pages).

\* cited by examiner

USER INTERFACE SUPPORT DEVICES FOR ENDOSCOPIC SURGICAL INSTRUMENTS

BACKGROUND

The embodiments relate, in general, to endoscopes and medical procedures and, more particularly, to devices for facilitating the insertion and manipulation of endoscopic guide tube assemblies and other surgical instruments within a body cavity to accomplish various surgical and therapeutic procedures.

Minimally invasive procedures are desirable because such procedures can reduce pain and provide relatively quick recovery times as compared with conventional open medical procedures. Many minimally invasive procedures are performed through one or more ports through the abdominal wall, commonly known as trocars. A laparascope that may or may not include a camera, may be used through one of these ports for visualization of the anatomy and surgical instruments may be used simultaneously through other ports. Such devices and procedures permit a physician to position, manipulate, and view anatomy, surgical instruments and accessories inside the patient through a small access opening in the patient's body.

Still less invasive procedures include those that are performed through insertion of an endoscope through a natural body orifice to a treatment region. Examples of this approach include, but are not limited to, cystoscopy, hysteroscopy, esophagogastroduodenoscopy, and colonoscopy. Many of these procedures employ the use of a flexible endoscope and flexible or steerable guide tube assemblies during the procedure. Flexible endoscopes often have a flexible, steerable articulating section near the distal end that can be controlled by the user utilizing controls at the proximal end. Treatment or diagnosis may be completed intralumenally, such as polypectomy or gastroscopy. Alternatively, treatment or diagnosis of extra-luminal anatomy in the abdominal cavity may be completed translumenally, for example, through a gastrotomy, colonotomy or vaginotomy. Minimally invasive therapeutic procedures to treat or diagnose diseased tissue by introducing medical instruments translumenally to a tissue treatment region through a natural opening of the patient are known as Natural Orifice Translumenal Endoscopic Surgery (NOTES™).

Regardless of the type of surgery involved and the method in which the endoscope is inserted into the body, the clinicians and surgical specialists performing such procedures have generally developed skill sets and approaches that rely on anatomical alignment for both visualization and tissue manipulation purposes. Over the years, a variety of different endoscope arrangements, as well as various types of steerable sheaths, guide tubes and overtubes for accommodating endoscopes have been developed. For example, various endoscopic guide systems and endoscopes are disclosed in U.S. patent application Ser. No. 12/468,462, entitled "Manipulatable Guide System and Methods For Natural Orifice Translumenal Endoscopic Surgery", filed May 19, 2009, the disclosure of which is herein incorporated by reference in its entirety. Some of the guide system embodiments disclosed therein include extended articulatable working channels as well as a liftable camera device. Such configurations afford the clinician with the ability to advantageously manipulate and position the working channels while providing the flexibility to position the camera to provide a "bird's eye", "stadium", or laparoscopic view of the theater.

While these and other overtube systems and endoscopic surgical devices represent great advancements in the field of Natural Orifice Translumenal Endoscopic Surgery, various surgical procedures require the simultaneous use and manipulation of several of such devices. For example, typical NOTES procedures being done today employ a standard gastroscope through an overtube to gain access and conduct the surgical procedure through the working channels in the gastroscope. The clinician commonly uses one hand to manage the overtube and the second hand to rotate and/or articulate the gastroscope. Other operations might require the use of three or more surgical instruments, making their coordination and precise manipulation challenging. Similarly some overtube arrangements that can articulate in four directions require the clinician to use both hands to operate.

Consequently a need exists for a device that can facilitate the coordinated operation and support of a plurality of endoscopic surgical devices.

The foregoing discussion is intended only to illustrate some of the shortcomings present in the field at the time, and should not be taken as a disavowal of claim scope.

SUMMARY

Various embodiments of the present invention comprise an interface system for aiding clinicians in controlling and manipulating at least one endoscopic surgical instrument and a cable-controlled guide tube system. The interface system may comprise a tool docking assembly that is supportable relative to the cable-controlled guide system. In various embodiments, the tool docking system may comprise a first tool docking station for retainingly supporting one of the at least one endoscopic surgical instrument handles for selective pivotal travel about a first axis upon application of a first pivotal motion thereto and about a second axis upon application of a second pivotal motion thereto. A first cable attachment assembly may be configured to couple a first cable from the cable controlled guide tube system to the first tool docking station. The interface system may further comprise at least one friction brake assembly that interacts with the first tool docking station for retaining the first tool docking station in a desired position upon discontinuing application of at least one of the first and second pivotal motions to the first tool docking station.

In another general aspect of the present invention there is provided an interface system for interfacing between at least one endoscopic surgical instrument and a cable-controlled guide tube system. Various embodiments may include a central bar that has a first end portion and a second end portion that is spaced from the first end portion. A first tool docking station may be movably coupled to the first end portion of the central bar for selective pivotal travel relative to the central bar about a first axis and a second axis. The first tool docking station may be configured to operably support one of the at least one endoscopic surgical instruments therein. A first cable attachment assembly may be configured to couple a first cable from the cable-controlled guide tube system to the first tool docking station. A second cable attachment assembly may be configured to couple a second cable from the cable-controlled guide tube system to the first tool docking station. A second tool docking station may be movably coupled to the second end portion of the central bar for selective pivotal travel relative to the central bar about a third axis and a fourth axis. The second tool docking station may be configured to operably support another one of the at least one endoscopic surgical instruments therein. A third cable attachment assembly may be configured to couple a third cable from the cable-controlled guide tube system to the second tool docking station. A fourth cable attachment assembly may be configured to couple a fourth cable from the cable-controlled guide tube system to the second tool docking station.

In another general embodiment, there is provided a method for controlling a cable-controlled guide tube system. In various embodiments, the method may comprise movably mounting a surgical instrument that has a first elongated flexible portion to a first tool docking station that is positioned relative to the cable-controlled guide tube system and inserting the first elongated flexible portion through a first steerable working channel in the cable-controlled guide tube system. The method may further comprise affixing a first cable that is attached to the first steerable working channel to the first tool docking station and affixing a second cable that is attached to the first steerable working channel to the first tool docking station. The method may further comprise moving the first tool docking station in a first direction to apply a first actuation motion to the first cable.

BRIEF DESCRIPTION OF THE FIGURES

The novel features of the embodiments described herein are set forth with particularity in the appended claims. The embodiments, however, both as to organization and methods of operation may be better understood by reference to the following description, taken in conjunction with the accompanying drawings as follows.

DETAILED DESCRIPTION

U.S. patent application Ser. No. 12/640,440, entitled "INTERFACE SYSTEMS FOR AIDING CLINICIANS IN CONTROLLING AND MANIPULATING AT LEAST ONE ENDOSCOPIC SURGICAL INSTRUMENT AND A CABLE CONTROLLED GUIDE TUBE SYSTEM", U.S. Patent Application Publication No. 2011/0152878 was filed on even date herewith and is owned by the assignee of the present application is herein incorporated by reference in its entirety.

Certain embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting embodiments and that the scope of these embodiments is defined solely by the claims. The features illustrated or described in connection with one embodiment may be combined with the features of other embodiments. Such modifications and variations are intended to be included within the scope of the appended claims.

The various embodiments generally relate to guide systems and steerable sheath arrangements for use in connection with endoscopes for selectively positioning and manipulating endoscopic tools in a desired orientation within the body cavity. The terms "endoscopic tools" and "endoscopic surgical instruments" as used herein may comprise, for example, endoscopes, lights, insufflation devices, cleaning devices, suction devices, hole-forming devices, imaging devices, cameras, graspers, clip appliers, loops, Radio Frequency (RF) ablation devices, harmonic ablation devices, scissors, knives, suturing devices, etc. However, such term is not limited to those specific devices. As the present Description proceeds, those of ordinary skill in the art will appreciate that the unique and novel features of the various instruments and methods for use thereof may be effectively employed to perform surgical procedures by inserting such endoscopic tools through a natural body lumen (mouth, anus, vagina) or through a transcutaneous port (abdominal trocar, cardiothoracic port) to perform surgical procedures within a body cavity.

Figure 1:
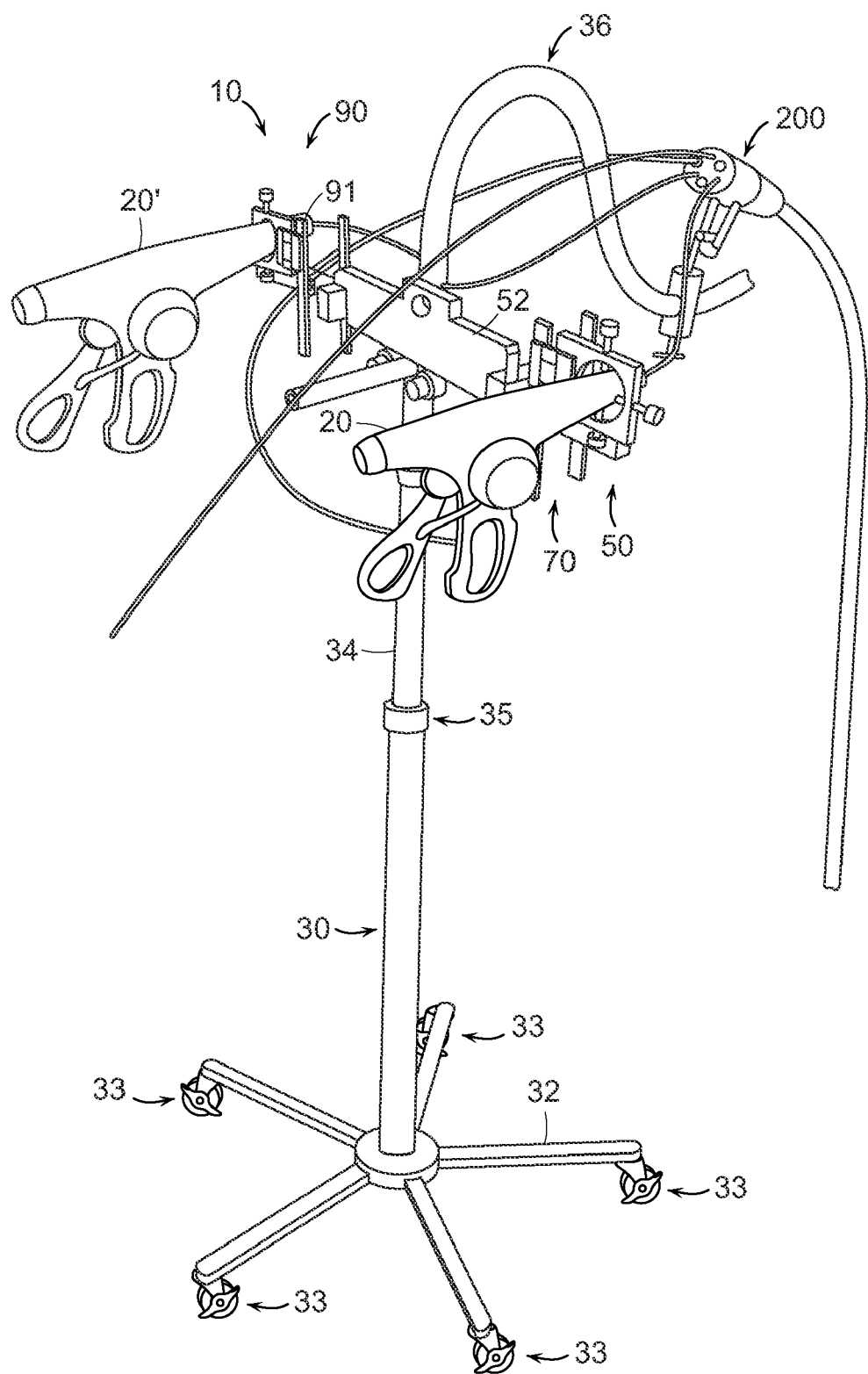
FIG. 1 is a perspective view of a flexible user interface support assembly embodiment of the present invention supporting two surgical instruments relative to a cable-controlled, steerable guide tube assembly.
Figure 1A:
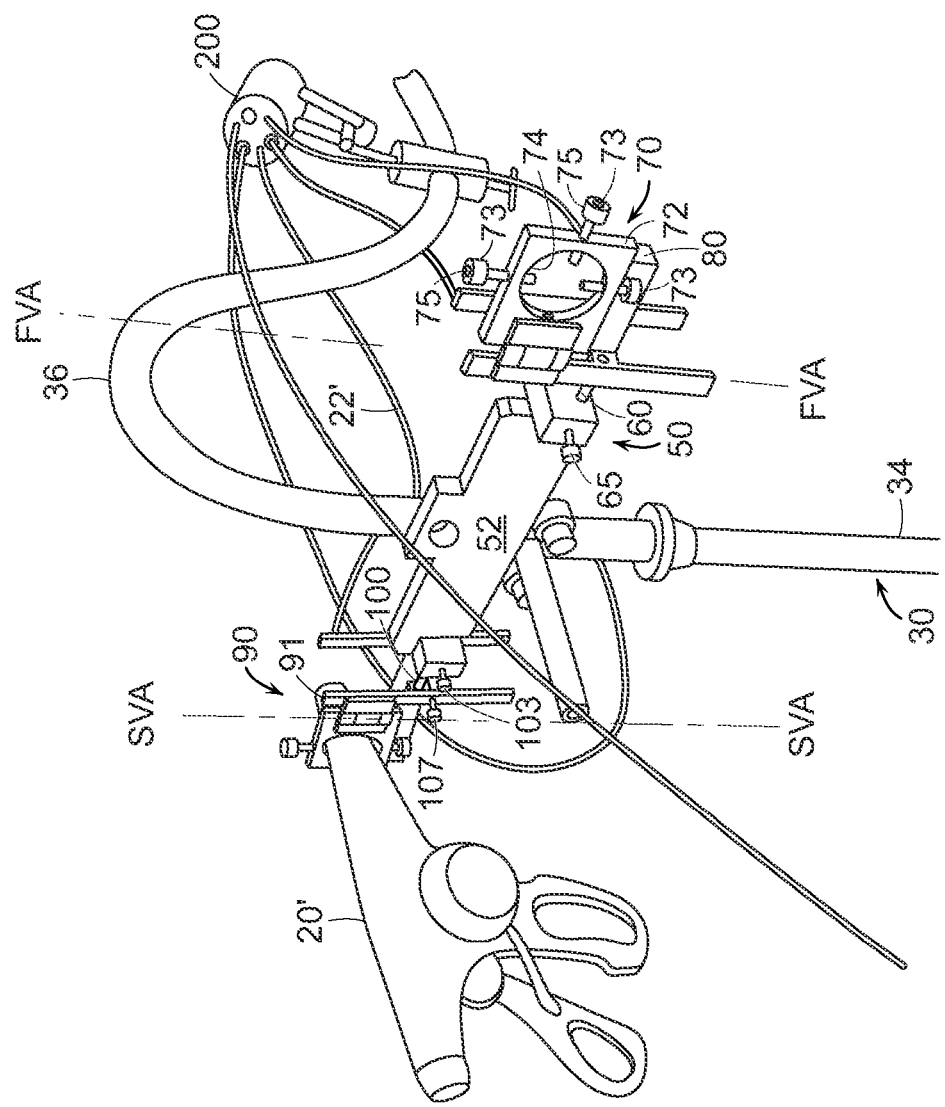
FIG. 1A is an enlarged perspective view of a portion of the flexible user interface embodiment of FIG. 1 with one of the surgical instruments removed for clarity.
Figure 2:
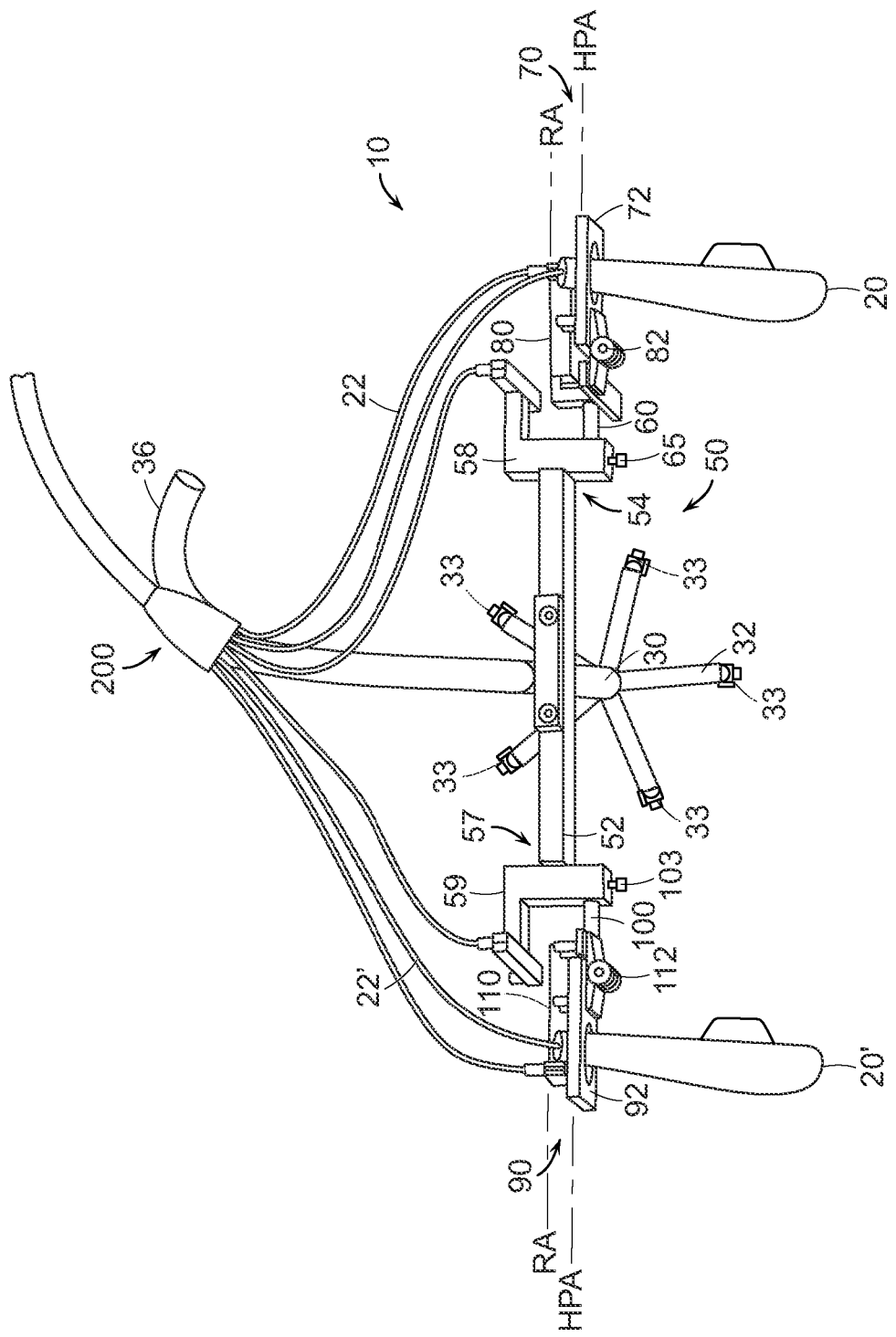
FIG. 2 is a plan view of the flexible user interface and cable-controlled steerable guide tube assembly of FIG. 1.

FIGS. 1 and 2 illustrate an embodiment of a flexible user interface support assembly, generally represented as 10, that may operably support two conventional endoscopic surgical instruments 20, 20'. FIG. 1A illustrates the flexible user interface support assembly 10 with only one surgical instrument docked thereto. The surgical instruments 20, 20' may comprise conventional grasper devices of the type disclosed in U.S. patent application Ser. No. 12/203,330, entitled SURGICAL GRASPING DEVICE, filed Sep. 3, 2008, the disclosure of which is herein incorporated by reference in its entirety. However, the various embodiments of the present invention may be employed with a variety of other types of endoscopic surgical instruments such as, but not limited to, those surgical instruments described above. Accordingly, the scope of protection afforded to the various embodiments disclosed herein should not be limited to their use with a specific type of surgical instrument.

It will be appreciated that the terms "proximal" and "distal" are used herein with reference to a clinician manipulating the surgical instruments 20, 20'. The term "proximal" referring to the portion closest to the clinician and the term "distal" referring to the portion located away from the clinician. It will be further appreciated that for convenience and clarity, spatial terms such as "vertical", "horizontal", "up" and "down", "left" and "right" may be used herein with respect to the drawings. However, surgical instruments are used in many orientations and positions, and these terms are not intended to be limiting and absolute.

As can be further seen in FIGS. 1 and 2, an embodiment of the flexible interface support assembly 10 may include a surgical tool docking assembly 50 that may be operably attached to a stand 30. The stand 30 may comprise a conventional stand that includes a base 32 that has a vertical support bar 34 protruding therefrom. The base 32 may include lockable wheels or casters 33 to facilitate movement of the stand 30. In other embodiments, the stand may comprise an immovable fixture. The vertical support bar 34 of the stand 30 may include a telescopic locknut arrangement 35 to enable the clinician to adjust the vertical height of the mounting assembly 50 to a convenient working height. A flexible "gooseneck" mounting tube 36 may be attached to the top of the vertical support bar 34 and may be selectively positionable in a variety of convenient orientations. Those of ordinary skill in the art will appreciate that the gooseneck mounting tube 36 may be selectively oriented in a variety of different positions/configurations to enable a surgical instrument to be advantageously clamped or otherwise attached thereto as will be explained in further detail below. Such stands are known in the art and, as such, details concerning the specific construction of stand 30 will not be provided herein. For example, those stands manufactured by Anthro of 10450 SW Manhasset Dr., Tualatin, Oreg. under Model No. POC-Cart may be successfully employed. However, those of ordinary skill in the art will understand that the various mounting assembly embodiments of the present invention may be effectively employed with other types of conventional stands without departing from the spirit and scope of the present invention.

Various embodiments of the mounting assembly 50 may include a central cross bar 52 that may be clamped onto or otherwise fastened to the vertical support bar 34 as shown in FIGS. 1, 1A, and 2. It will be further understood, however, that the central cross bar 52 could be attached to a host of other structures in the surgical suite such as the gooseneck mounting tube 36, a table, a bed, etc., without departing from the spirit and scope of the present invention. In various embodiments, the mounting assembly 50 may include a first tool docking station generally depicted as 70 and a second tool docking station, generally depicted as 90. The first tool docking station 70 may be operably attached to a right end 54 of the central cross bar 52 and the second tool docking station may be mounted to the left end 56 of the central cross bar 52. As will be discussed in further detail below, the second tool docking station 90 may be a substantially identical "mirror image" of the first tool docking station 70.

Figure 5:
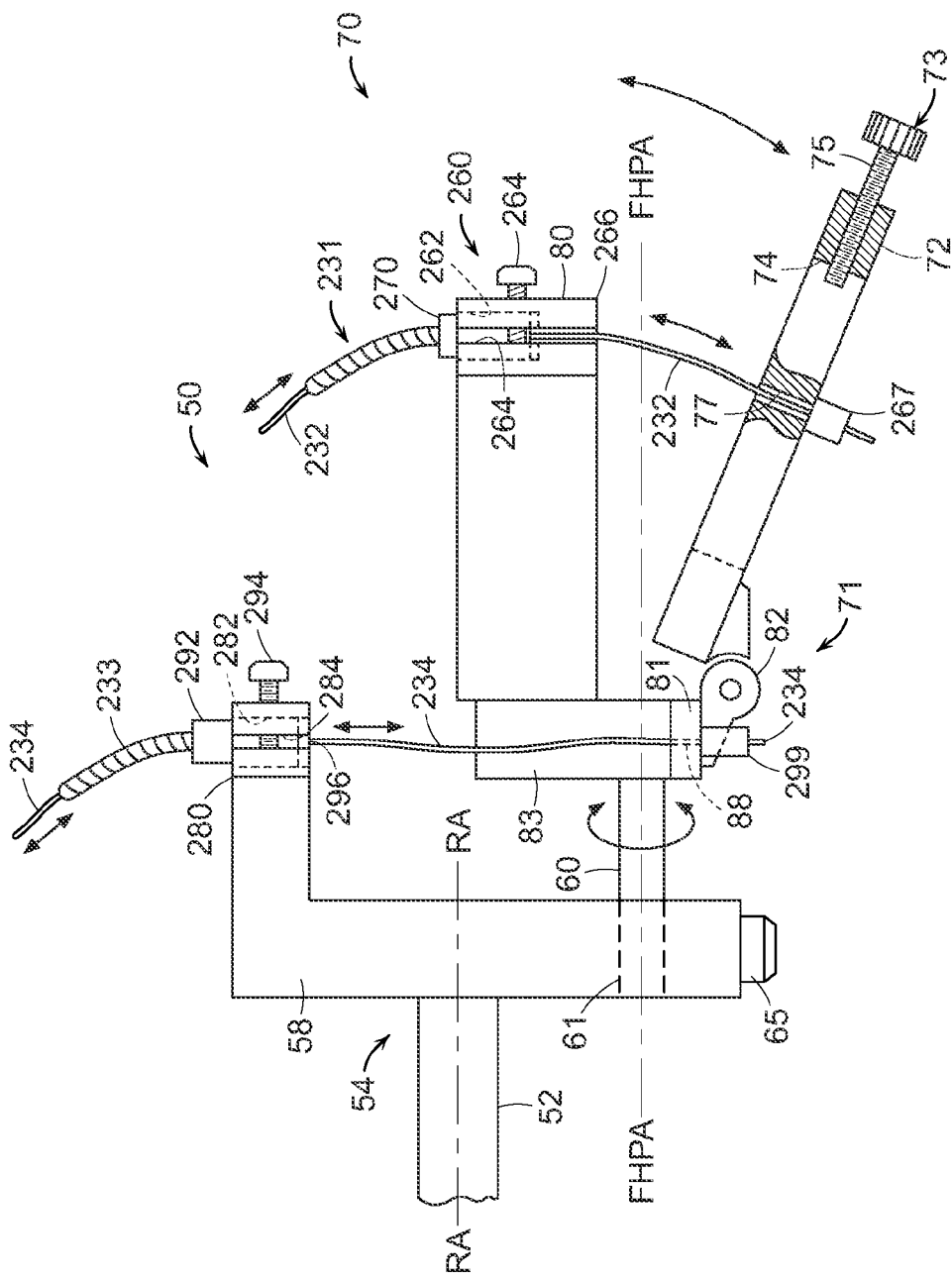
FIG. 5 is a top view of a first tool docking station portion of the surgical tool docking assembly of FIGS. 3 and 4.
Figure 5A:
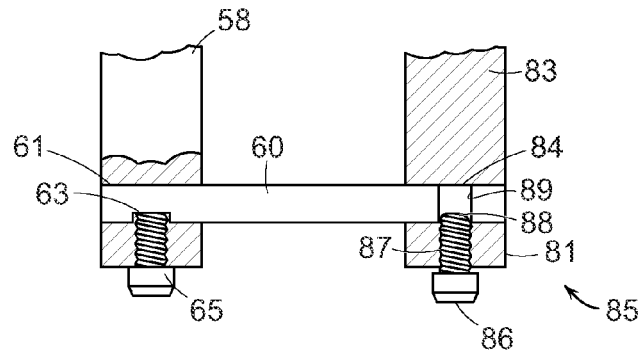
FIG. 5A is a cross-sectional view of a portion of a first tool docking station illustrating a first friction brake assembly embodiment of the present invention.

The mounting assembly 50 may comprise a first tool docking station 70 that is mounted for selective movement relative to the central crossbar 52. In various embodiments, a first L-shaped bracket 58 may be attached to the right end 54 of the central crossbar 52. See FIGS. 2 and 5. A first tool mounting bracket 80 may be attached to the first L-shaped bracket 58 by a first pivot bar 60. First pivot bar 60 facilitates selective pivotal travel of the first tool mounting bracket 80 and ultimately the first tool docking station 70 relative to the central crossbar 52 about a first horizontal pivot axis FHPA-FHPA. As can be seen in FIGS. 5 and 5A, the first L-shaped bracket 58 has a hole 61 therethrough for receiving a portion of the first pivot bar 60 therein. The first pivot bar 60 may have a flat surface 63 thereon for engagement with a setscrew 65 as shown in FIG. 5A. The setscrew 65 serves to prevent the first pivot bar 60 from rotating relative to the first L-shaped bracket 58.

Various embodiments may further employ a first horizontal friction brake assembly, generally designated as 85, for controlling the selective pivotal travel of the first tool docking station 70 about the first horizontal pivot axis FHPA-FHPA defined by the first pivot bar 60. As can be seen in FIGS. 5 and 5A, the first tool mounting bracket 80 has a body portion 83 that has a hole 84 for rotatably receiving another end portion of the first pivot bar 60 therein. Thus, the hole 84 is sized relative to the first pivot bar 60 to enable the first pivot bar 60 to rotate therein. In some embodiments, the first friction brake assembly 85 comprises a setscrew 86 that is threaded through a tapped hole 87 in a first vertical mounting plate portion 81 of the first tool mounting bracket 80. See FIG. 5A. The setscrew 86 has a ball 88 on its end that is sized to extend into a groove 89 in the first pivot bar 60. Such arrangement prevents the body portion 83 from translating along the length of the first pivot bar 60 while enabling the ball end 88 of the setscrew 86 to establish a desired amount of frictional engagement with the first pivot bar 60 such that the first tool mounting bracket 80 (and ultimately the first tool docking station 70) is able to rotate about the first pivot bar 60 upon the application of a first amount of pivotal motion to the first tool docking station 70, yet be retained in a desired position after the clinician discontinues the application of the first amount of pivotal motion. Other methods and arrangements for establishing an amount of frictional or braking force between the first tool mounting bracket 80 and the first pivot bar 60 may also be employed. For example, the first friction brake assembly may employ springs, detent arrangements, etc., without departing from the spirit and scope of the present invention.

The first tool docking station 70 may further include a first vertical friction brake assembly, generally designated as 71 for controlling pivotal travel of a first tool docking plate 72 of the first tool docking station 70 about a first vertical axis FVA-FVA. In some embodiments, for example, the first vertical friction brake assembly 71 may comprise a conventional first friction hinge 82 that couples the first tool docking plate 72 to the first tool mounting bracket 80. In particular, the first friction hinge 82 is attached to the first vertical mounting plate portion 81. First friction hinge 82 facilitates selective pivotal travel of the first tool docking plate 72 about the first vertical axis FVA-FVA relative to the first tool mounting bracket 80. For example, those friction hinges manufactured by Reell of 1259 Willow Lake Boulevard, St. Paul Minn. 55110-5103 under Model No. PHC Hinge may be successfully employed. Thus, such arrangement enables the first tool docking station 70 to be selectively pivoted about the first vertical pivot axis FVA-FVA that extends substantially transverse to the first horizontal pivot axis FHPA-FHPA upon application of a second amount of pivotal motion to the first tool docking station and retain the first tool docking station 70 in a desired position about the first vertical pivot axis FVA-FVA when the application of the second amount of pivotal motion to the first tool docking station 70 has been discontinued.

The first tool docking plate 72 is preferably configured to be removably affixed to a first surgical instrument 20. In various embodiments for example, a docking hole 74 may be provided through the first tool docking plate 72 for receiving a portion of the first surgical instrument 20 therethrough. In the embodiment depicted in FIG. 1A, four first docking screws 73 are provided through the first tool docking plate 72 such that the screws 73 are oriented 90 degrees from each other to engage and capture a portion of the first surgical instrument 20 therebetween to removably mount the first surgical instrument 20 to the first tool docking plate 72. At least one, and preferably two, first docking screws 73 may comprise first set screws 75 to enable the clinician to rotate them without the use of tools. See FIG. 1A. Thus, to couple the first surgical instrument 20 to the first docking plate 72, the clinician simply inserts a portion of the first surgical instrument 20 through the hole 74 in the docking plate 72 and then tightens the first set screws 75 in position. Those of ordinary skill in the art will understand, however, that the first tool docking plate 72 may be advantageously configured to retainingly engage a portion of the first surgical instrument 20 so that the first surgical instrument 20 is removably affixed to the first tool docking station 70. For example, the first surgical instrument 20 may be permanently affixed to the first tool docking station 70 by other forms of latches, clamps, etc.

Figure 6:
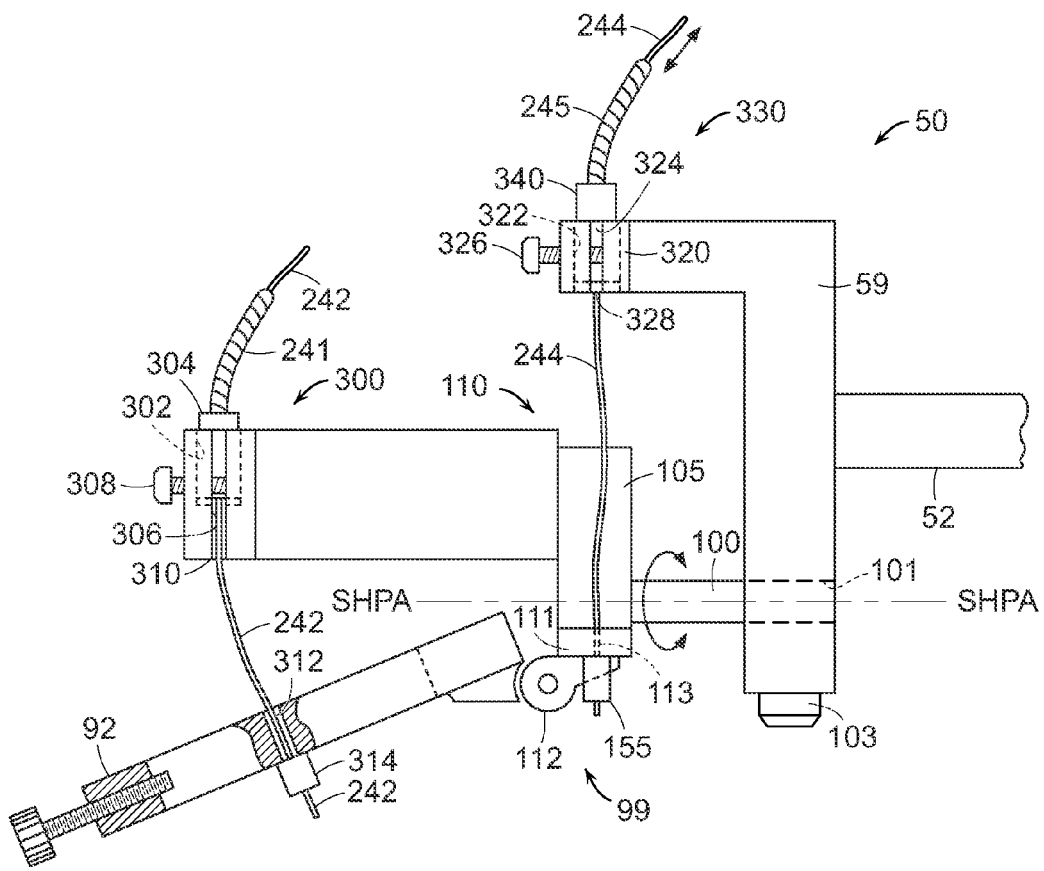
FIG. 6 is a top view of a second tool docking portion of the surgical tool docking assembly of FIGS. 3 and 4.
Figure 6A:
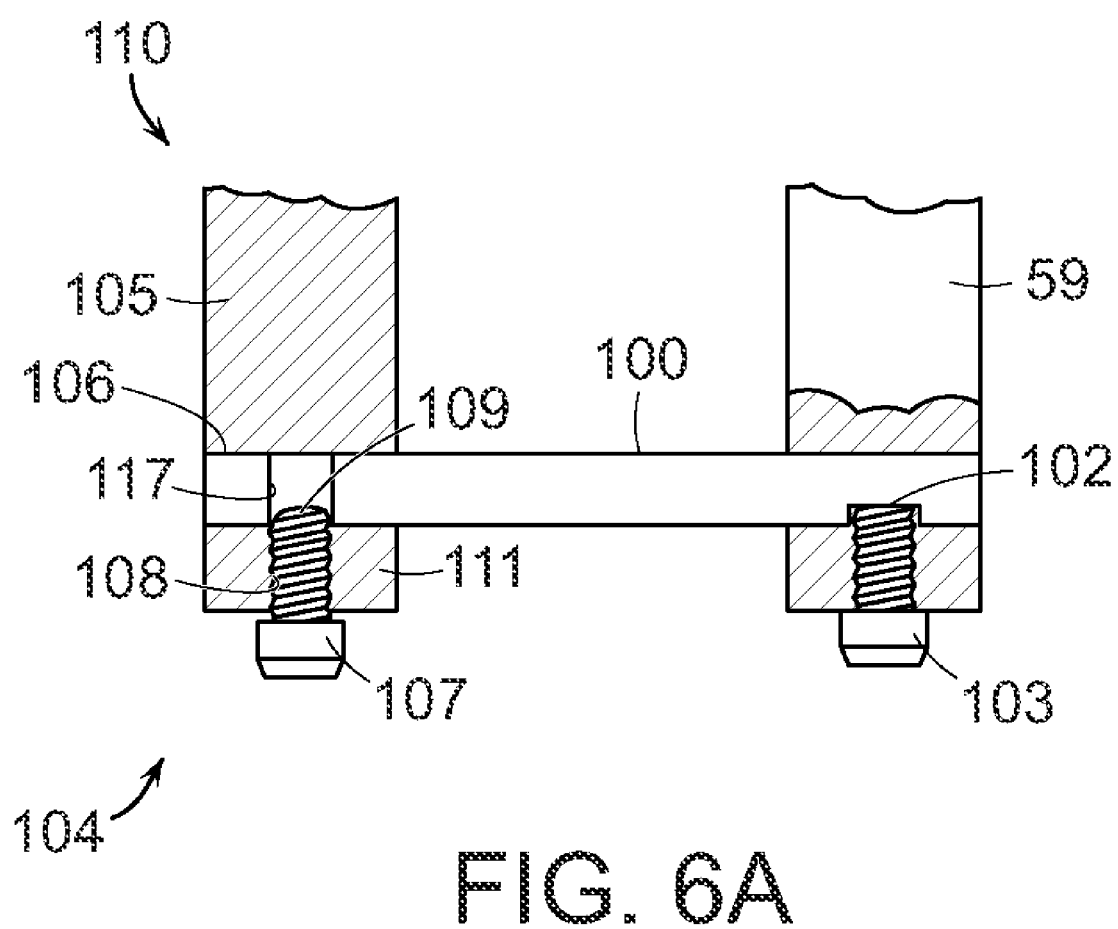
FIG. 6A is a cross-sectional view of a portion of a second tool docking station illustrating a second friction brake assembly embodiment of the present invention.

As indicated above and depicted in FIG. 1, the flexible user interface support assembly 10 may be advantageously employed with a second surgical instrument 20' that may be identical in construction to the first surgical instrument 20 or the second surgical instrument 20' may comprise an entirely different surgical instrument used to perform entirely different surgical procedures. In this embodiment, the mounting assembly 50 also includes a second tool docking station generally depicted as 90 that may be substantially identical to the first tool docking station 70 and be configured to operably support a second surgical instrument 20'. In various embodiments, a second L-shaped bracket 59 may be attached to the left end 57 of the central crossbar 52. See FIGS. 2 and 6. A second tool mounting bracket 110 may be attached to the second L-shaped bracket 59 by a second pivot bar 100. Second pivot bar 100 facilitates selective pivotal travel of the second tool mounting bracket 110 and ultimately the second tool docking station 90 relative to the central crossbar 52 about a second horizontal pivot axis SHPA-SHPA. In various embodiments, the first horizontal pivot axis FHPA-FHPA may be substantially coaxial with the second horizontal pivot axis SHPA-SHPA and essentially comprise one horizontal pivot axis. As can be seen in FIGS. 6 and 6A, the second L-shaped bracket 59 has a hole 101 therethrough for receiving a portion of the second pivot bar 100 therein. The second pivot bar 100 may have a flat surface 102 thereon for engagement with a setscrew 103 as shown in FIG. 6A. The setscrew 013 serves to prevent the second pivot bar 100 from rotating relative to the second L-shaped bracket 59.

Various embodiments may further employ a second horizontal friction brake assembly, generally designated as 104, for controlling the selective pivotal travel of the second tool docking station 90 about the second horizontal pivot axis SHPA-SHPA defined by the second pivot bar 100. As can be seen in FIGS. 6 and 6A, the second tool mounting bracket 110 has a body portion 105 that has a hole 106 for rotatably receiving another end portion of the second pivot bar 100 therein. Thus, the hole 106 is sized relative to the second pivot bar 100 to enable the second pivot bar 100 to rotate therein. In some embodiments, the second friction brake assembly 104 comprises a setscrew 107 that is threaded through a tapped hole 108 in a second vertical mounting plate portion 111 of the second tool mounting bracket 59. The setscrew 107 has a ball portion 109 that is sized to extend into a groove 117 in the second pivot bar 100. See FIG. 6 A. Such arrangement prevents the body portion 105 from translating along the length of the second pivot bar 100 while enabling the ball portion 109 of the setscrew 107 to establish a desired amount of frictional engagement with the second pivot bar 100 such that the second tool mounting bracket 110 (and ultimately the second tool docking station 90) is able to rotate about the second pivot bar 100 upon the application of a third amount of pivotal motion to the second tool docking station 90, yet be retained in a desired position after the clinician discontinues the application of the third amount of pivotal motion. Other methods and arrangements for establishing an amount of frictional or braking force between the second tool mounting bracket 110 and the second pivot bar 100 may also be employed. For example, the second friction brake assembly may employ springs, detent arrangements, etc., without departing from the spirit and scope of the present invention.

The second tool docking station 90 may further include a second vertical friction brake assembly, generally designated as 99 for controlling pivotal travel of a second tool docking plate 92 of the second tool docking station 90 about a second vertical axis SVA-SVA. In some embodiments, for example, the second vertical friction brake assembly 99 may comprise a conventional second friction hinge 112 that couples the second tool docking plate 92 to the second tool mounting bracket 110. In particular, the second friction hinge 112 is attached to a second vertical mounting plate 111 that is attached to the second tool mounting bracket 110. Second friction hinge 112 facilitates selective pivotal travel of the second tool docking plate 92 about a second vertical axis SVA-SVA relative to the second tool mounting bracket 110. Thus, such arrangement enables the second tool docking station 90 to also be selectively pivoted about the second horizontal pivot axis SHPA-SHPA that extends substantially transverse to the second horizontal pivot axis SHPA-SHPA upon application of a fourth amount of pivotal motion to the second tool docking station 90 and retain the second tool docking station 90 in a desired position about the second vertical pivot axis SVA-SVA when the application of the fourth amount of pivotal motion to the second tool docking station 90 has been discontinued.

The second tool docking plate 92 is also preferably configured to be removably affixed to a surgical tool 20'. In various embodiments for example, a docking hole 94 may be provided through the second docking plate 92 for receiving a portion of the surgical instrument 20 therethrough. Four second docking screws 93 are provided through the second tool docking plate 92 that are oriented 90 degrees from each other to engage and capture a portion of the surgical instrument 20' therebetween to removably mount the surgical instrument 20' to the second tool docking plate 92. At least one and preferably two first docking screws 93 may comprise second set screws 95 to enable the clinician to rotate them without the need of tools.

To couple the second surgical instrument 20' to the second tool docking plate 92, the clinician simply inserts a portion of the second surgical instrument 20' through the hole 94 in the second tool docking plate 92 and then tightens the second set screws 95 in position. Those of ordinary skill in the art will understand, however, that the second tool docking plate 92 may be advantageously configured to retainingly engage a portion of the second surgical instrument 20' so that the second surgical instrument 20' is removably affixed to the second tool docking station 90. For example, the second surgical instrument 20' may be removably affixed to the second tool docking station 90 by other forms of latches, clamps, etc. In various embodiments, the tool docking assembly may be manufactured from steel, aluminum, stainless steel, or plastic and may be of welded construction or the various bracket portions thereof may comprise separate components that are interconnected with suitable fasteners such as screws, bolts etc.

The flexible user interface support assembly 10 may be advantageously employed with a cable-controlled, steerable guide tube assembly 200 which may be supported, for example, by the gooseneck mounting tube 36. Various forms of steerable guide tube assemblies are known. For example, the various embodiments of the present invention may be successfully used in connection with various cable actuated manipulatable guide systems disclosed in U.S. patent application Ser. No. 12/468,462, filed May 19, 2009, entitled "MANIPULATABLE GUIDE SYSTEM AND METHODS FOR NATURAL ORIFICE TRANSLUMENAL ENDOSCOPIC SURGERY", the disclosure of which is herein incorporated by reference in its entirety.

Figure 7:
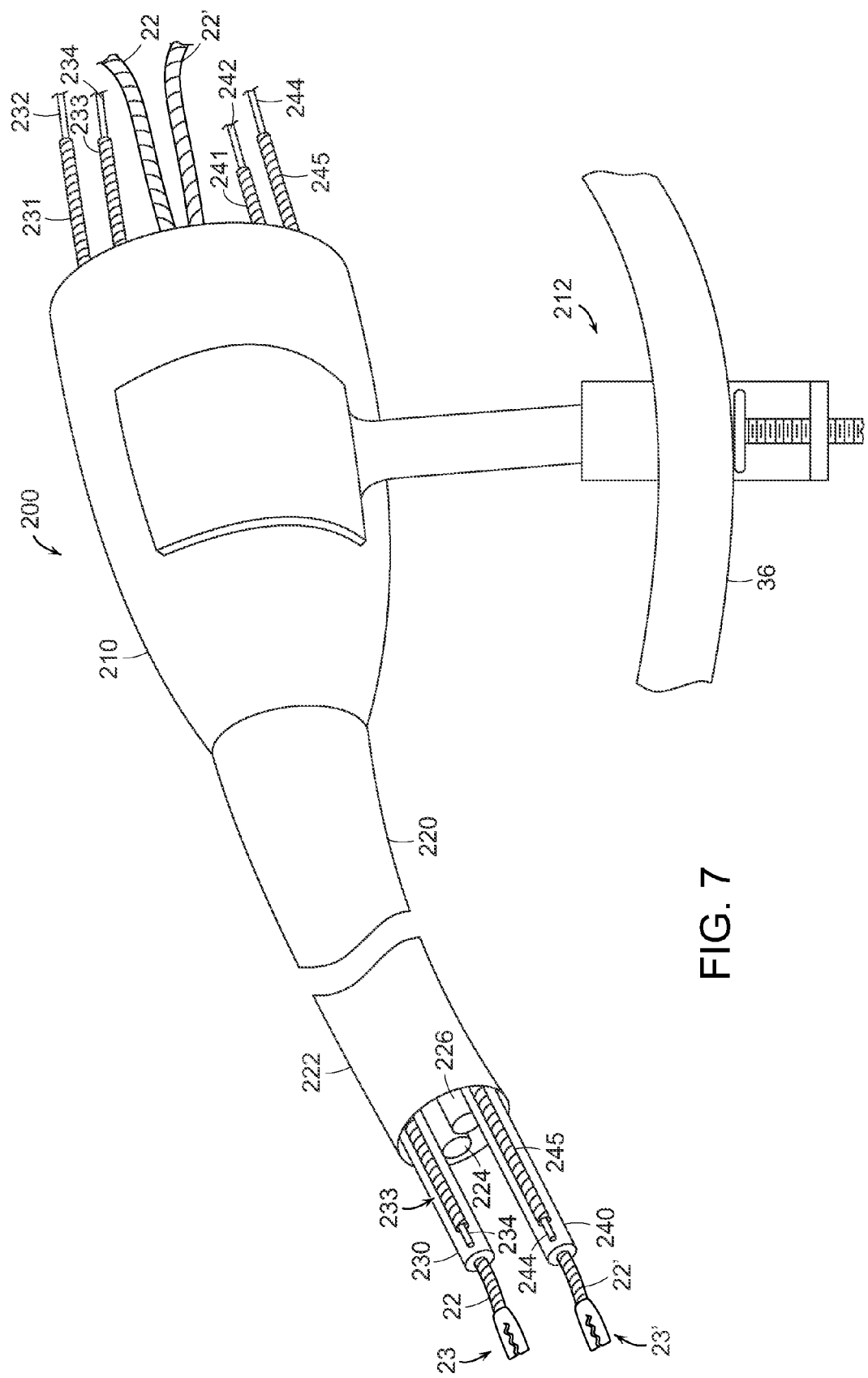
FIG. 7 is a partial perspective view of an embodiment of a cable-controlled steerable guide tube assembly.
Figure 8:
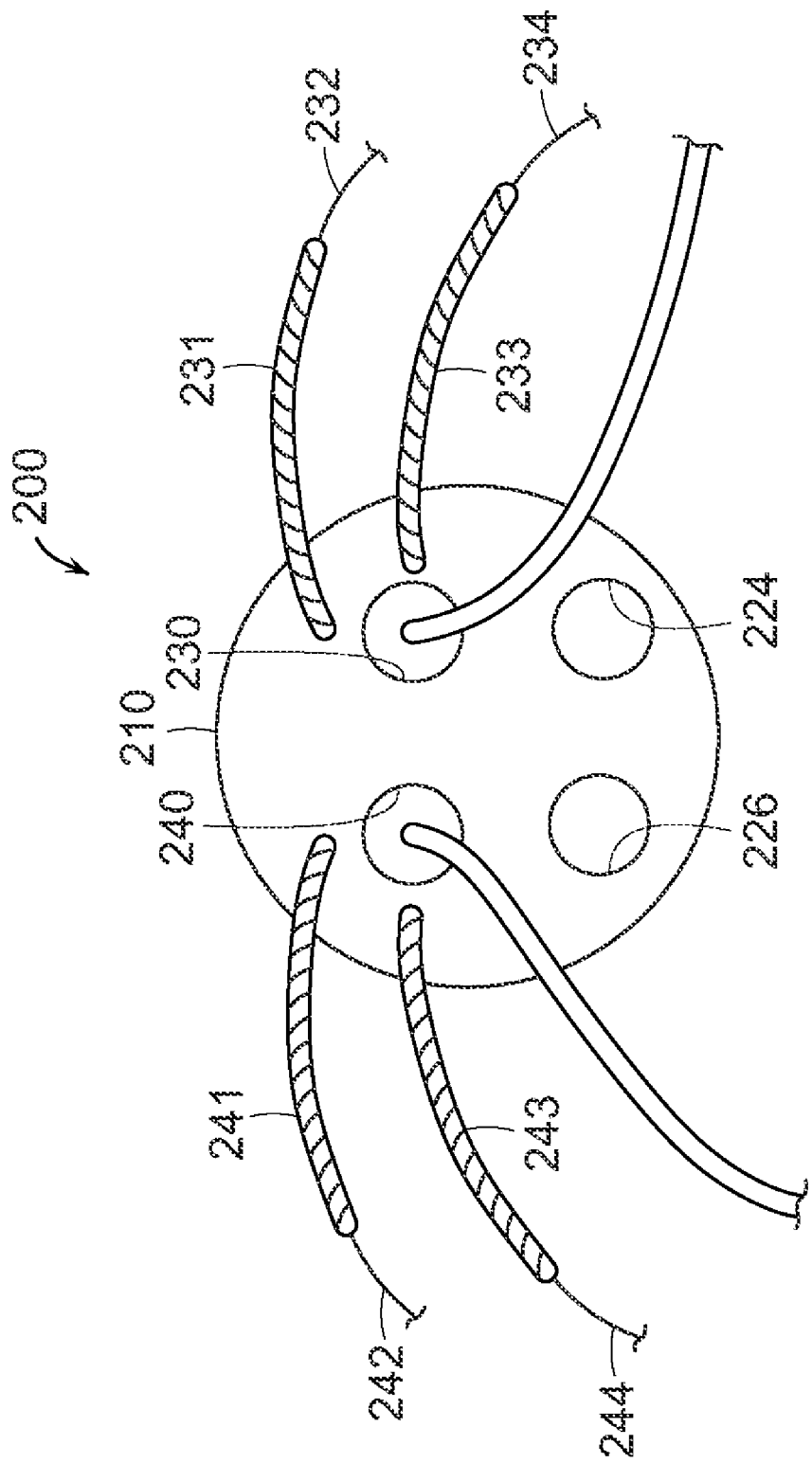
FIG. 8 is an end view of a portion of the cable-controlled steerable guide tube assembly depicted in FIG. 7.

As can be seen in FIGS. 1 and 7, the steerable guide tube assembly 200 may comprise a handle portion 210 that may be clamped or otherwise attached to the gooseneck mounting tube 36 by a clamp 212 that facilitates removal and repositioning of the handle 210 on the gooseneck mounting tube 36. An inner sheath assembly 220 is attached to and protrudes from the handle 210 for insertion into the patient, through, for example, a natural orifice or other access opening made in the patient. As discussed in the aforementioned patent application, the inner sheath assembly 220 may comprise an inner sheath 222 that supports at least one and preferably a plurality of working channels 230, 240 therein. For example, in the embodiment depicted in FIG. 6, the inner sheath 222 supports a selectively positionable right working channel 230 and a selectively positionable left working channel 240 therein. The inner sheath 222 may also support various other working channels 224, 226, etc. therein that may be selectively positionable or may simply comprise flexible lumens supported within the inner sheath assembly 222. In use, for example, a flexible working portion 22 of the surgical instrument 20 may extend through one of the working channels 230, 240 such that the distal tip 23 thereof may be selectively positioned within the patient by steering the working channel through which it extends. See FIG. 7. Similarly, the flexible working portion 22' of the surgical instrument 20' may extend through one of the working channels 230, 240 such that the distal tip 23' thereof may be selectively positioned within the patient by steering the working channel through which it extends.

By way of example, however, in various embodiments, the right working channel 230 is controlled by a first "left/right" articulation cable 232 and a first "up/down" articulation cable 234. The first left/right articulation cable 232 may extend through a flexible cable sheath or coil tube 231 that extends through the inner sheath assembly 222 and the first up/down articulation cable 234 may extend through a flexible coil tube or cable sheath 233 that extends within the inner sheath assembly 222. In various embodiments, the first left/right articulation cable 232 is sized relative to the flexible coil tube 231 such that it is freely movable therein. Similarly, the first up/down cable 234 is sized relative to the flexible coil tube 233 such that it is freely movable therein. Also in various embodiments, the left working channel 240 is controlled by a "left/right" articulation cable 242 that is received within a flexible cable sheath or coil tube 241 that extends through the inner sheath assembly 222. The second left/right articulation cable 242 is sized relative to the flexible coil tube 241 such that it is freely movable therein. The left working channel 240 may be further controlled by an "up/down" articulation cable 244 that is received in a flexible cable sheath or coil tube 245 that extends through the inner sheath assembly 222. The second up/down articulation cable 244 is sized relative to the coil tube 245 such that it is freely movable therein. In various embodiments, the articulation cables 232, 234, 242, 244 and their respective coil tubes 232, 233, 241, 243 extend proximally out through the handle portion 210 of the steerable guide tube assembly 200 and are adapted to be coupled to the user interface support assembly 10 to enable the selectively positionable right and left working channels 230 and 240 to be moved automatically in response to the manipulation of the surgical instruments 20, 20', respectively.

Various embodiments of the present invention may employ quick-connection arrangements for coupling the cables 232, 234, 242, 244 and their respective coil tubes 231, 233, 241, 243 to the mounting assembly 50. Various methods for attaching the first articulation cables 232 and 234 to the mounting assembly 50 are depicted in FIG. 5. As can be seen in that Figure, the first left/right articulation cable 232 and its coil tube 231 may be operably coupled to the mounting assembly 50 by a first cable attachment assembly generally designated as 260. The first cable attachment assembly 260 may comprise a bore 262 that is provided in the first tool mounting bracket 80 and is sized to receive therein a ferrule 270 that is attached to the coil tube 231 of the first left/right articulation cable 232. The first tool mounting bracket 80 may further have a slit 264 that extends into the bore 262 such that when the ferrule 270 is inserted into the bore 262, it can be retained therein by a set screw 264. The first left/right articulation cable 232 passes through a smaller diameter hole 266 in the first tool mounting bracket 80 and is inserted through a hole 77 in the first tool docking plate 72. The end of the first left/right articulation cable 232 is affixed to the first tool docking plate 72 by a tube segment 267 that is crimped onto or otherwise affixed to the end of the cable 232 and which has a diameter that is larger than hole 73 in the tool docking plate 72. Thus, by pivoting the first tool docking plate 72 about the first vertical axis FVA-FVA, the clinician can actuate the first left/right articulation cable 232 to cause the first working channel 230 to articulate in a left or right direction depending upon whether the cable 232 is being pushed through the coil tube 231 or pulled through the coil tube 231. In particular, when the clinician pivots the first surgical tool 20 and the first tool docking plate 72 about the first vertical axis FVA-FVA in a direction towards the first tool docking bracket 80, the first left right articulation cable is pushed through the coil tube 231 and the distal end of the first working channel 230 is articulated to a "first" or left direction. When the clinician moves the first surgical tool 20 and the first tool docking plate 72 away from the first tool docking bracket 80, the first left/right articulation cable 232 is pulled through the coil tube 231 and the distal end of the first working channel is articulated to a "second" or right direction.

Also in various embodiments, the first up/down articulation cable 234 is attached to the first tool mounting bracket 80 and a first cable standoff plate 280 that is attached to the first L-shaped bracket 58 by a second cable attachment assembly generally designated as 290. The second cable attachment assembly 290 may comprise a bore 282 that is provided in the first cable standoff plate 280 and is sized to receive therein a ferrule 292 that is attached to the outer sheath 233 of the first up/down articulation cable 234. The first cable standoff plate 280 may further have a slit 284 that extends into the bore 282 such that when the ferrule 292 is inserted into the bore 282, it can be retained therein by a set screw 294. The cable 234 passes through a smaller diameter hole 296 in the first cable standoff plate 280 and is inserted through a hole 88 in the first vertical mounting plate 81. The end of the cable 234 is affixed to the first vertical mounting plate 81 by a tube segment 299 that is crimped onto or otherwise affixed to the end of the cable 234 and which has a diameter that is larger than hole 88 in the first vertical mounting plate 81. Thus, by pivoting the first mounting bracket 80 and the first vertical mounting plate 81 attached thereto about pivot axis PA-PA, the clinician can actuate the first up/down cable 234 to cause the distal end of the first working channel 230 to articulate up and down depending upon whether the cable 234 is being pushed through the coil tube 233 or pulled through the coil tube 233. For example, when the clinician pivots first surgical tool 20 and the first tool docking plate 72 in a direction towards the steerable guide tube assembly 200 about the horizontal pivot axis HPA-HPA, the first up/down articulation cable 234 is pushed through the coil tube 233 which causes the distal end of the first working channel to pivot downward. Likewise, when the clinician pivots the first surgical tool 20 and the first tool docking plate 72 away from the steerable guide tube assembly 200 about horizontal pivot axis HPA-HPA, the distal end of the first working channel 230 is articulated in an upward direction.

Figure 3:
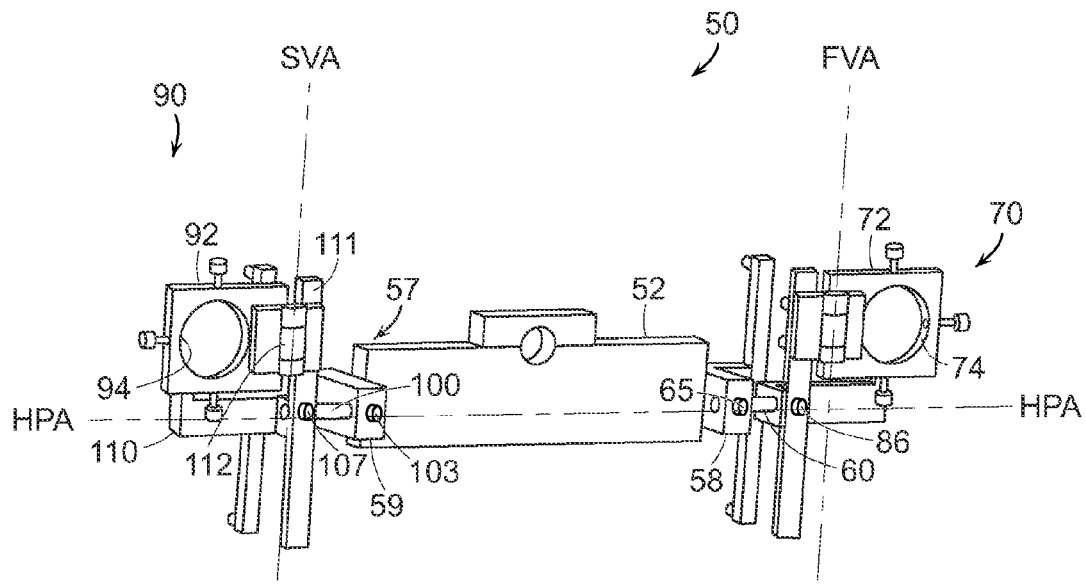
FIG. 3 is a front perspective view of a surgical tool docking assembly embodiment of the present invention.
Figure 4:
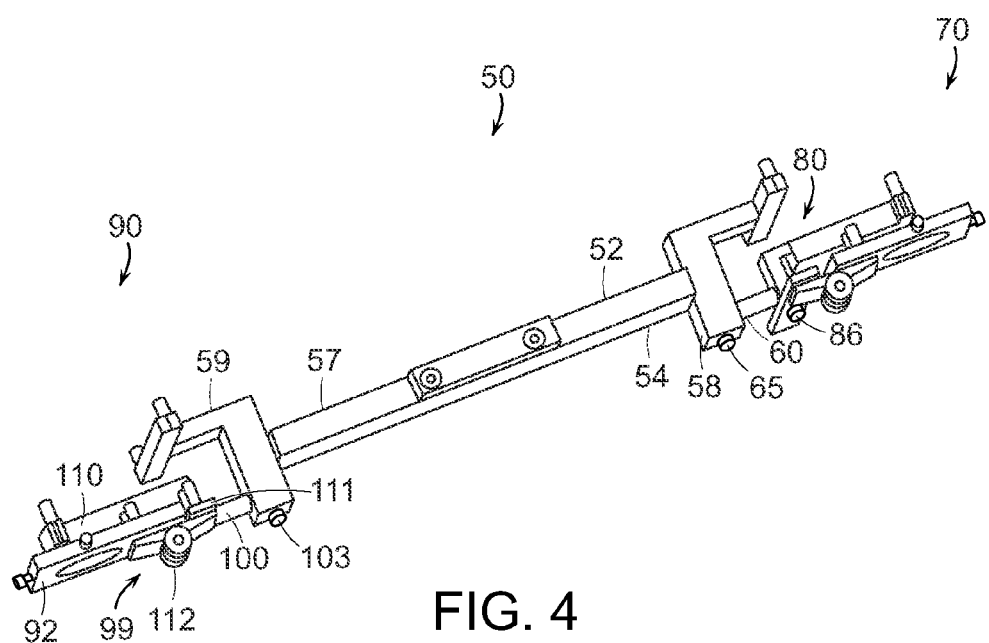
FIG. 4 is a top view of the a surgical tool docking assembly of FIG. 3.

As can be seen in FIG. 6, the second left/right articulation cable 242 and its coil tube 241 may be operably coupled to the mounting assembly 50 by a third cable attachment assembly generally designated as 300. The third cable attachment assembly 300 may comprise a bore 302 that is provided in the second tool mounting bracket 110 and is sized to receive therein a ferrule 304 that is attached to the coil tube 241 of the second left/right articulation cable 242. The second tool mounting bracket 110 may further have a slit 306 that extends into the bore 302 such that when the ferrule 304 is inserted into the bore 302, it can be retained therein by a set screw 308. The second left/right articulation cable 242 passes through a smaller diameter hole 310 in the second tool mounting bracket 110 and is inserted through a hole 312 in the second tool docking plate 92. The end of the second left/right articulation cable 242 is affixed to the second tool docking plate 92 by a tube segment 314 that is crimped onto or otherwise affixed to the end of the cable 242 and which has a diameter that is larger than hole 312 in the second tool docking plate 92. Thus, by pivoting the second tool docking plate 92 about the second vertical axis SVA-SVA (FIG. 3), the clinician can actuate the second left/right articulation cable 242 to cause the second working channel 240 to articulate in a left or right direction depending upon whether the cable 242 is being pushed through the coil tube 241 or pulled through the coil tube 241. In particular, when the clinician pivots the second surgical tool 20' which, in turn, pivots the second tool docking plate 92 about the second vertical axis SVA-SVA in a direction towards the second tool docking bracket 110, the second left/right articulation cable 242 is pushed through the coil tube 241 and the distal end of the second working channel 240 is articulated to a "third" or left direction. When the clinician moves the second surgical tool 20' and the second tool docking plate 92 away from the second tool docking bracket 110, the second left/right articulation cable 242 is pulled through the coil tube 241 and the distal end of the second working channel 240 is articulated to a "fourth" or right direction.

Also in various embodiments, the second up/down articulation cable 244 is attached to the second tool mounting bracket 110 and a second cable standoff plate 320 that is attached to the second L-shaped bracket 59 by a fourth cable attachment assembly generally designated as 330. The fourth cable attachment assembly 330 may comprise a bore 322 that is provided in the second cable standoff plate 320 and is sized to receive therein a ferrule 340 that is attached to the coil tube 245 of the second up/down articulation cable 244. The second cable standoff plate 320 may further have a slit 324 that extends into the bore 322 such that when the ferrule 340 is inserted into the bore 322, it can be retained therein by a set screw 326. The cable 244 passes through a smaller diameter hole 328 in the second cable standoff plate 320 and is inserted through a hole 113 in the second vertical mounting plate 111. The end of the cable 244 is affixed to the second vertical mounting plate 111 by a tube segment 115 that is crimped onto or otherwise affixed to the end of the cable 244 and which has a diameter that is larger than hole 113 in the second vertical mounting plate 111. Thus, by pivoting the second mounting bracket 110 and the second vertical mounting plate 111 attached thereto about horizontal pivot axis HPA-HPA, the clinician can actuate the second up/down articulation cable 244 to cause the distal end of the second working channel 240 to articulate up and down depending upon whether the cable 244 is being pushed through the coil tube 245 or pulled through the coil tube 245. For example, when the clinician pivots the second surgical tool 20' and the second tool docking plate 92 in a direction towards the steerable guide tube assembly 200 about the horizontal pivot axis HPA-HPA, the second up/down articulation cable 244 is pushed through the coil tube 245 which causes the distal end of the second working channel 240 to pivot downward. Likewise, when the clinician pivots the second surgical tool 20' and the second tool docking plate 92 away from the steerable guide tube assembly 200 about horizontal pivot axis HPA-HPA, the distal end of the second working channel 240 is articulated in an upward direction.

While the above-described embodiments are configured to support two endoscopic surgical instruments, those of ordinary skill in the art will understand that various embodiments of the present invention may be constructed to support a single instrument or more than two instruments. It will be further appreciated that depending upon how the cables are attached to the respective tool docking stations 70, 90, movement of the handle portions of the surgical instruments 20, 20' causes the cable controlled guide tube to impart laparoscopic-like movement of the distal tip of the flexible portion of the surgical instrument. For example, when the handle is lifted up, the cable controlled working channel through which the flexible working portion extends may move the tip portion downward or upward depending upon how the cables are coupled to the tool docking stations. Likewise, when the handle is moved left, the working channel may cause the distal tip to move left or right. It will be further appreciated that the unique and novel features of the various embodiments of the interface system 10 of the present invention enable the control cables for the cable controlled guide tube system to remain in any desired fixed position after the pivotal motions applied to the tool docking stations or the surgical instruments docked therein have been discontinued.

Figure 9:
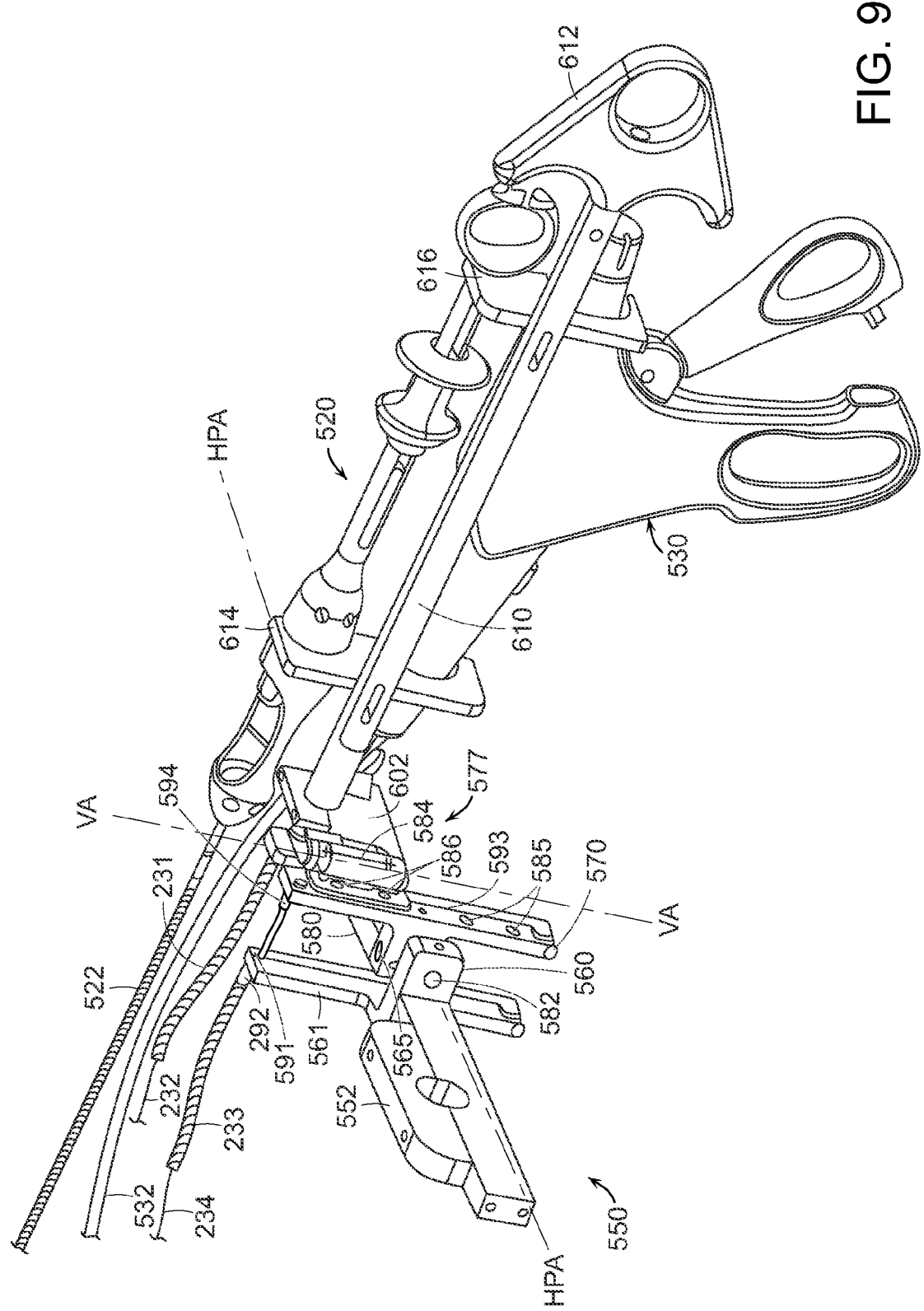
FIG. 9 is a perspective view of another flexible user interface support assembly embodiment of the present invention with the stand portion omitted for clarity.
Figure 10:
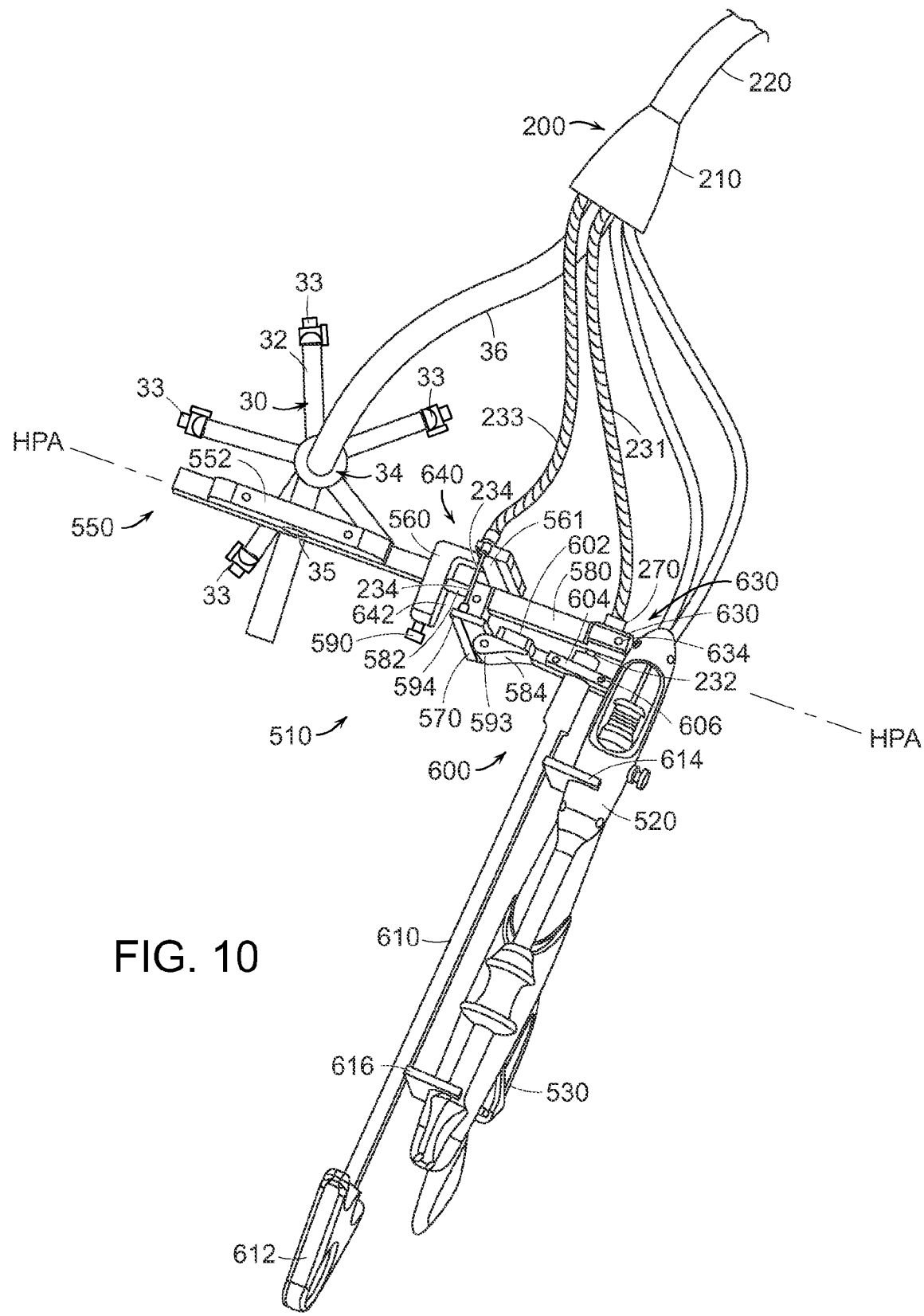
FIG. 10 is a top perspective view of the flexible user interface support assembly of FIG. 9, showing the stand portion.
Figure 11:
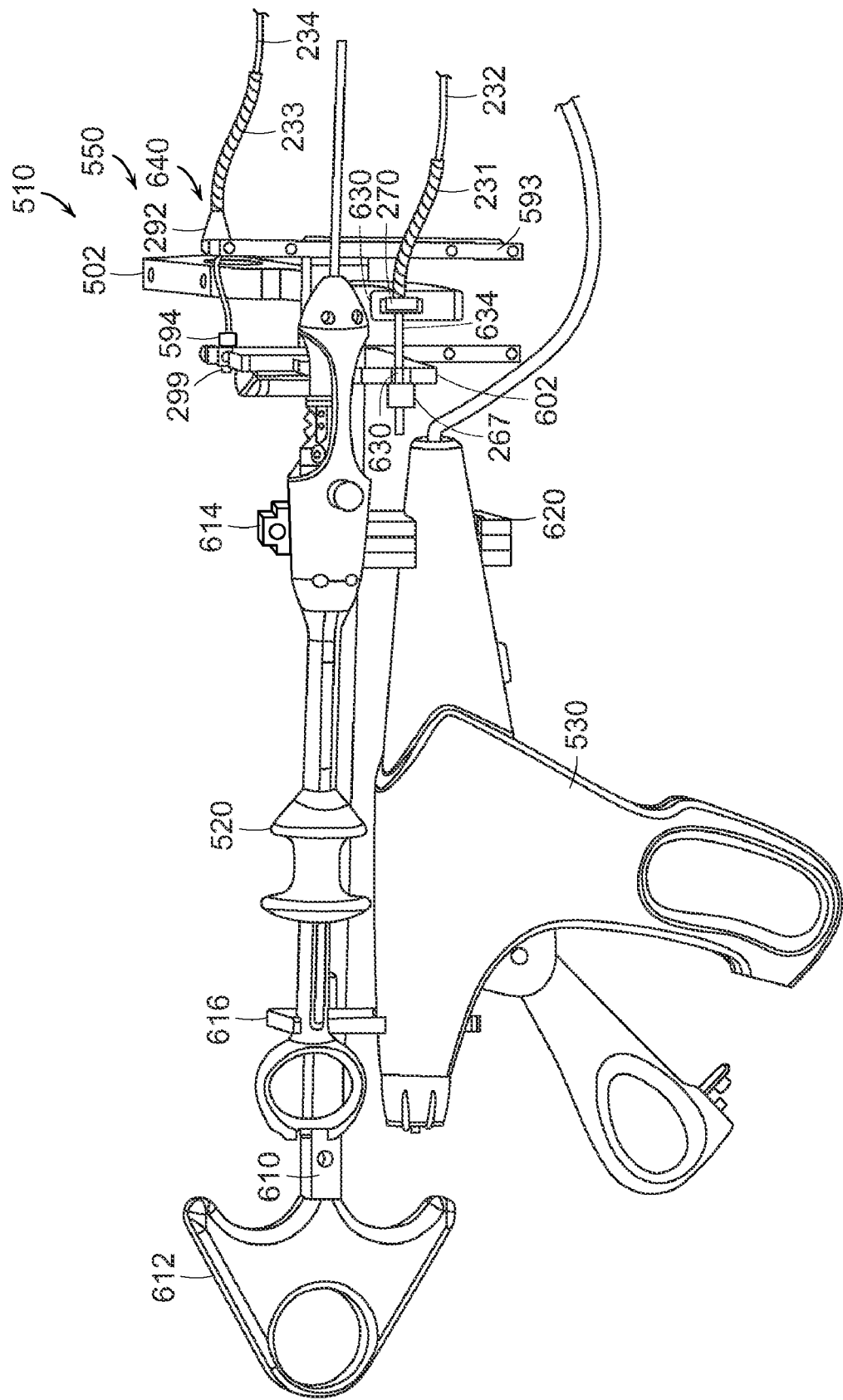
FIG. 11 is a side elevational view of the flexible user interface support assembly of FIG. 9.

FIGS. 9-11 depict another flexible interface support assembly 510 of the present invention that is adapted for use in connection with two endoscopic surgical instruments 520, 530. In the depicted embodiment, for example, surgical instrument 520 may comprise a conventional clip application device and surgical instrument 530 may comprise a conventional grasping device of the construction described above. One form of clip application device is disclosed in U.S. patent application Ser. No. 12/172,766, filed Jul. 14, 2008, and entitled TISSUE APPOSITION CLIP APPLICATION DEVICES AND METHODS, the disclosure of which is herein incorporated by reference in its entirety. Other forms of surgical instruments may be effectively employed with the various embodiments of the present invention disclosed herein. Other of such instruments are disclosed for example in U.S. patent application Ser. No. 12/133,109, filed Jun. 4, 2008, entitled "ENDOSCOPIC DROP OFF BAG"; U.S. patent application Ser. No. 11/610,803, entitled "MANUALLY ARTICULATING DEVICES"; and U.S. patent application Ser. No. 12/170,126, entitled "DEVICES AND METHODS FOR PLACING OCCLUSION FASTENERS", the respective disclosures of which are herein incorporated by reference in their entireties.

Various embodiments of the flexible user interface support assembly 510 may include a stand mounting bracket 550 that may be attached to a stand 30 of the type and construction described above. The stand mounting bracket 550 may include a clamp portion 552 that can be removably clamped onto a horizontal mounting rod 35 attached to the stand 30. See FIG. 10. However, other clamping and fastener arrangements may be employed to affix the stand mounting bracket 550 to the stand 30 without departing from the spirit and scope of the present invention. As can be seen in FIGS. 9-11, a first, L-shaped cable mounting bracket 560 may be attached to the stand mounting bracket 550. The first cable mounting bracket 560 may include a vertically extending section 561 to enable a first cable outer jacket end ferrule 292 to be mounted thereto.

Figure 9A:
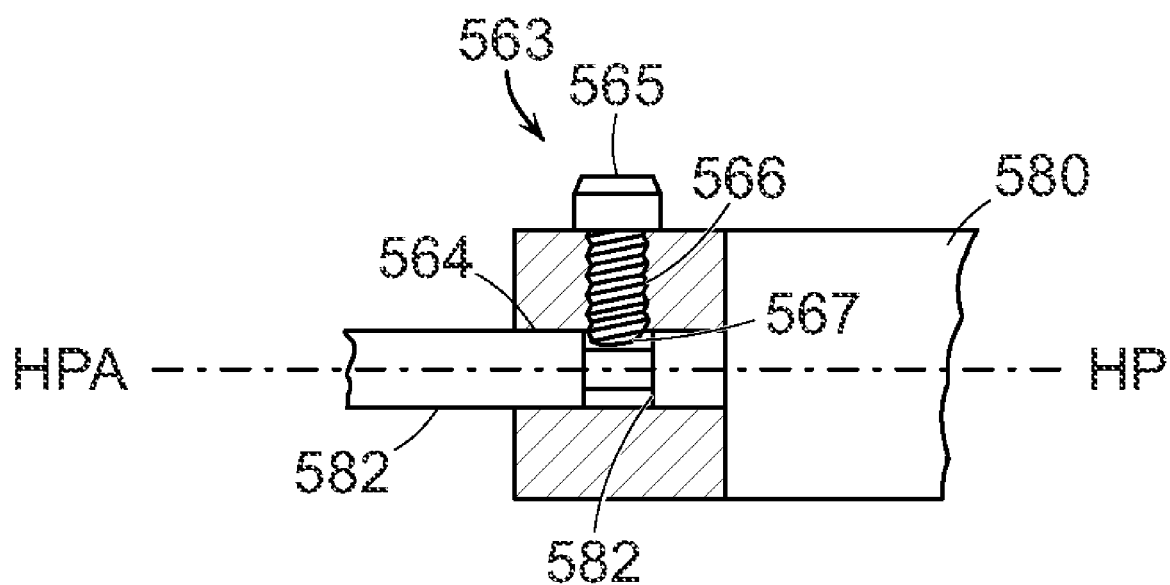
FIG. 9A is a cross-sectional view of a portion of a second cable mounting bracket illustrating a friction brake assembly embodiment of the present invention.

As can be further seen in FIGS. 9-11, a second substantially "T-shaped" cable mounting bracket 570 may be pivotally attached to a first cable mounting bracket 560 by a pivot rod 582 that facilitates pivotal travel of the second cable mounting bracket 570 (and a tool docking assembly 600 attached thereto) relative to the first cable mounting bracket 560 about a horizontal pivot axis HPA-HPA defined by pivot rod 582. The pivot rod 582 may be non-rotatably attached to the first cable mounting bracket 560 by a set screw 590. Various embodiments may also employ a friction brake assembly, generally designated as 563, for controlling the selective pivotal travel of the second cable mounting bracket 570 and the tool docking assembly 600 attached thereto about the horizontal pivot axis HPA-HPA. As can be seen in FIG. 9A, a hole 564 is provided through the second cable mounting bracket 570 for rotatably receiving another end portion of the pivot rod 582 therein. Thus, the hole 564 is sized relative to the pivot rod 582 to enable the pivot rod 582 to rotate therein. In some embodiments, the friction brake assembly 563 comprises a setscrew 565 that is threaded through a tapped hole 566 in the second cable mounting bracket 570. The setscrew 565 has a ball 567 thereon that is sized to extend into a groove 568 in the pivot rod 582. Such arrangement prevents the second cable mounting bracket 570 from translating along the length of the pivot rod 582 while enabling the ball end 567 of the setscrew 565 to establish a desired amount of frictional engagement with the pivot rod 582 such that the second cable mounting bracket 570 (and ultimately the tool docking assembly 600) is able to rotate about the pivot rod 582 upon the application of a first amount of pivotal motion to the tool docking assembly 600, yet be retained in a desired position after the clinician discontinues the application of the first amount of pivotal motion. Other methods and arrangements for establishing an amount of frictional or braking force between the second cable mounting bracket 570 and the pivot rod 582 may also be employed. For example, the first friction brake assembly may employ springs, detent arrangements, etc., without departing from the spirit and scope of the present invention.

Also in various embodiments, a third cable mounting bracket 591 may be connected to the first cable mounting bracket 560 to releasably trap the cable outer jacket ferrule 292 in a loose, pivotable manner while allowing cable 234 to translate freely therein. A fourth cable mounting bracket 593 may be mounted to the second cable mounting bracket 570 to pivotally lock the ferrule 594 at the end of the cable 234 between the second cable mounting bracket 570 and the fourth cable mounting bracket 593. When configured as described above, a downward pivoting of the tool 530 will cause the second cable mounting bracket 570 and fourth cable mounting bracket 593 to pivot about pin 582 and pull cable 234 within a locked outer jacket 233 to facilitate motion of the cable at the interface between the assembly 10 and cable controlled guide-tube system. Pivotable mounting of the outer cable jacket end ferrule 292 and cable end ferrule 594 allows use of a solid core cable without bending or kinking.

The tool docking assembly 600 may further include a vertical friction brake assembly, generally designated as 577 for controlling pivotal travel of the tool docking assembly 600 about a vertical axis VA-VA. In some embodiments, for example, the vertical friction brake assembly 577 may comprise a conventional friction hinge 584 that couples a tool mounting docking plate 602 to the second cable mounting bracket 570. In particular, the friction hinge 584 is attached to the second cable mounting bracket 570. In various embodiments, the second cable mounting bracket 570 may be provided with a plurality of threaded mounting holes 585 to accommodate fastening of a friction hinge 584 thereto to accommodate different surgical tool arrangements. Such arrangement enables the tool docking assembly 600 to be selectively pivoted about the vertical pivot axis VA-VA that extends substantially transverse to the horizontal pivot axis HPA-HPA upon application of a second amount of pivotal motion to the tool docking assembly 600 and retain the tool docking assembly 600 in a desired position about the vertical pivot axis VA-VA when the application of the second amount of pivotal motion to the tool docking assembly 600 has been discontinued.

Various embodiments of the tool docking assembly 600 may include a input shaft 610 that is attached to the tool docking plate 602 by a clamp feature 604 and set screws 606. Attached to the input shaft 610 is a pair of mounting clamps 614, 616 that are configured to engage and support the surgical instruments 520, 530. An ergonomic handle 612 may be provided on the proximal end of the input shaft 610 to facilitate pivoting of the input shaft 610 and surgical tools 520, 530 mounted thereto about vertical axis VA-VA.

As show in FIG. 10, the flexible interface support assembly 510 may be employed in connection with a cable-controlled, steerable guide tube assembly 200 which may be supported, for example, by the gooseneck mounting tube 36. In this embodiment, the inner sheath assembly 222 that protrudes from handle portion 210 includes at least one steerably working channel 230 of the type described above, the distal end of which may be articulated in the left/right directions and in the up/down directions. In particular, a left/right articulation cable 232 is attached to the distal end of the working channel 230 as was described above and depicted, for example, in FIG. 6. The left/right articulation cable 232 may extend through a flexible cable sheath or coil tube 231 that extends through the inner sheath assembly 222. In various embodiments, the left/right articulation cable 232 is sized relative to the flexible coil tube 231 such that it is freely movable therein.

The left/right articulation cable 232 and its coil tube 231 may be operably coupled to the tool docking assembly 600 by a first quick-connection arrangement generally designated as 630. The quick-connection arrangement 630 may comprise a clamp feature 632 and set screw 634 that is provided in the second cable mounting bracket 580 and is configured to clamp a ferrule 270 that is attached to the coil tube 231 of the left/right articulation cable 232. The left/right articulation cable 232 passes through a smaller diameter hole 634 in the second cable mounting bracket 280 and is inserted through a hole 636 in the tool docking plate 602. The end of the left/right articulation cable 232 is affixed to the tool docking plate 602 by an end ferrule 267 that is crimped onto or otherwise affixed to the end of the cable 232 and which has a diameter that is larger than hole 636 in the tool docking plate 602.

Pivoting the tool docking plate 602 about the pin axis (vertical axis VA-VA) of the friction hinge 584 results in the cable 232 translating within the cable outer jacket 231 to facilitate motion of the cable 232 at the interface between the assembly 10 and the cable-controlled guide tube system. Pivotable mounting of the outer cable jacket end ferrule 270 and the cable end ferrule 267 allows the use of a solid core cable without bending or kinking. Such arrangement enables the clinician to actuate the left/right articulation cable 232 to cause the first working channel 230 to articulate in a left or right direction depending upon whether the cable 232 is being pushed through the coil tube 231 or pulled through the coil tube 231. In particular, when the clinician pivots the tool docking plate 602 about the vertical axis VA-VA in a direction towards the second tool docking bracket 580, the left/right articulation cable 232 is pushed through the coil tube 231 and the distal end of the first working channel 230 is articulated to a "first" or left direction. When the clinician moves the tool docking plate 602 away from the second tool docking bracket 580, the left/right articulation cable 232 is pulled through the coil tube 231 and the distal end of the first working channel 230 is articulated to a "second" or right direction.

Also in various embodiments, the up/down articulation cable 234 is attached to the first vertically extending cable mounting bracket 570 and a second vertically extending cable mounting plate 583 that is attached to the second cable mounting bracket 580 by a second quick-connection arrangement generally designated as 640. The second quick-connection arrangement 640 may comprise a bore that is provided in the first vertically extending cable mounting bracket 570 and is sized to receive therein a ferrule 292 that is attached to the outer sheath 233 of the up/down articulation cable 234. The ferrule 292 may be held in position by a clamping feature or other arrangement. The cable 234 passes through the first vertically extending cable mounting bracket 570 and is inserted through a hole 642 in the second vertically extending cable mounting plate 583. The end of the cable 234 is affixed to the second vertically extending cable mounting plate 583 by a tube segment 299 that is crimped onto or otherwise affixed to the end of the cable 234 and which has a diameter that is larger than hole 642 in the second vertically extending cable mounting plate 583.

By pivoting the second cable mounting bracket 580 and the second vertically extending cable mounting plate 583 attached thereto about pivot axis PA-PA, the clinician can actuate the up/down cable 234 to cause the distal end of the working channel 230 to articulate up and down depending upon whether the cable 234 is being pushed through the coil tube 233 or pulled through the coil tube 233. For example, when the clinician pivots first the second cable mounting bracket 580 and the second vertically extending cable mounting plate 583 in a direction towards the steerable guide tube assembly 200 about the horizontal pivot axis HPA-HPA, the up/down articulation cable 234 is pushed through the coil tube 233 which causes the distal end of the first working channel 230 to pivot downward. Likewise, when the clinician pivots the second cable mounting bracket 580 and the second vertically extending cable mounting plate 583 away from the steerable guide tube assembly 200 about horizontal pivot axis HPA-HPA, the distal end of the first working channel 230 is articulated in an upward direction. Those of ordinary skill in the art will appreciate that either or both of the flexible sheath portions 522, 532 of the surgical instruments, respectively may be inserted through the first working channel 230 or only one of those sheaths 522, 532 may be inserted through the working channel 230 and the other sheath may be inserted through another working channel in the guide tube assembly 200.

Figure 12:
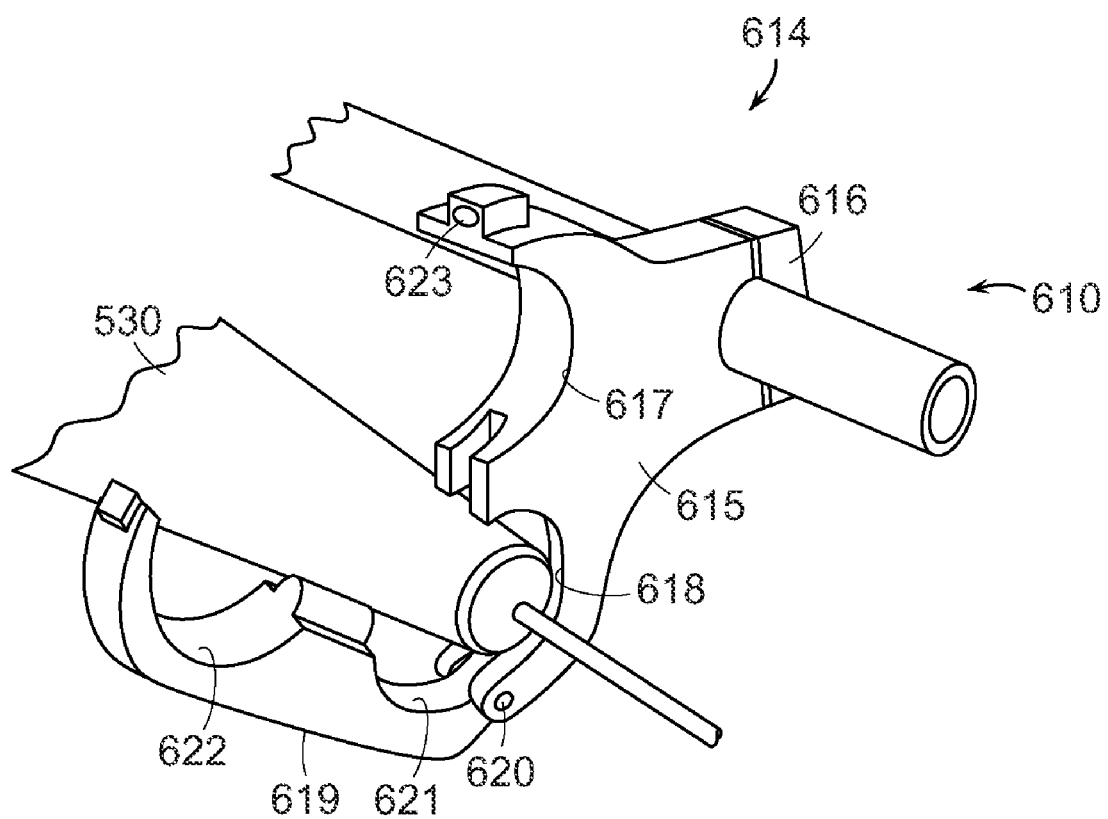
FIG. 12 is a partial perspective view of a mounting clamp embodiment of the present invention along with a portion of a surgical instrument.

In various embodiments, the endoscopic surgical instruments 520, 530 may be releasably coupled to the input shaft 610 by a clamp 614. As can be seen in FIG. 12, the clamp 614 may comprise a clamp body 615 that has a first clamp arm 616 that may be attached thereto by screws (not shown) to facilitate clamping of the clamp body 615 to the input shaft 610 as shown in FIG. 12. The clamp body 615 may be provided with a plurality of tool docking station recesses 617, 618 that are sized to receive a portion of the endoscopic surgical instruments 520, 530 therein. A second clamp arm 619 may be attached to the clamp body 615 by a hinge pin 620 and have recesses 621, 622 therein as shown. A magnet arrangement 623 may be employed to retain the second clamp arm 619 in clamping engagement with the clamp body 615 to support the instruments 520, 530 therein. Such arrangement enables the instruments 520, 530 to be quickly attached and detached to the input shaft 610. Other embodiments may employ threaded fasteners, clips, etc. to retain the second clamp arm 619 in clamping engagement with the clamp body 615.

It will be further appreciated that depending upon how the cables are attached to the tool docking assembly 600, movement of the handle portions of the surgical instruments 520, 530 causes the cable controlled guide tube to impart laparoscopic-like movement of the distal tips of the flexible portions of the surgical instruments. For example, when the handle is lifted up, the cable controlled working channel through which the flexible working portion extends may move the tip portion downward or upward depending upon how the cables are coupled to the tool docking stations. Likewise, when the handle is moved left, the working channel may cause the distal tip to move left or right. It will be further appreciated that the unique and novel features of the various embodiments of the flexible user interface support assembly 510 of the present invention enable the control cables for the cable controlled guide tube system to remain in any desired fixed position after the pivotal motions applied to the tool docking assembly or the surgical instruments docked therein have been discontinued.

Figure 13:
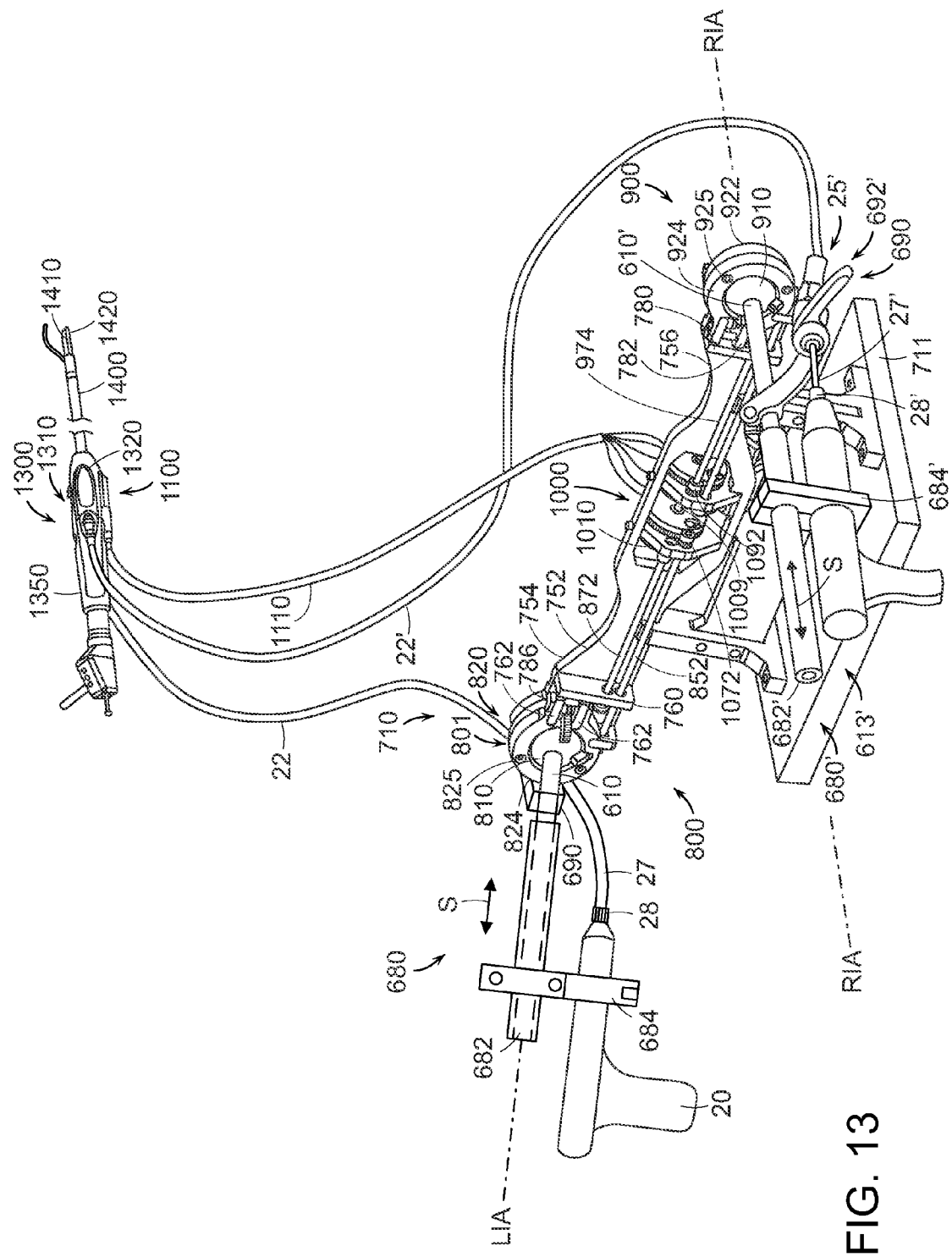
FIG. 13 is a perspective view of another flexible user interface support assembly of the present invention supporting two endoscopic tools in relation to a steerable guide tube assembly.
Figure 14:
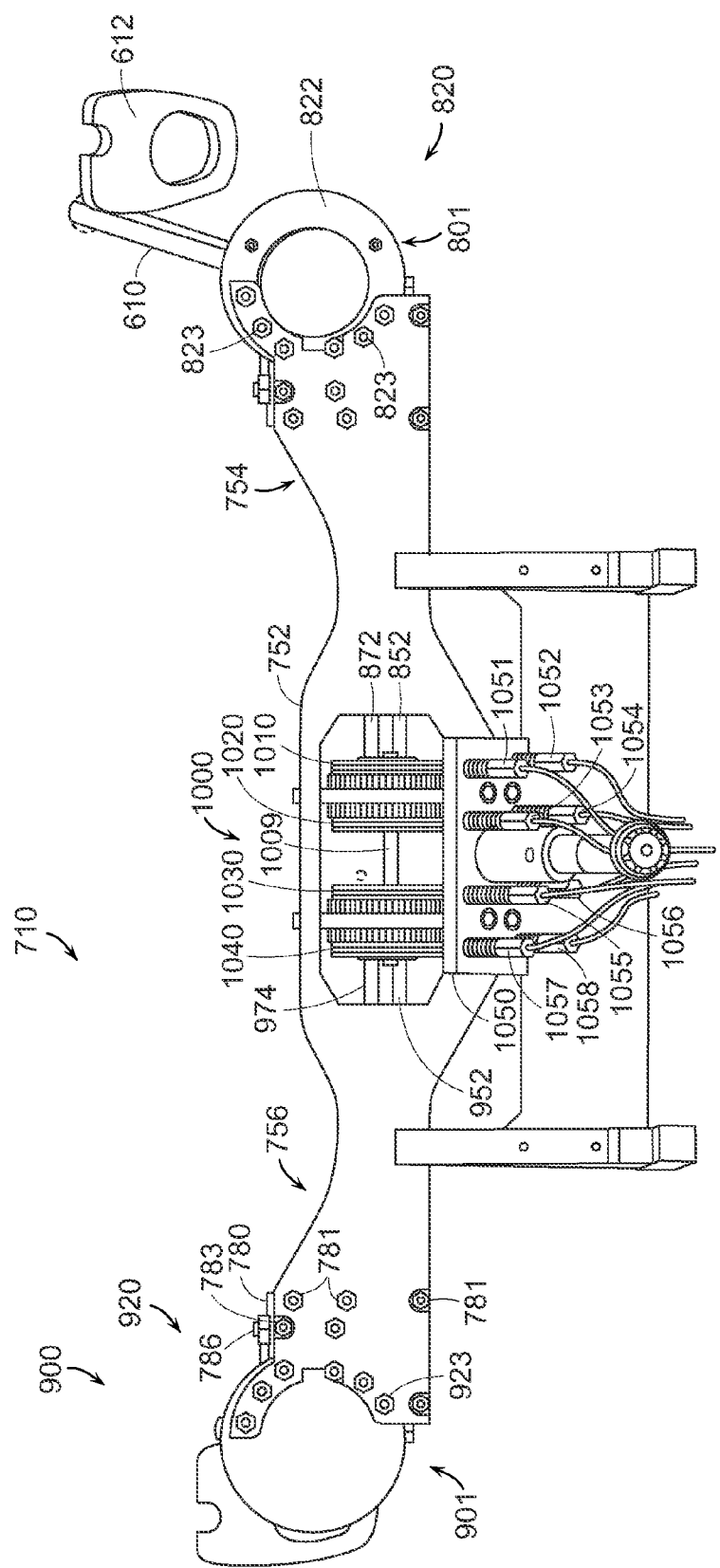
FIG. 14 is a rear elevational view of the flexible user interface support assembly depicted in FIG. 13.
Figure 15:
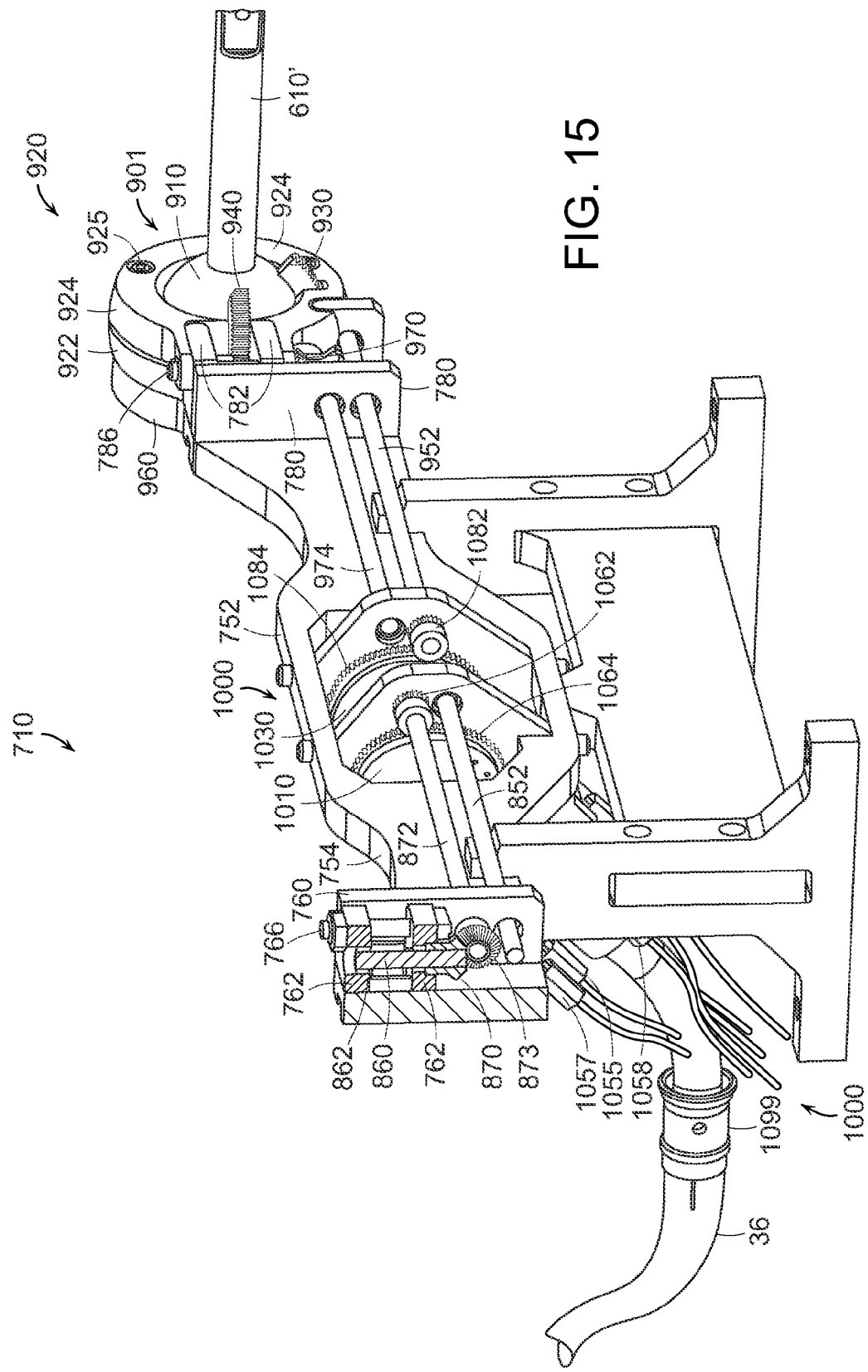
FIG. 15 is a partial cross-sectional perspective view of the flexible user interface support assembly depicted in FIGS. 13 and 14.

FIGS. 13-32 illustrate another flexible user interface support assembly embodiment generally designated as 710 that may operably support two or more conventional endoscopic surgical instruments 20, 20' in connection with a cable-controlled, steerable guide tube assembly 1300. As can be seen in FIG. 13, an embodiment of the flexible interface support assembly 710 may include a surgical tool docking assembly 750 that may be operably attached to a support surface 711 such as, for example, a conventional work stand, a portion of a bed, etc. Various embodiments of the mounting assembly 750 may include a central cross bar 752 that may be clamped onto or otherwise fastened to the support surface 711 or, if desired, a conventional tool stand as was described hereinabove. The mounting assembly 750 may include a "first" or left tool docking station generally designated as 800 and a "second" or right tool docking station generally designated as 900. The left tool docking station 800 may be operably attached to a left end 754 of the central cross bar 752 and the right tool docking station 900 may be mounted to the right end 756 of the central cross bar 752.

In various embodiments, the left tool docking station 800 may include a "first" or left ball and socket assembly 801. The left ball and socket assembly 801 may include a left sphere assembly 810 that is rotatably supported within a left housing assembly 820. Left housing assembly 820 may comprise, for example, a left sphere holder plate 822 that may be coupled to the left end 754 of the central cross bar 752 by, for example, screws 823 or other suitable fastener arrangements. See FIG. 14. The left housing assembly 820 may further include a left clamp plate 824 that is coupled to the left sphere holder plate 822 by screws 825 or other suitable fasteners. In addition, a left side plate 760 is attached to the left side 754 of the central cross bar 752. See FIGS. 13 and 26. A pair of spaced horizontal plates 762 are attached to the left side 754 of the central cross bar 752 by, for example, screws (not shown). The left clamp plate 824 may be configured to be journaled on a left hinge pin 766 that extends between the plates 762. The left clamp plate 24 allows the user to adjustably tension the sphere assembly 810 within a cavity 3000 formed by the left housing assembly 820 to generate a desired amount of resistance to for example retain the sphere assembly 810 and the surgical instrument 20 attached thereto in position when the clinician discontinues application of a positioning motion thereto. That is, when the clinician removes his or her hands from the surgical instrument 20, the friction created between the clamping plate 824 and the sphere assembly 810 will retain the sphere assembly and surgical instrument in that position. The left hinge pin 766 defines a first vertical axis FVA-FVA about which the first ball and socket assembly 801 may pivot relative to the central cross bar 752. See FIG. 26.

In various embodiments, the housing 820 acts as an unmovable reference or "ground" for the ball and socket system. Assembled within the spherical cavity 3000 is a vertical output gear segment 830 that has a primary axis of "PA1-PA1" that passes through the center of the spherical cavity 3000. This vertical output gear segment 830 may be constrained such that it can rotate about its horizontal primary axis of rotation PA1-PA1 by way of channels 826, 828 provided in the unmovable housing 820. By allowing the face of the gear segment 830 to ride on the walls of these channels 826, 828, the gear segment 830 is now unable to move in any plane other than which is normal to its axis of rotation PA1-PA1. See FIG. 16.

These embodiments may further include a sphere 810 that serves to "anchor" the axis rotation of the gear segment 830. In particular, a shaft 3002 extends from the gear segment 830 into the center of the sphere 810. In this manner, the gear segment 830, which was already constrained to motion in one plane can now be considered constrained to prevent translation in all directions and only allowing rotation about horizontal axis PA1-PA1 which passes through the center of the sphere 810. In addition, a user input shaft 610 may be attached to the sphere 810 for coupling surgical instruments or other articulatable user interfaces as will be discussed in further detail below. Movement of the input shaft 610 in any direction is translated into a proportional rotation of the gear segment 830 around horizontal input axis PA1-PA1 without regard for any input motion that occurs off axis. More specifically, an input motion by the user to the sphere 810 via the input shaft 610 will result in rotation of the gear segment 830 only if some element of the input is in the vertical direction. Thus, if the input motion were only in the horizontal direction, no relative motion would be registered on the vertical output gear 830.

Figure 16:
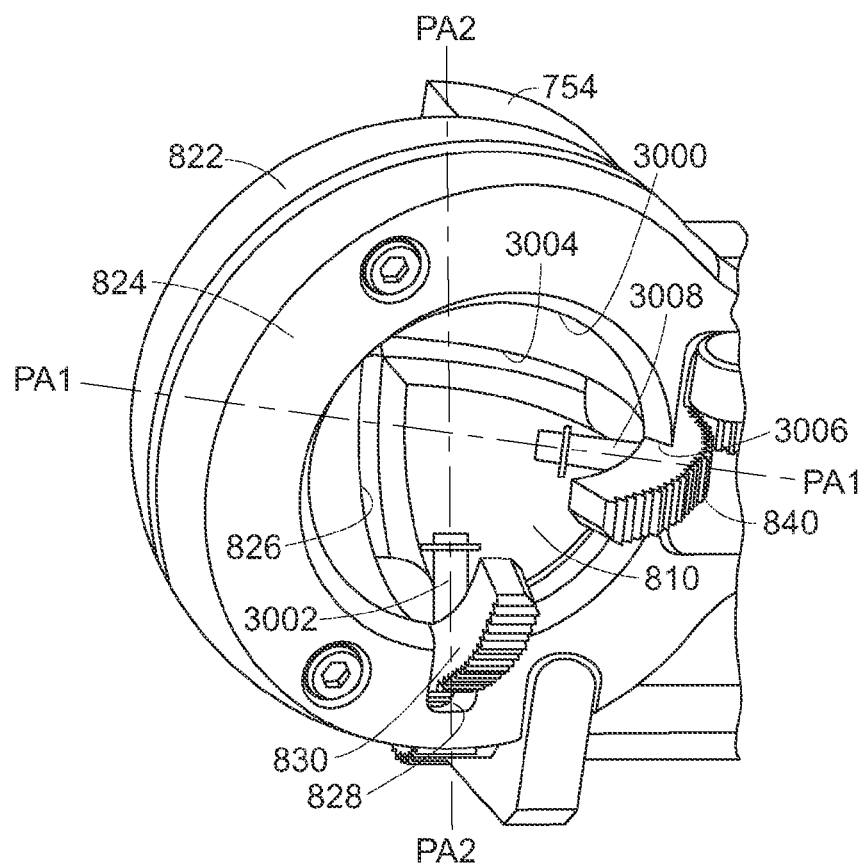
FIG. 16 is a partial perspective view of a left tool docking station embodiment of the present invention, with a portion of the sphere assembly thereof removed for clarity.

As can also be seen in FIG. 16, the left tool docking station 800 further includes a horizontal input gear segment 840 which can be constrained in a similar manner to the vertical input gear segment 830 but with the horizontal input gear segment 840 oriented 90° relative thereto. The horizontal input gear segment 840 is oriented to rotate about a vertical axis PA2-PA2. The horizontal input gear segment 840 is constrained such that it is only able to rotate about its vertical primary axis of rotation PA2-PA2 by way of channels 3004, 3006 provided in the unmovable housing 820. By allowing the face of the gear segment 840 to ride on the walls of these channels 3004, 3006 the gear segment 840 is now unable to move in any plane other than which is normal to its axis of rotation PA2-PA2. A shaft 3008 extends from the gear segment 840 into the center of the sphere 810. In this manner, the gear segment 840 which was already constrained to motion in one plane can now be considered constrained to prevent translation in all directions and only allowing rotation about vertical axis PA2-PA2 which passes through, the center of the sphere 810. Thus, the shafts 3002, 3008 extending respectively from gear segments 830, 840 towards the center of the sphere 810 are constrained to be 90° from the input shaft 610 wherein the surgical instruments or tools are mounted.

Figure 17:
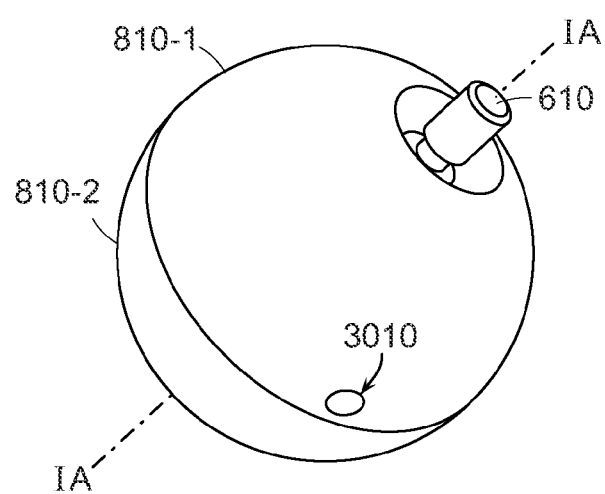
FIG. 17 is a perspective view of a sphere assembly of a left tool docking station embodiment of the present invention.
Figure 18:
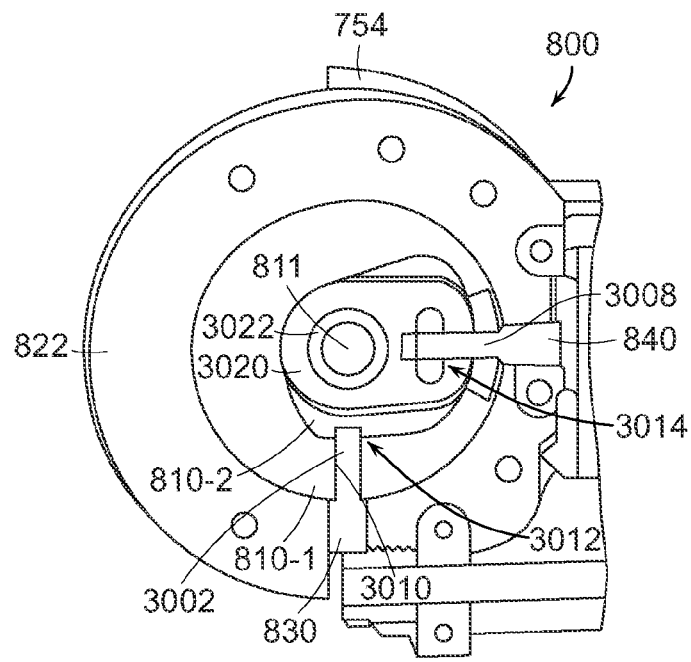
FIG. 18 is a cross-sectional view of a portion of a left tool docking station embodiment of the present invention.

In preferred embodiments, it is desirable for the shafts 3002, 3008 to be round to facilitate rotation of the sphere 810 relative to the gear 830, 840 along the axis of the shaft 3002, 3008. It will be appreciated that in such embodiments, the angle defined by these two shafts 3002, 3008 is dynamic to enable the system to achieve the desired motions. As can be seen in FIGS. 17 and 18, the shaft on the gear segment 830 is constrained to the plane originally described by the two axes normal to the input shaft 610 by extending through a hole 3010 in the sphere 810. Shaft 3002 rotatably extends through the hole 2010 and is retained in position by an e-clip 3012. A central rotator 3020 is movably supported within the sphere 810. The shaft 3008 of the gear segment 840 is affixed to the central rotator 3020 by an e-clip 3014. The input shaft is attached to a bearing 3022 within the central rotator 3020 by an input shaft screw 611 such that the central rotator 3020 can freely rotate about the input axis IA-IA defined by input shaft 610 but is constrained to the same plane as that of the shafts 3002, 3008 of the two gear segments 830, 840. To aid in the fabrication process, the sphere 810 may comprise a front component 810-1 and a rear component 810-2 that is attached thereto.

Figure 19:
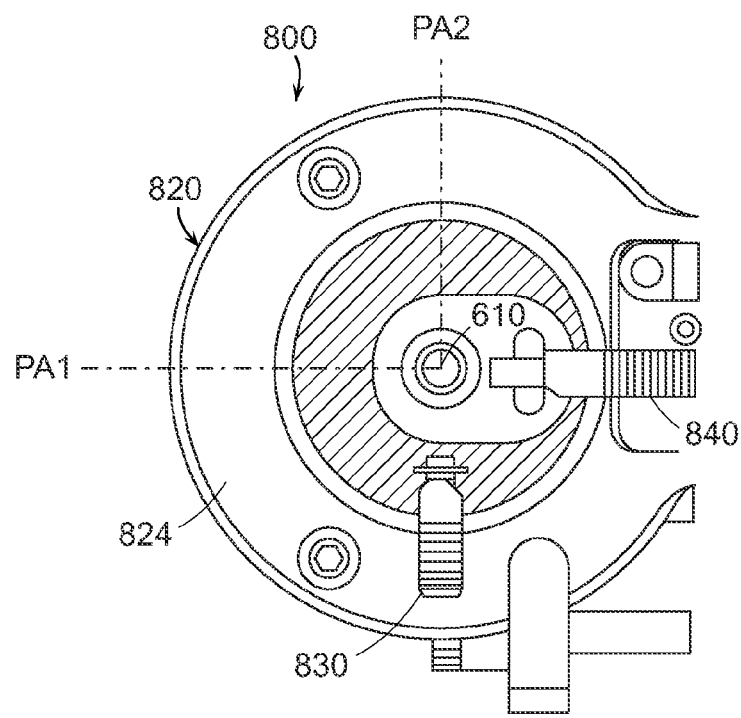
FIG. 19 is another cross-sectional view of a left tool docking station embodiment wherein the input shaft is in a neutral position.
Figure 20:
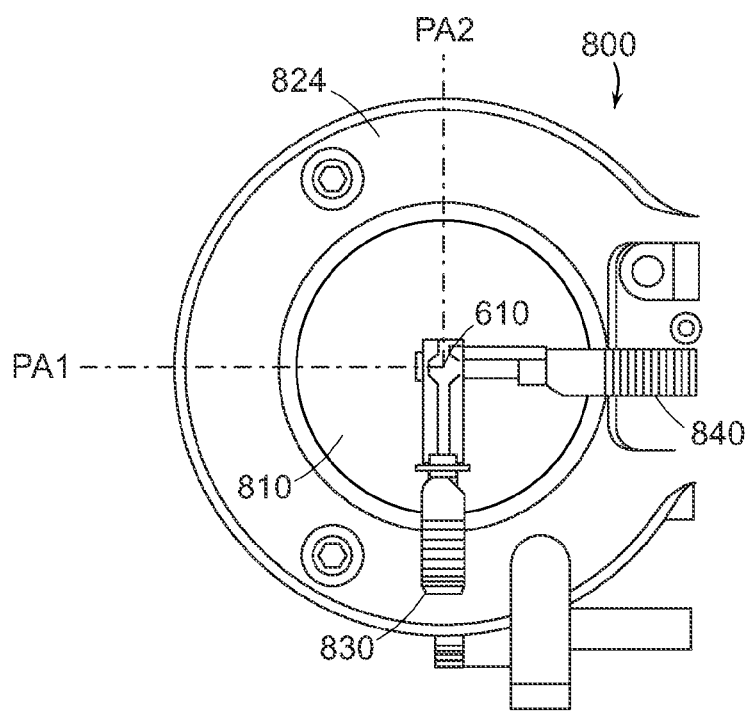
FIG. 20 is a front elevational view of the left tool docking station embodiment of FIG. 19.
Figure 21:
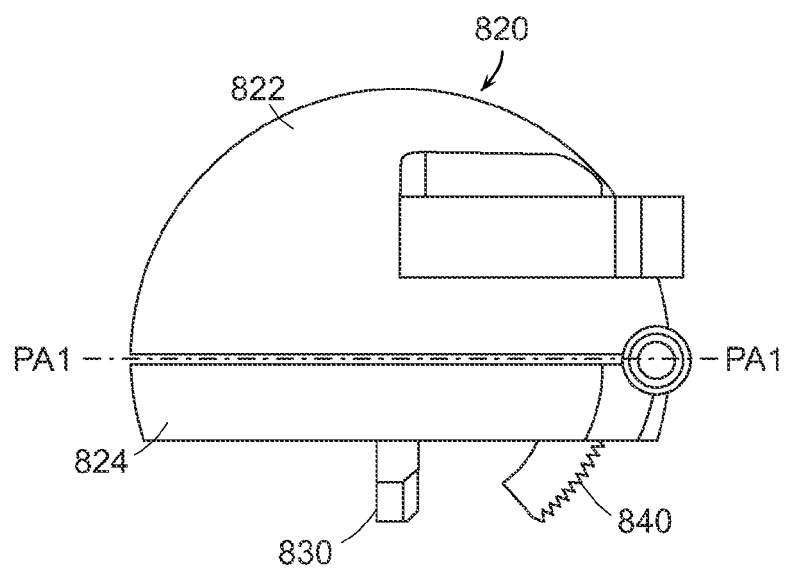
FIG. 21 is a top view of the left tool docking station embodiment of FIGS. 19 and 20.
Figure 22:
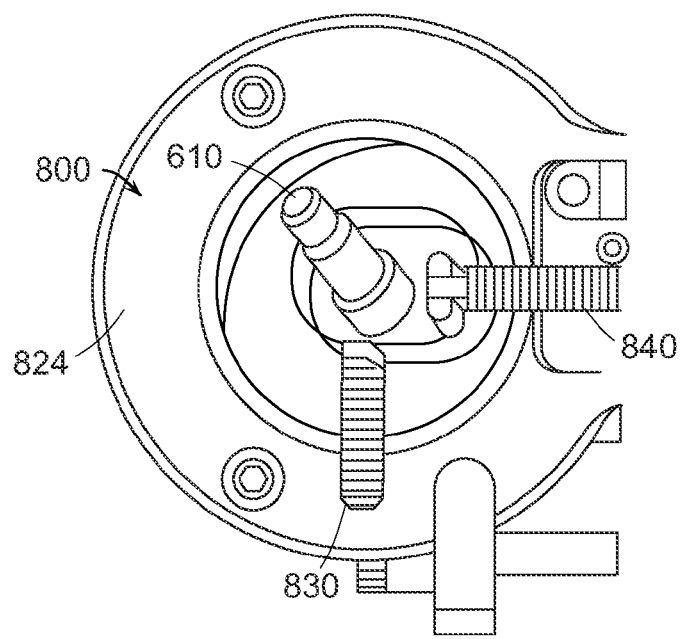
FIG. 22 is another cross-sectional view of a left tool docking station embodiment wherein the input shaft is in a non-neutral position.
Figure 23:
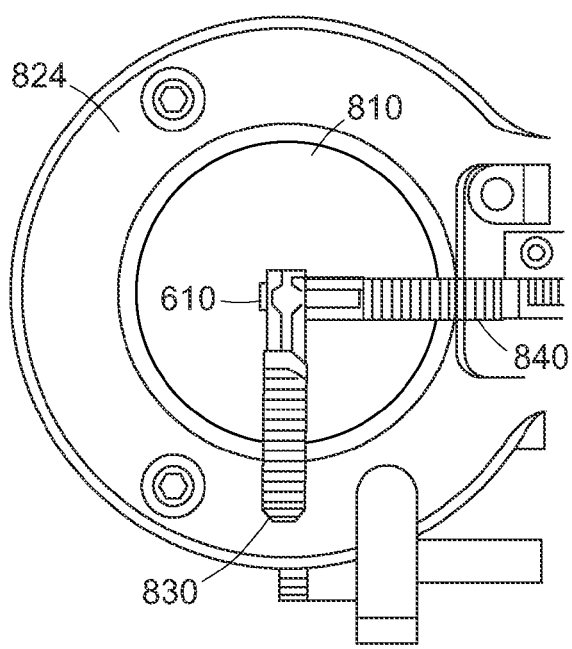
FIG. 23 is a front elevational view of the left tool docking station of FIG. 22.
Figure 24:
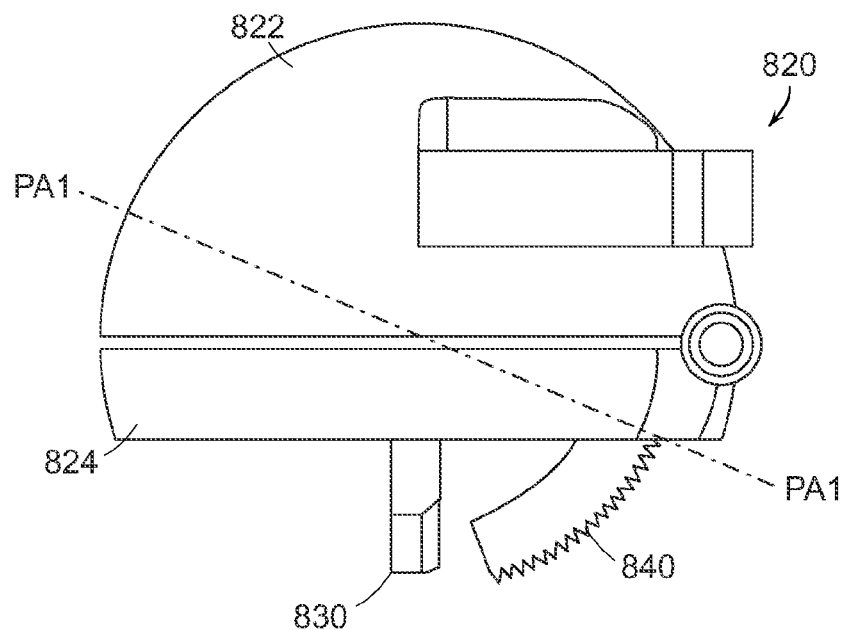
FIG. 24 is a top view of the left tool docking station of FIGS. 22 and 23.
Figure 25:
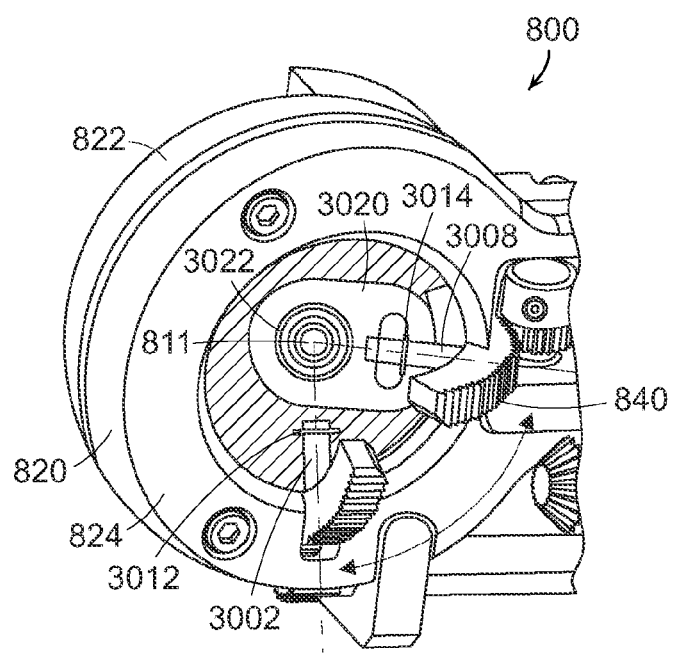
FIG. 25 is another perspective view of a left tool docking station wherein the input shaft is in a non-neutral position and some components are shown in cross-section for clarity.
Figure 26:
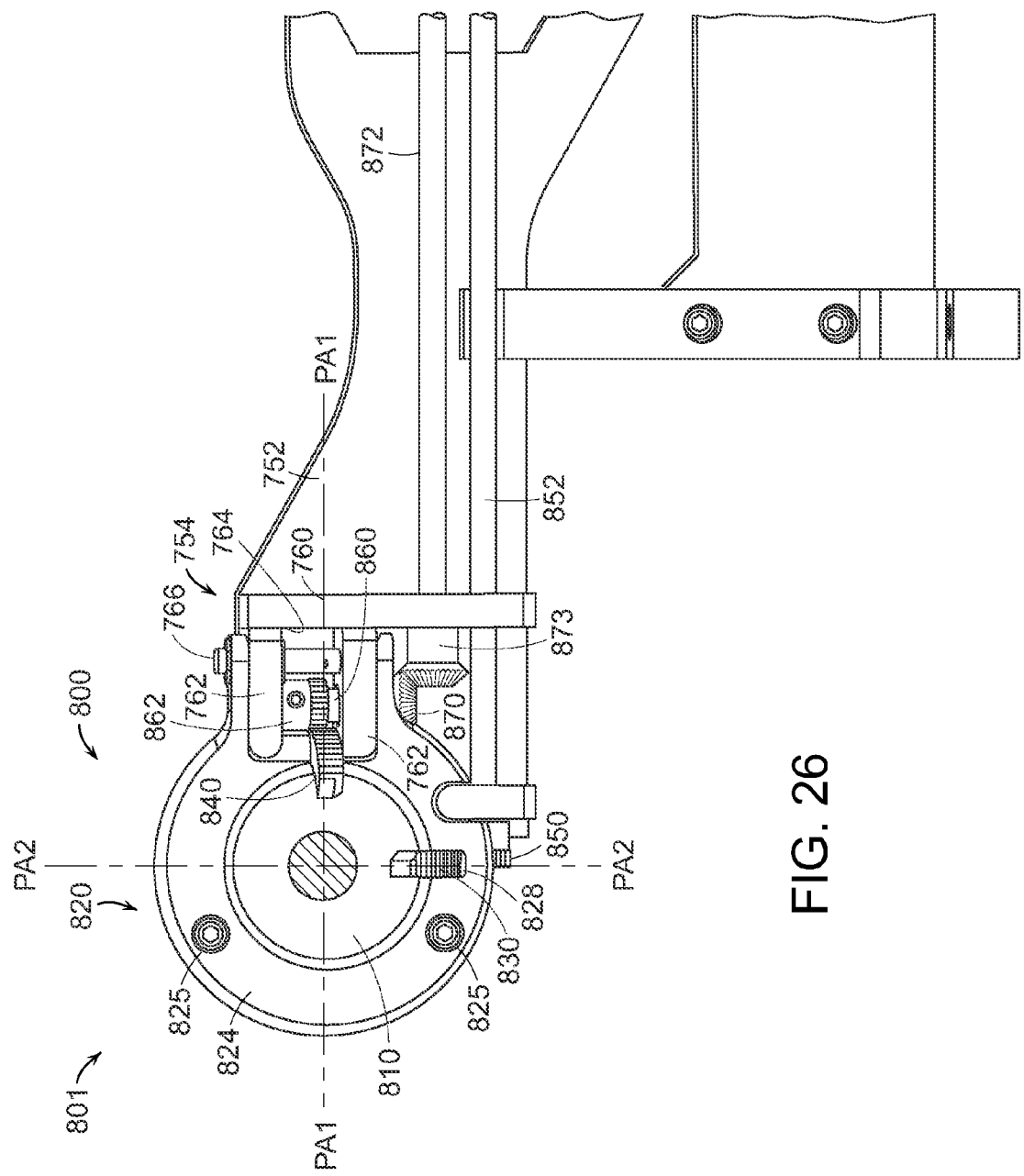
FIG. 26 is a partial front elevational view of a left tool docking station embodiment of the present invention.
Figure 27:
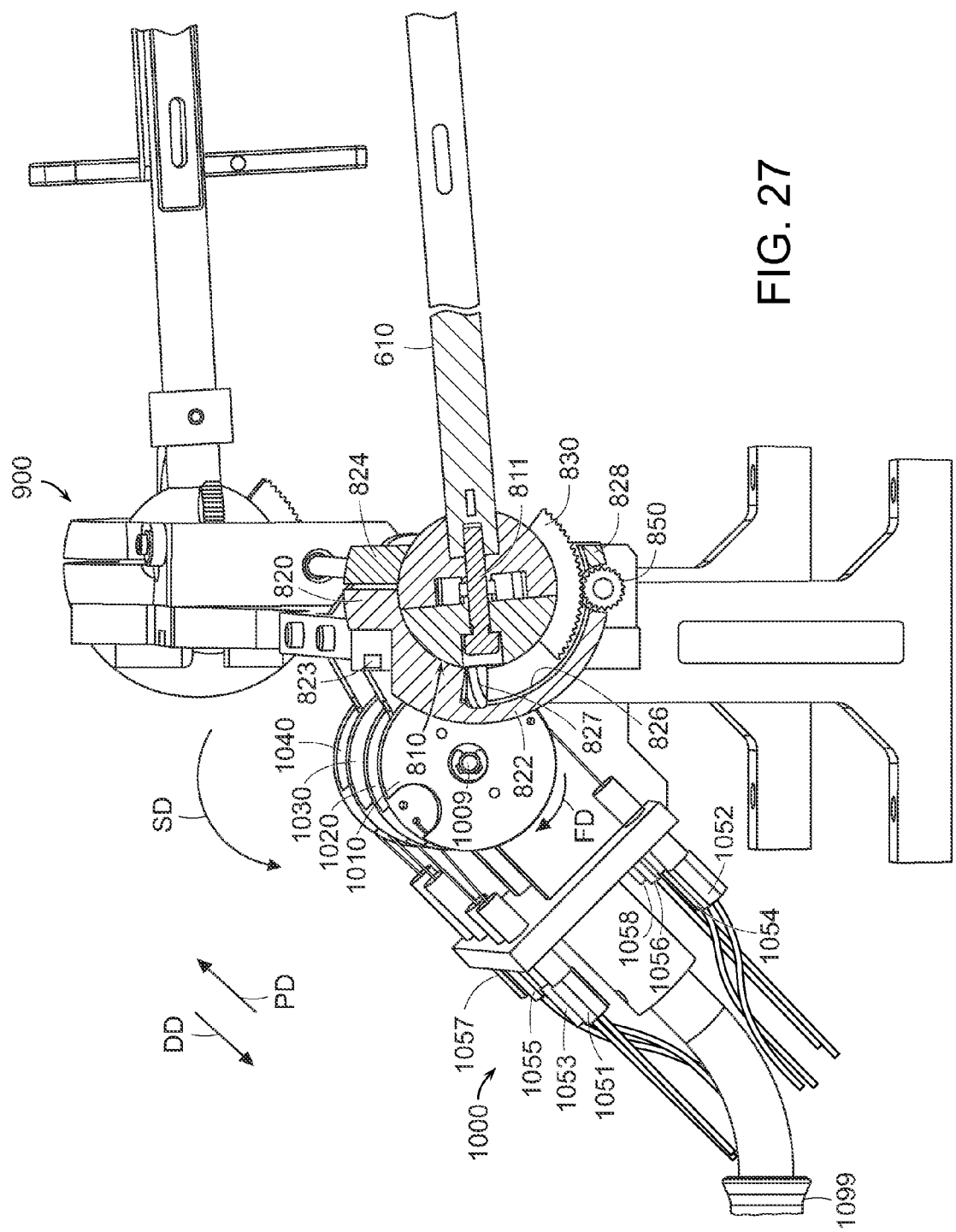
FIG. 27 is another partial cross-sectional view of a left tool docking station portion of an embodiment of the present invention.
Figure 28:
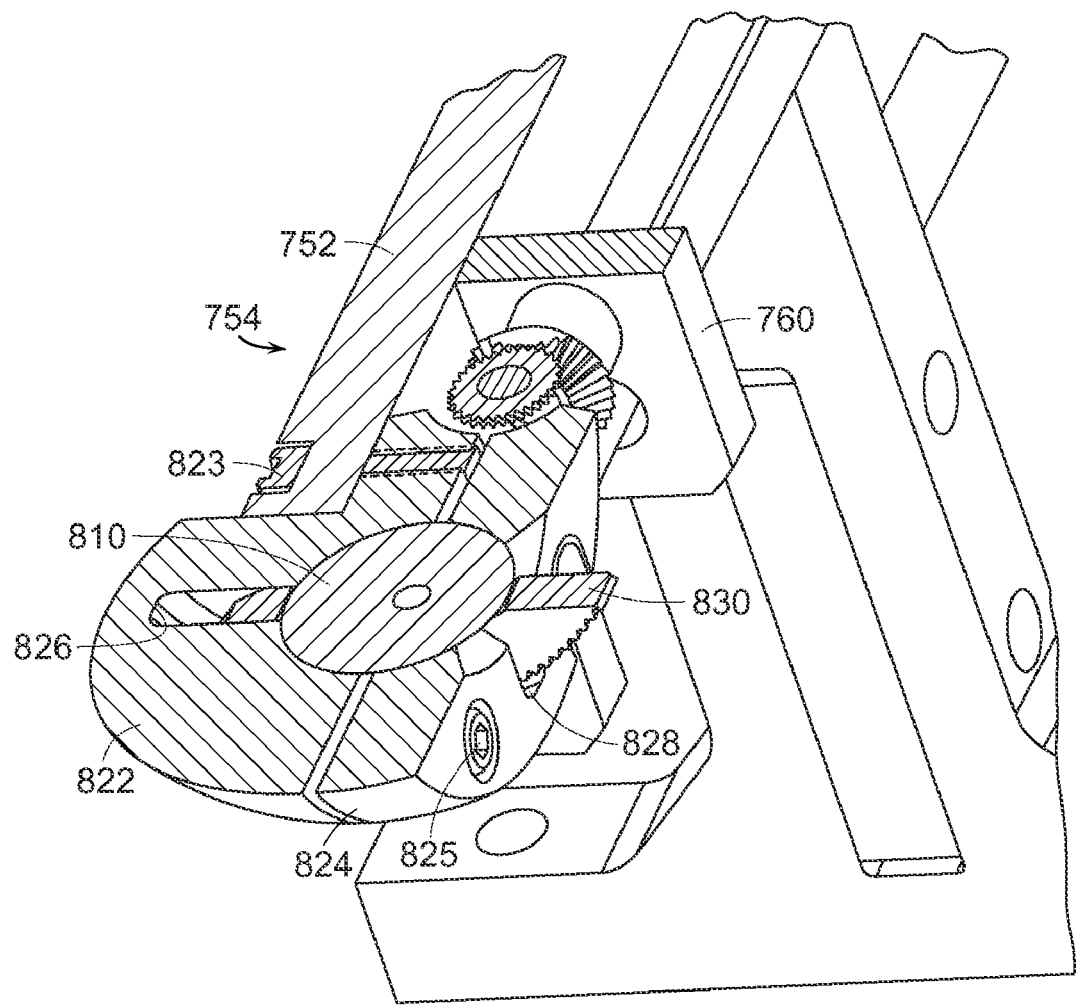
FIG. 28 is another partial cross-sectional view of a left tool docking station embodiment of the present invention.

FIGS. 19-21 depict various components when the input shaft is in a central or "neutral" position. As can be seen in those Figures, the two gear segments 830, 840 are at right angles to each other. Once the input shaft 610 has been moved to a non-neutral position, the axes of the shafts 830, 840 have also moved to an alternate position (although the faces of the gears 830, 840 are still constrained to the slots (826, 828 for gear segment 830 and 3004, 3006 for gear segment 840). See FIGS. 22-24. Furthermore, by sighting down the input shaft 610 with the sphere 810 in a non-neutral position, it can be seen that the orientation of the two gear shafts 3002, 3008 relative to each other has changed. See FIG. 25.

As can be seen in FIG. 13, the endoscopic surgical instrument 20 may be attached to the left tool docking station 800 by a unique and novel tool mounting assembly generally designated as 680 that comprises a left tool mounting tube 682 that is slidably received on the left input shaft 610. A tool clamp assembly 684 is clamped onto or otherwise attached to the left tool mounting tube 682 and is configured to releasably clamp or otherwise engage the surgical instrument 20. The left input shaft 610 may be attached to the left sphere assembly 810 by a screw 811. See FIG. 27. In general, the left input shaft 610, the left tool mounting tube 682 and the tool clamp assembly 684 may be collectively referred to herein as the left tool mounting assembly 613.

In various embodiments, the first left driver gear 830 is positioned in meshing engagement with a first vertical pinion gear 850 that is attached to a first left drive shaft 852. Thus, rotation of the left sphere assembly 810 about the horizontal pivot axis PA1-PA1 will cause the first left driver gear 830 and first vertical pinion gear 850 to impart a rotary motion of a first left drive shaft 852. Similarly, the second left driver gear 840 is in meshing engagement with a first horizontal pinion gear 862 that is attached to a left pinion shaft 860 mounted between the plates 762. Thus, rotation of the left ball and socket assembly 801 about the vertical pivot axis FVA-FVA will cause the second left driver gear 840 and first horizontal pinion 860 to impart a rotary motion to the left pinion shaft 862 and a first left miter gear 870 attached thereto. The first left miter gear 870 is in meshing engagement with a second left miter gear 873 that is attached to a second left drive shaft 872. The first and second left drive shafts 852, 872, respectively, may extend through the left side plate 760 and be rotatably supported therein in corresponding bearings (not shown). The first and second left drive shafts 852, 872 serve to impart rotary drive motions to a centrally disposed cable drive assembly 1000 as will be discussed in further detail below.

The mounting assembly 750 may also include a "second" or right tool docking station 900 that is mounted to the right end 756 of the central cross bar 752 and is substantially identical in construction and operation as the left tool docking station 800. See FIG. 13. For example, in various embodiments, the right tool docking station 900 includes a "second" or "right" ball and socket assembly 901. The right ball and socket assembly 901 may include a right sphere assembly 910 that is rotatably supported within a right housing assembly 920. Right housing assembly 920 may comprise, for example, a right sphere holder plate 922 that may be coupled to the right end 756 of the central cross bar 752 by, for example, screws 923 or other suitable fastener arrangements. See FIG. 15. The right housing assembly 920 may further include a right clamp plate 924 that is coupled to the right sphere holder plate 922 by screws 925 or other suitable fasteners. In addition, a right side plate 780 is attached to the right side 756 of the central cross bar 752 by screws 781 or other suitable fasteners. See FIGS. 14 and 15. A pair of spaced horizontal plates 782 are attached to the right side plate 760 by, for example, screws 783. The right clamp plate 924 may be configured to be journaled on a right hinge pin 786 extending between the plates 782. The right clamp plate 924 allows the user to adjustably tension on the sphere 910 within the right housing assembly 920 to generate a desired amount of resistance to, for example, retain the sphere 910 and surgical instrument 20' attached thereto in position when the clinician discontinues the application of actuation motion thereto. That is, when the clinician removes his or her hands from the surgical instrument 20', the friction created between the clamping plate 924 and the sphere assembly 910 will retain the sphere assembly and surgical instrument in that position. The right hinge pin 786 permits the second ball and socket assembly 901 to pivot about vertical axis TVA-TVA. See FIG. 29.

In various embodiments, the right housing assembly 920 acts as an unmovable reference or "ground" for the right tool docking station 900. Within this unmovable reference 920 is a spherical cavity 3030 which supports the sphere assembly 910 and gear segments 930 and 940. The vertical output gear segment 930 has a shaft (not shown) and is mounted in the above-described manner such that its horizontal primary axis of rotation "PA3-PA3" passes through the center of the spherical cavity 3030. This vertical output gear segment 930 can then be constrained such that it is only able to rotate about its horizontal primary axis of rotation PA3-PA3 by way of channels 926, 928 provided in the unmovable right housing assembly 920. By allowing the face of the gear segment 930 to ride on the walls of these channels 926, 928, the gear segment 930 is now unable to move in any plane other than which is normal to its axis of rotation PA3-PA3. See FIG. 29.

Figure 29:
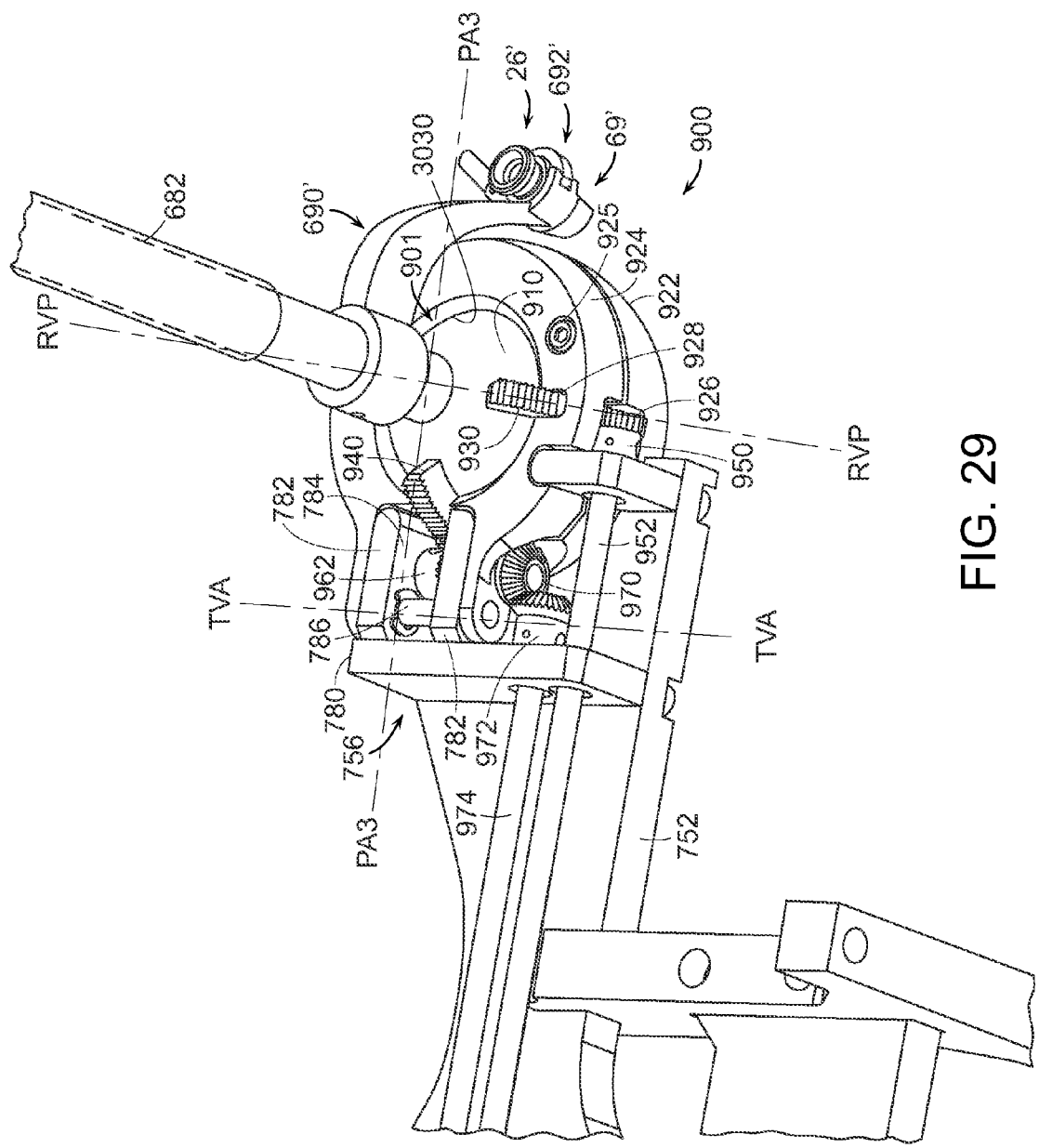
FIG. 29 is a bottom perspective view of a portion of a right tool docking station embodiment of the present invention.
Figure 30:
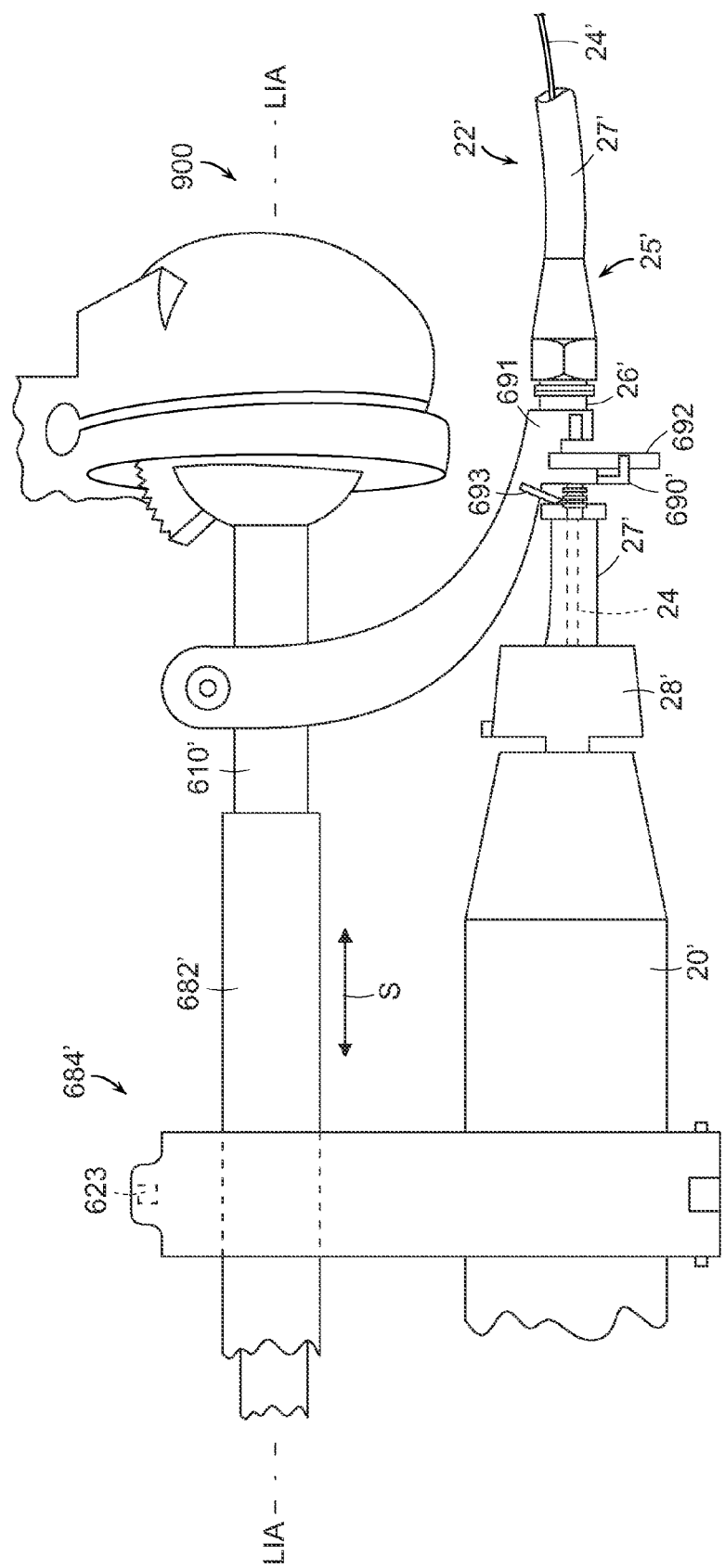
FIG. 30 is a partial side view of a portion of a right side docking station embodiment of the present invention and a cable mounting assembly embodiment of the present invention.

As can also be seen in FIG. 29, the right tool docking station 900 further includes a horizontal input gear segment 940 which can be constrained in a similar manner to the vertical input gear segment 930 but with the horizontal input gear segment 940 oriented 90° relative thereto. The horizontal input gear segment 940 is oriented to rotate about a vertical axis RVP-RVP that also passes through the spherical cavity 3030. The horizontal input gear segment 940 has a shaft (not shown) and is constrained in the above-described manner such that it is only able to rotate about its vertical primary axis of rotation PA4-PA4 by way of channels (not shown) provided in the unmovable right housing assembly 920. As was discussed above, such arrangement constrains the horizontal gear input segment 940 such that it is unable to move in any plane other than which is normal to its axis of rotation PA4-PA4.

As can be seen in FIG. 13, the endoscopic surgical instrument 20 may be attached to the right tool docking station 900 by a unique and novel tool mounting assembly generally designated as 680' that comprises a right tool mounting tube 682' that is slidably received on the right input shaft 610'. A right tool clamp assembly 684' is clamped onto or otherwise attached to the right tool mounting tube 682' and is configured to releasably clamp or otherwise engage the surgical instrument 20'. The right input shaft 610' may be attached to the right sphere assembly 910 by a screw (not shown). In general, the right input shaft 610', the right tool mounting tube 682' and the right tool clamp assembly 684' may be collectively referred to herein as the right tool mounting assembly 613'.

In various embodiments, the first right drive gear segment 930 is positioned in meshing engagement with a right vertical pinion gear 950 that is attached to a first right drive shaft 952. Thus, rotation of the right sphere 910 about the primary horizontal pivot axis PA4-PA4 will cause the third driver gear 930 and third vertical pinion gear 950 to impart a rotary motion to a first right drive shaft 952. Similarly, the fourth driver gear 940 is in meshing engagement with a fourth horizontal pinion gear 962 that is attached to a pinion shaft 960 mounted between the plates 962. Thus, rotation of the second ball and socket assembly 901 about the primary vertical pivot axis PA4-PA4 will cause the fourth driver gear 940 and fourth horizontal pinion 960 to impart a rotary motion to the pinion shaft 962 and a first right miter gear 970. The first right miter gear 970 is in meshing engagement with a second right miter gear 972 that is attached to a second right drive shaft 974.

As was mentioned above, the endoscopic surgical instrument 20 may be attached to the left tool docking station 800 by a unique and novel tool mounting assembly generally designated as 680 that comprises a left tool mounting tube 682 that is slidably received on the input shaft 610. A tool clamp assembly 684 is clamped onto or otherwise attached to the left tool mounting tube 682 and is configured to releasably clamp or otherwise engage the surgical instrument 20. See FIG. 13. In other embodiments, a clamp 614 of the type described above, may also be successfully employed to couple the surgical instrument 20 to the left tool mounting tube 682.

Similarly, the endoscopic surgical instrument 20' may be attached to the right tool docking station 900 by a unique and novel tool mounting assembly generally designated as 680' that comprises a left tool mounting tube 682' that is slidably received on the input shaft 610'. A tool clamp assembly 684' is clamped onto or otherwise attached to the left tool mounting tube 682' and is configured to releasably clamp or otherwise engage the surgical instrument 20'. See FIG. 13. In other embodiments, a clamp 614 of the type described above, may also be successfully employed to couple the surgical instrument 20' to the right tool mounting tube 682'.

Figure 31:
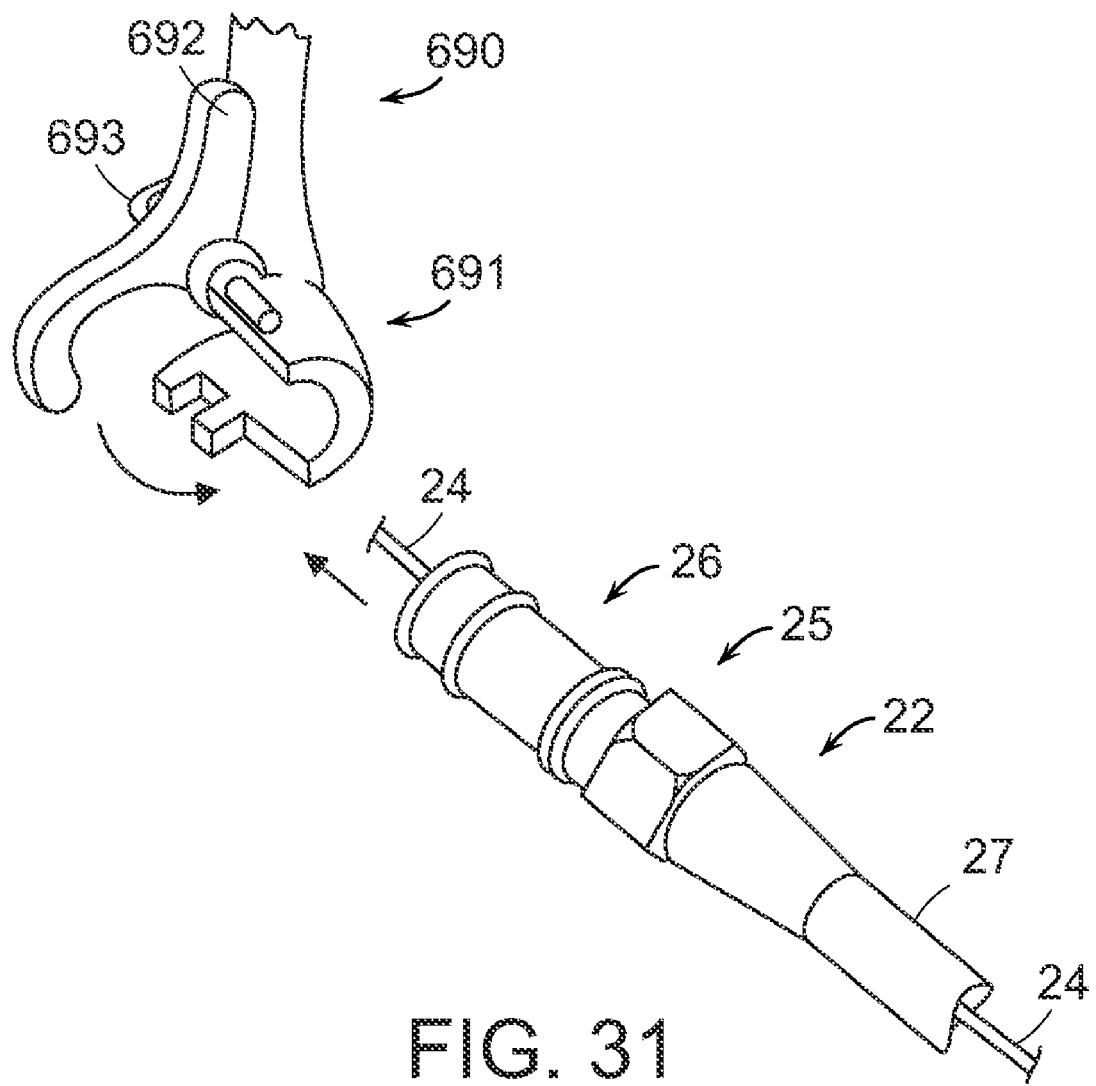
FIG. 31 is a partial exploded assembly view of a cable mounting assembly embodiment of the present invention.

As can be seen in FIG. 13, various embodiments of the present invention may also employ cable mounting assemblies generally designated as 690, 690' for respectively supporting the flexible working portions 22, 22' of the surgical instruments 20, 20'. A cable mounting assembly 690 may include a ferrule coupling portion 691 that includes a movable latch 692 that is movable between a latched and unlatched position. See FIGS. 30 and 31. A spring 693 may be employed to bias the latch 692 into the latched position. The flexible working portion 22 may comprise a hollow outer sheath 27 through which an operating cable 24 from the surgical instrument 20 movably extends. The flexible working portion 22 may further have a ferrule portion 25 that has a flanged barrel 26 that is sized to be received within the ferrule coupling portion 691. When the flanged barrel 26 has been inserted into the ferrule coupling portion 691, it can be retained therein when the latch 692 is moved to the latched position. Likewise, as can be seen in FIG. 31, the flexible working portion 22' may comprise a hollow outer sheath 23' through which an operating cable 24' from the surgical instrument 20' movably extends. The flexible working portion 22' further has a ferrule portion 25' that has a flanged barrel 26' that is sized to be received within the ferrule coupling portion 691. When the flanged barrel 26' has been inserted into the ferrule coupling portion 691, it can be retained therein when the latch 692 is moved to the latched position.

As described above, the tool mounting assembly 680 will enable the clinician to move the surgical instrument 20 on the input shaft 610 along the left input axis LIA-LIA in the directions represented by arrow "S" in FIG. 13. Thus, such movement of the surgical instrument 20 will cause the flexible cable 24 protruding therefrom to move in and out of the sheath 22 which will cause the instrument tip (not shown) to move in and out of a cable docking station 1100 which will be described in further detail below. Likewise, the tool mounting assembly 680' will enable the clinician to move the surgical instrument 20' on the input shaft 610' along a right tool axis "RIA-RIA" in the directions represented by arrow "S" in FIG. 13. Thus, such movement of the surgical instrument 20' will cause the flexible cable 24' protruding therefrom to move in and out of the sheath 22' which will cause the instrument tip (not shown) to move in and out of a cable docking station 1100.

As can be seen in FIG. 13, the first left drive shaft 852, the second left drive shaft 872, the first right drive shaft 952 and the second right drive shaft 974 are configured to drivingly interface with a cable drive assembly 1000 that is centrally disposed on the cross bar 752. In various embodiments, the cable drive assembly 1000 may include a first cable pulley 1010, a second cable pulley 1020, a third cable pulley 1030, and a fourth cable pulley 1040 that are journaled an axle 1009 for controlling cables in connection with a cable-controlled steerable guide tube assembly 1300 or other cable-controlled steerable guide tube assemblies such as the steerable guide tube assembly 200 as described above. See FIG. 32.

Figure 32:
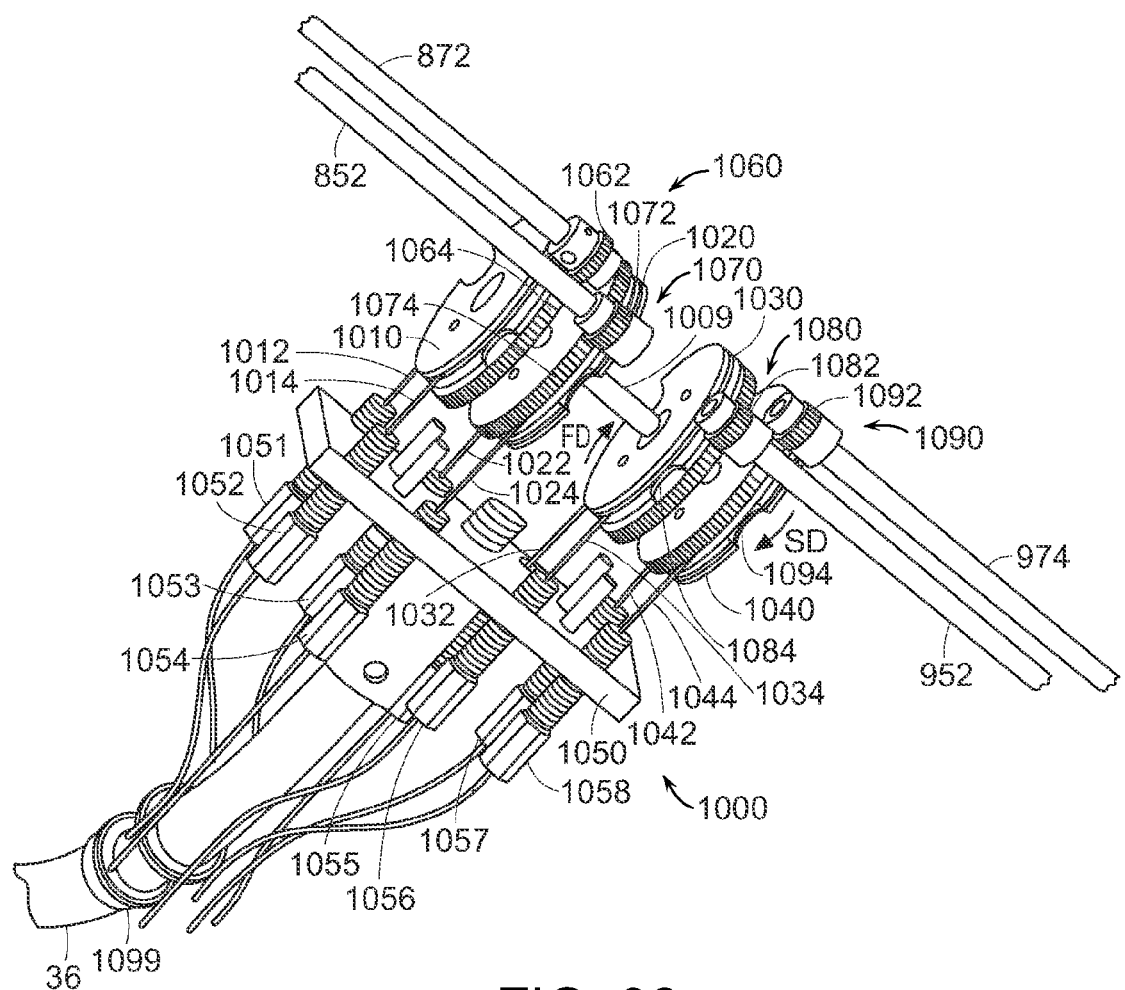
FIG. 32 is a bottom perspective view of a portion of a cable drive assembly embodiment of the present invention.

The first cable pulley 1010 has a first upper cable 1012 and a first lower cable 1014 attached thereto. The first upper and lower cables 1012, 1014 are attached to the first cable pulley such that rotation of the first cable pulley 1010 in first direction "FD" (FIGS. 27 and 32) causes the first upper cable 1012 to be pulled in a proximal direction "PD" and the first lower cable 1014 to be pushed in a distal direction "DD". Likewise, rotation of the first cable pulley 1010 in a second direction "SD" causes the first upper cable 102 to be pushed in the distal direction "DD" and the first lower cable 1014 to be pulled in a proximal direction "PD". The first upper and lower cables 1012, 1014 extend through corresponding hex coil pipe adjuster assemblies 1051, 1052, respectively mounted to a mounting plate 1050 and are ultimately coupled to the steerable guide tube assembly 1300 as will be discussed in further detail below. As can be seen in FIG. 32, rotation of the first cable pulley 1010 is controlled by the second left drive shaft 872 that is coupled to a drive gear train 1060 that consists of intermeshing gears 1062, 1064. Gear 1062 is attached to the second left drive shaft 872. Gear 1064 is attached to the first cable pulley 1010 for rotational travel therewith about an axle 1061. Thus, rotation of the second left drive shaft 872 will cause the gears 1062, 1064 to rotate and ultimately cause the first cable pulley 1010 to rotate as well.

Likewise, the second cable pulley 1020 has a second upper cable 1022 and a second lower cable 1024 attached thereto. The second upper and lower cables 1022, 1024 are attached to the second cable pulley 1020 such that rotation of the second cable pulley 1020 in first direction "FD" causes the second upper cable 1022 to be pulled in a proximal direction and the second lower cable to be pushed in a distal direction. The second upper and lower cables 1022, 1024 extend through corresponding hex coil pipe adjuster assemblies 1053, 1054, respectively in the mounting plate 1050 and are ultimately coupled to the steerable guide tube assembly 1300. Rotation of the second cable pulley 1020 is controlled by rotation of the first left drive shaft 852 that is coupled to a drive gear train 1070 that consists of intermeshing gears 1072, 1074. As can be seen in FIG. 32, the gear 1072 is attached to the first left drive shaft 852. Gear 1074 is attached to the second cable pulley 1014 for rotational travel therewith. Thus, rotation of the first left drive shaft 852 will cause gears 1072, 1074 and ultimately the cable pulley 1014 to rotate.

The third cable pulley 1030 has a third upper cable 1032 and a third lower cable 1034 attached thereto. The third upper and lower cables 1032, 1034 are attached to the third cable pulley 1030 such that rotation of the third cable pulley 1030 in the first direction "FD" causes the third upper cable 1032 to be pulled in the proximal direction and the third lower cable 1034 to be pushed in the distal direction. The third upper and lower cables 1032, 1034 extend through corresponding hex coil pipe adjuster assemblies 1055, 1056, respectively attached to mounting plate 1050 and are ultimately coupled to the steerable guide tube assembly 1300. Rotation of the third cable pulley 1030 is controlled by rotation of the first right drive shaft 952 that is coupled to a drive gear train 1080 that consists of intermeshing gears 1082, 1084. As can be seen in FIG. 32, the gear 1082 is attached to the first right drive shaft 952. Gear 1084 is attached to the third cable pullet 1030 for rotational travel therewith. Rotation of the first right drive shaft 952 will cause gears 1082, 1084 and ultimately, the third cable pulley 1030 to rotate.

The fourth cable pulley 1040 has a fourth upper cable 1042 and a fourth lower cable 1044 attached thereto. The fourth upper and lower cables 1042, 1044 are attached to the fourth cable pulley 1040 such that rotation of the fourth cable pulley 1040 in first direction "FD" causes the fourth upper cable 1042 to be pulled in the proximal direction and the fourth lower cable 1044 to be pushed in the distal direction. The fourth upper and lower cables 1042, 1044 extend through corresponding hex coil pipe adjuster assemblies 1057, 1058 in the mounting plate 1050 and are ultimately coupled to the steerable guide tube assembly 1300. Rotation of the fourth cable pulley 1040 is controlled by rotation of the second right drive shaft 974 that is coupled to a drive gear train 1090 that consists of intermeshing gears 1092, 1094. As can be seen in FIG. 32, the gear 1092 is attached to the second right drive shaft 974. Gear 1094 is attached to the fourth cable pulley 1040 for rotational travel therewith. Thus, rotation of the second right drive shaft 974 will cause gears 1092, 1094 and ultimately the fourth cable pulley 1040 to rotate.

In various embodiments of the present invention, the cables 1012, 1014, 1022, 1024, 1032, 1034, 1042, 1044 are configured to be operably coupled to a steerable guide tube assembly 1300 by a unique and novel cable docking station 1100. In various embodiments, for example, the cable docking station 1100 is clamped or otherwise attached to a flexible gooseneck mounting tube 36 that is attached to a mounting collar 1099 that is affixed to the cable drive assembly 1000. The cables 1012, 1014, 1022, 1024, 1032, 1034, 1042, and 1044 may extend into a hollow sheath 1110 that attaches to the cable docking station 1100. See FIGS. 13, 33, and 34.

Figure 34:
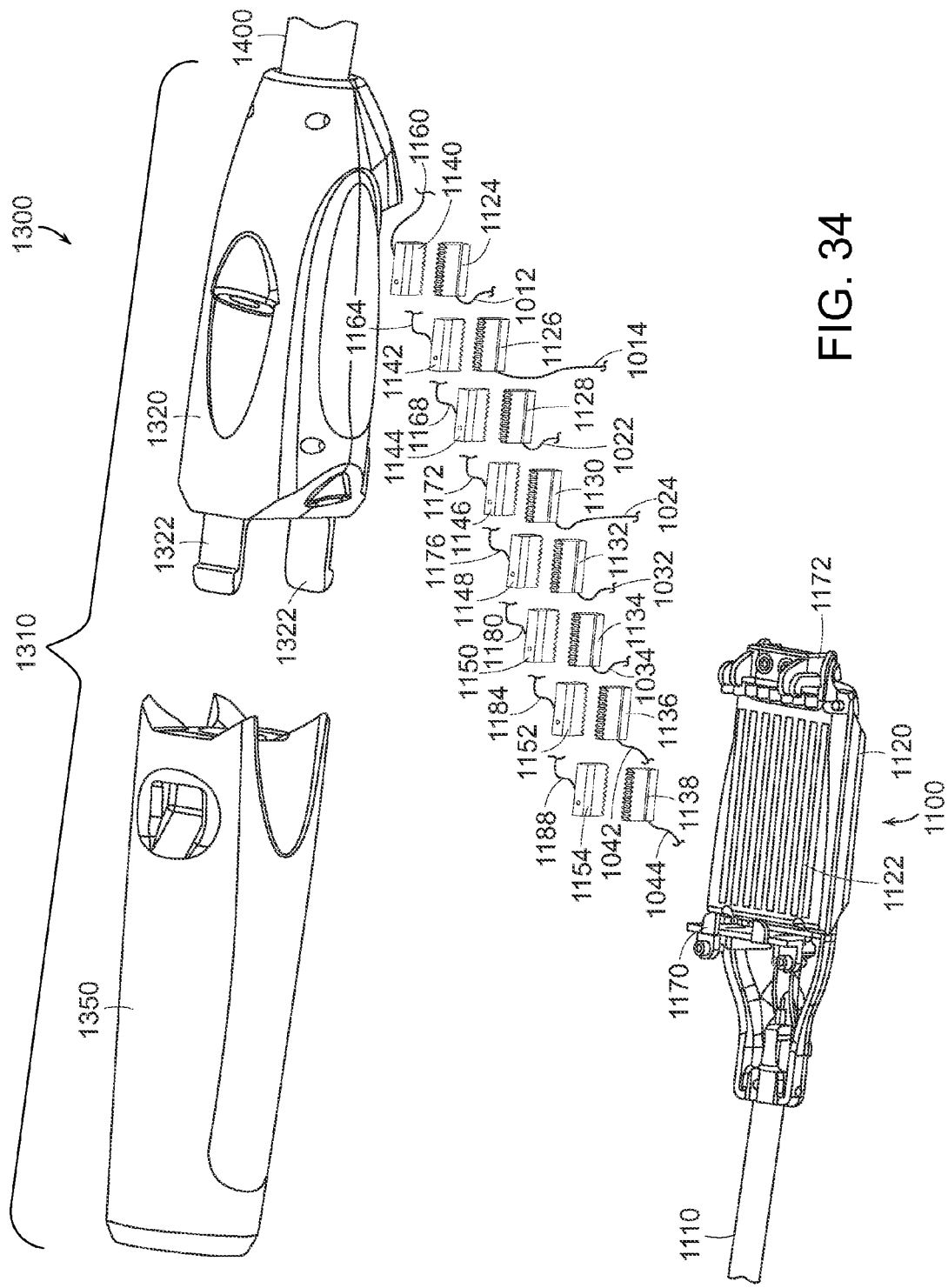
FIG. 34 is a perspective assembly view of portions of the cable docking station and the steerable guide tube assembly depicted in FIG. 33.

As can be seen in FIG. 34, the cable docking station 1100 may include a bottom plate 1120 that operably supports a clamp plate 1122. Clamp plate 1122 may support a series of proximal cable couplers in the form of lower pitch racks that are attached to the distal ends of cables 1012, 1014, 1022, 1024, 1032, 1034, 1042, 1044. For example, a lower pitch rack 1124 may be attached to the distal end of cable 1012. Lower pitch rack 1226 may be attached to the distal end of cable 1014. Lower pitch rack 1228 may be attached to the distal end of cable 1022. Lower pitch rack 1130 is attached to the distal end of cable 1024. Lower pitch rack 1132 is attached to the distal end of cable 1032. Lower pitch rack 1134 may be attached to the distal end of cable 1034. Lower pitch rack 1136 may be attached to the distal end of cable 1042. Lower pitch rack 1138 may be attached to the distal end of cable 1044. Lower pitch racks 1124, 1126, 1128, 1130, 1132, 1134, 1136, and 1138 may be configured to mesh with corresponding distal cable couplers in the form of upper pitch racks 1140, 1142, 1144, 1146, 1148, 1150, 1152, 1154, respectively, that may be supported in the steerable guide tube assembly 1300.

Figure 33:
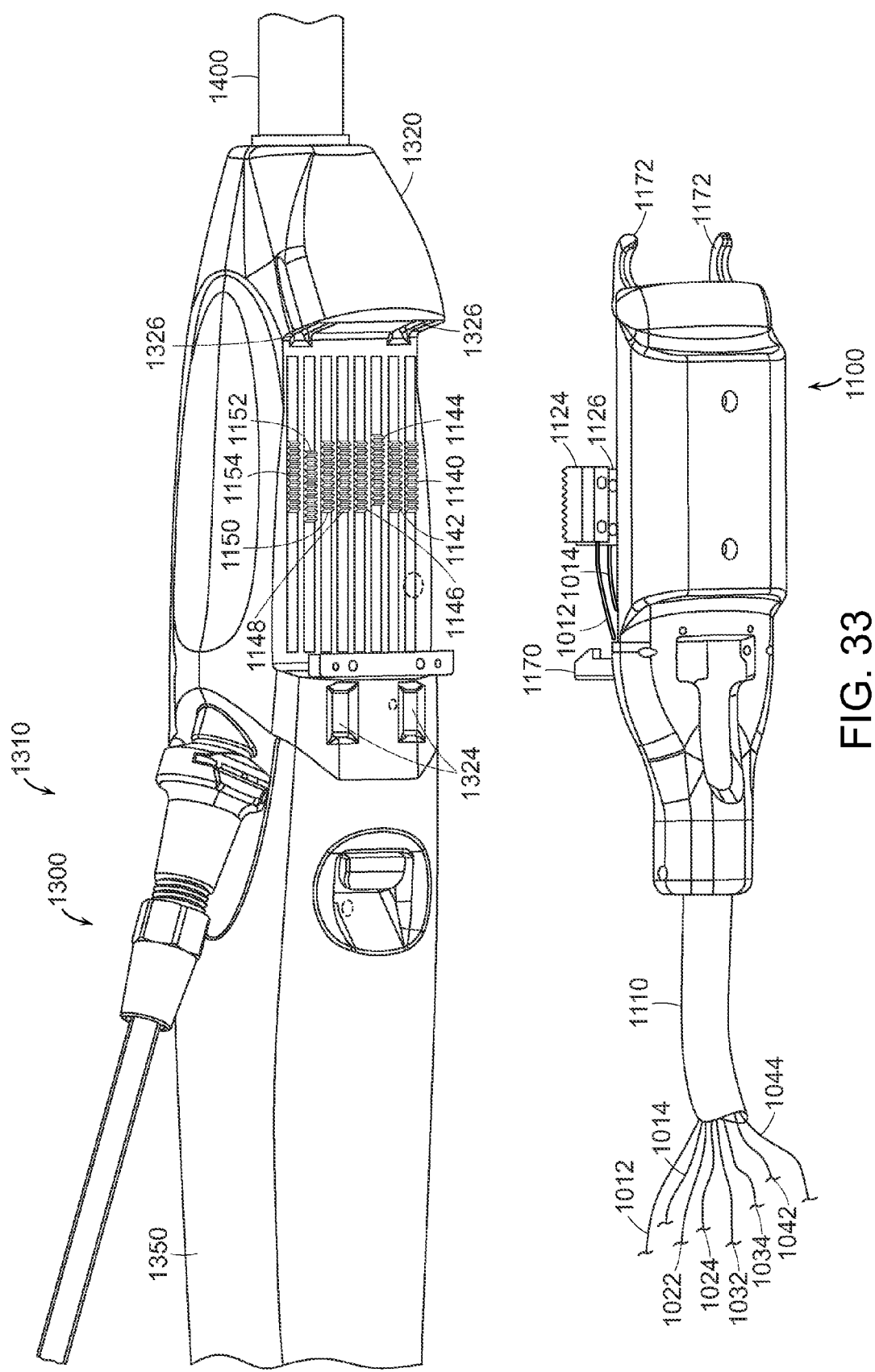
FIG. 33 is a bottom perspective view of a cable docking station embodiment of the present invention and a steerable guide tube assembly of the present invention.

The steerable guide tube assembly 1300 may include a handle housing 1310 that may comprise a distal portion 1320 and a proximal portion 1350 that may be attached together by, for example, snap features 1322 on the distal portion 1320. As can be seen in FIG. 33, the distal housing portion 1320 may be formed with latch cavities 1324, 1326 that are adapted to be retainingly engaged by latch features 1170, 1172, respectively, that are operably attached to or otherwise formed on the bottom plate 1120 of the cable docking station 1100.

The steerable guide tube assembly 1300 may include a flexible insertion tube 1400 that operably supports two or more steerable working channels 1410 and 1420. For example, when the handle housing 1310 is docked to the cable docking station 1100, the distal end portion 1412 of the left working channel 1410 may be steered by manipulating cables 1012, 1014, 1022 and 1024 and the distal end portion 1142 of the working channel 1140 may be steered by cables 1032, 1034, 1042, 1044 as will be explained in further detail below. In particular, in various embodiments, the upper pitch racks 1140, 1142, 1144, 1146, 1148, 1150, 1152, 1154 each have a distal cable segment attached thereto that extend through corresponding coil pipe segments supported in the flexible insertion tube 1400 to be coupled to the distal end portions 1412, 1422 of the steerable working channels 1410, 1420, respectively. See FIG. 35.

Referring to FIGS. 33 and 34, the upper pitch rack 1140 may be attached to a proximal end of a distal cable segment 1160 that extends through a coil pipe segment 1162 to be attached to the distal end portion 1412. The upper pitch rack 1142 may be attached to a proximal end of a distal cable segment 1164 that extends through a coil pipe segment 1166 to be attached to the distal end portion 1412. The upper pitch rack 1144 may be attached to a proximal end of a distal cable segment 1168 that extends through a coil pipe segment 1170 to be attached to the distal end portion 1412. The upper pitch rack 1146 may be attached to a proximal end of a distal cable segment 1172 that extends through a coil pipe segment 1174 to be attached to the distal end portion 1412.

Similarly, the upper pitch rack 1148 may be attached to a proximal end of a distal cable segment 1176 that extends through a coil pipe segment 1178 to be attached to the distal end portion 1422. The upper pitch rack 1150 may be attached to a proximal end of a distal cable segment 1180 that extends through a coil pipe segment 1182 to be attached to the distal end portion 1422. The upper pitch rack 1152 may be attached to a proximal end of a distal cable segment 1184 that extends through a coil pipe segment 1186 to be attached to the distal end portion 1422. The upper pitch rack 1154 may be attached to a proximal end of a distal cable segment 1188 that extends through a coil pipe segment 1190 to be attached to the distal end portion 1422.

Thus, the flexible user interface support assembly 710 may be used as follows. Initially, the clinician may mount the endoscopic surgical instruments 20, 20' to the corresponding tool mounting plate 612. As indicated above, the endoscopic surgical instruments 20, 20' may comprise, for example endoscopes, lights, insufflation devices, cleaning devices, suction devices, hole-forming devices, imaging devices, cameras, graspers, clip appliers, loops, Radio Frequency (RF) ablation devices, harmonic ablation devices, scissors, knives, suturing devices, etc., a portion of which may operably extend through one of the working channels 1410, 1420 in the steerable guide tube assembly 1300. The steerable guide tube assembly 1300 may be "dockingly engaged with" the cable docking station 1100 by engaging the latches 1170, 1172 on the cable docking station 1100 with the respective latch cavities 1324, 1326 in the distal housing section 1320. Those of ordinary skill in the art will understand that the tool mounting plates 612 may be especially configured to mountingly interface with the type of endoscopic surgical instruments to be used. Once the endoscopic surgical instruments 20, 20' are mounted to the user interface support assembly 710 and the steerable guide tube assembly 1300 has been docked on the cable docking station 1100, the flexible working portions 22, 22' of the endoscopic surgical instruments 20, 20' may be inserted through ports in the handle housing 1310 of the steerable guide tube assembly 1300 and out through the working channels 1410, 1420. The insertion tube portion 1400 may then be inserted into the patient, if it had not been previously inserted therein prior to installing the endoscopic surgical instruments 20, 20'.

When the steerable guide tube assembly 1300 has been docked onto the cable docking station 1100, cables 1012, 1014, 1022, 1024 are coupled to their corresponding distal cable segments 1160, 1164, 1168, 1172 by virtue of the meshing engagement between the lower pitch racks 1124, 1126, 1128, 1130 with the respective corresponding upper pitch racks 1140, 1142, 1144, 1146. Similarly, cables 1032, 1034, 1042, and 1044 are coupled to their corresponding distal cable segments 1176, 1180, 1184, and 1188 by virtue of the meshing engagement between the lower pitch racks 1132, 1134, 1136, and 1138 with respective corresponding upper pitch racks 1148, 1150, 1152, and 1154. To manipulate the distal end portion 1412 of the working channel 1410 and thus the working portion 22 of the endoscopic tool 20 in the left and right direction, the clinician simply moves the endoscopic surgical instrument 20 in the direction in which he or she desires the end portion 1412 of the to flexible working channel 1410 to go and the coupled cables 1012, 1014, 1022, 1024, 1160, 1164, 1168, 1172 manipulate the distal end portion 1422 of the working channel 1420.

In various applications, the working channels may communicate with insufflation pressure in the abdomen. To maintain the desired pressure, commercially available seals 28, 28' to prevent the insufflation pressure from leaking out through the flexible working portions 22, 22'. See FIG. 30. Seals 28, 28', such as those manufactured by Ethicon-Endo Surgery, Inc. of Cincinnati, Ohio are couplable to the distal ends of the surgical instruments 20, 20' and facilitate insertion of the operating cable or flexible portion 24, 24' therethrough while maintaining an airtight seal with the outer sheath 27, 27' of the corresponding flexible working portion 22, 22'.

Figure 36:
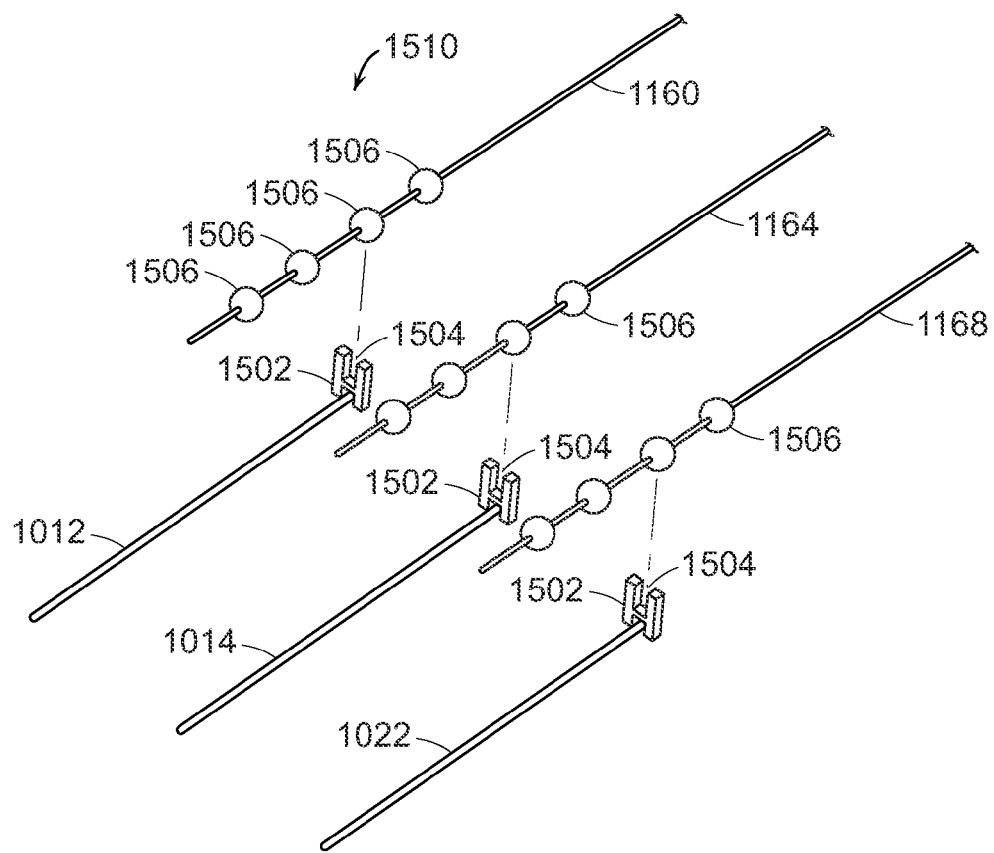
FIG. 36 is a portion of an alternative cable coupling arrangement of the present invention.
Figure 37:
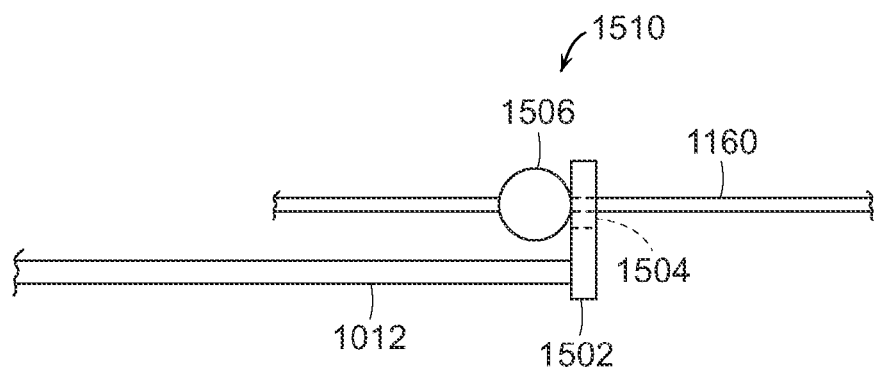
FIG. 37 is a side elevation of one cable coupling arrangement of FIG. 36.

FIGS. 36 and 37 illustrate alternative cable coupling arrangement 1510 that may be effectively employed in the cable docking station 1100. For example, in this embodiment, the distal ends of cables 1012, 1014, 1022, 1024, 1032, 1034, 1042, 1044 would each have a proximal cable coupler in the form of a retention member 1502 attached thereto. Each retention member 1502 would have a groove 1504 therein sized to snappingly receive the proximal end of a corresponding distal cable segment 1160, 1164, 1168, 1172, 1176, 1180, 1184, 1188 therein. Each distal end of distal cable segments 1160, 1164, 1168, 1172, 1176, 1180, 1184, 1188 would have a distal cable coupler attached thereto in the form of at least one retention bead 1506 such that when the cable docking station 1100 is attached to the steerable guide tube assembly 1300, the cable segments cable segments 1160, 1164, 1168, 1172, 1176, 1180, 1184, 1188 snap into the groove 1504 in the corresponding retention member 1502 attached to cables 1012, 1014, 1022, 1024, 1032, 1034, 1042, 1044 and the retention beads 1506 would prevent the cable segments 1160, 1164, 1168, 1172, 1176, 1180, 1184, 1188 from sliding relative to the cables 1012, 1014, 1022, 1024, 1032, 1034, 1042, 1044 as pulling and pushing motions are applied thereto in the manners described above.

Figure 38:
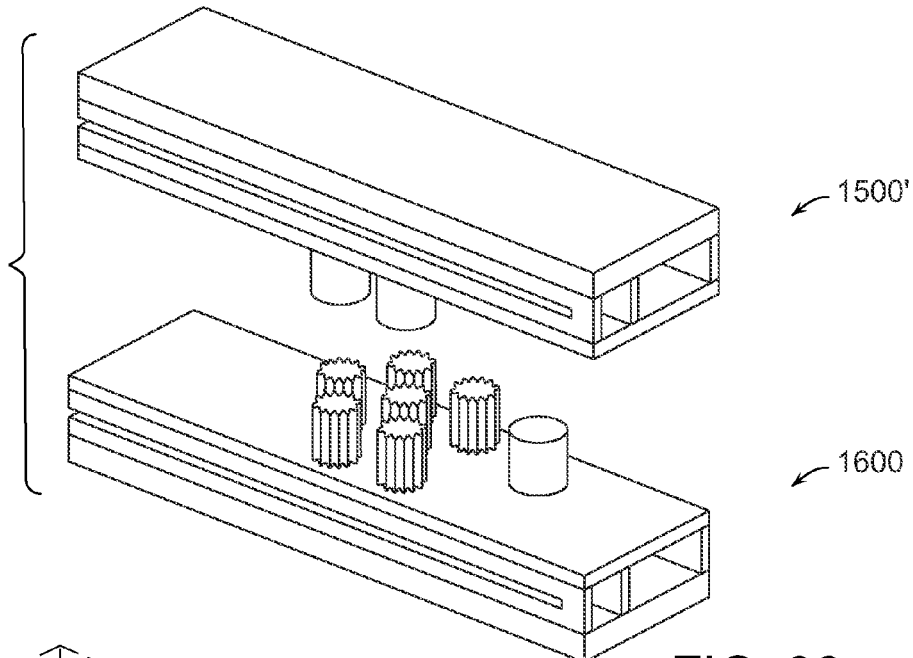
FIG. 38 is a partial exploded perspective view of another cable coupling arrangement of the present invention.
Figure 39:
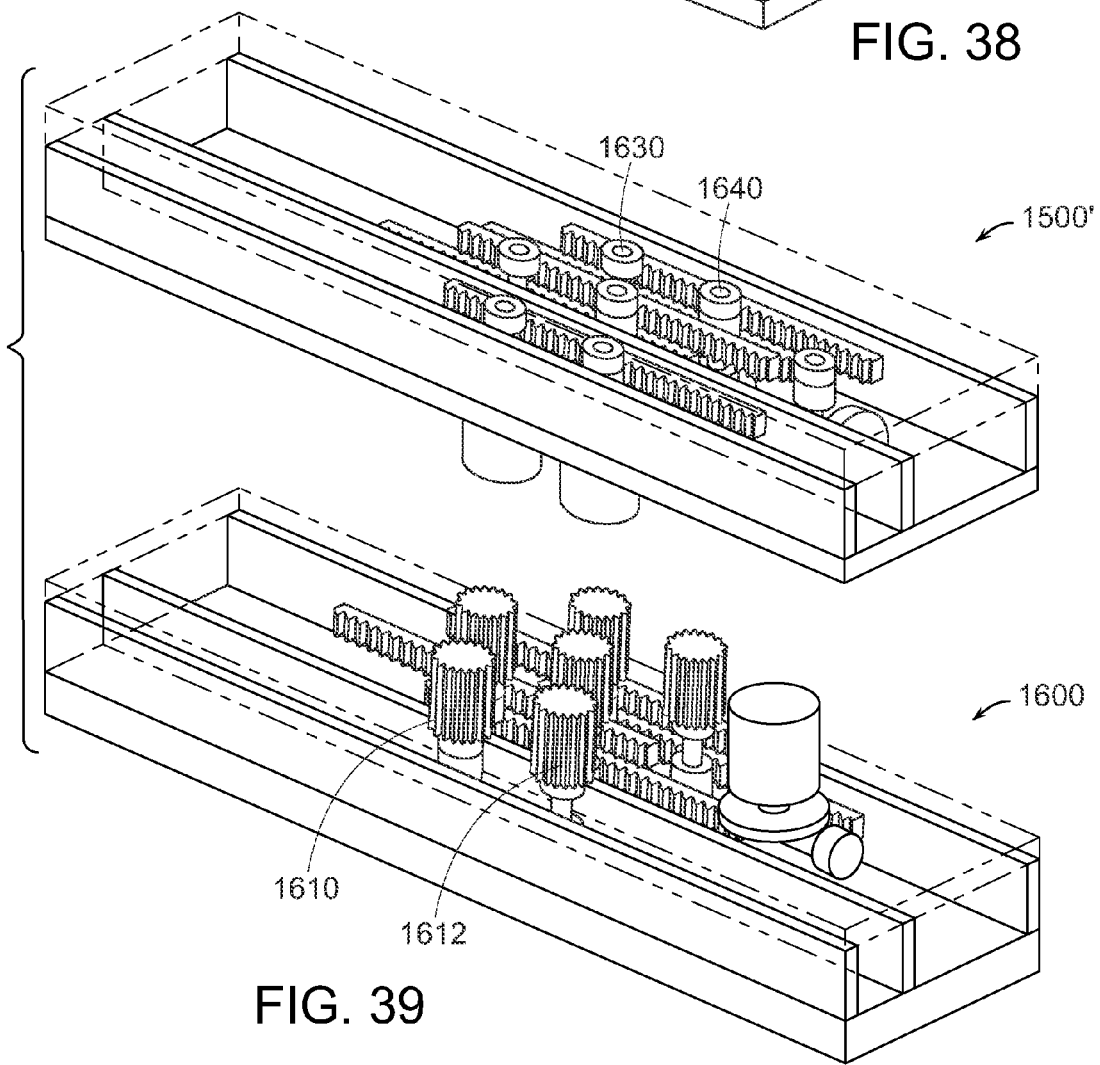
FIG. 39 is another partial perspective view of the cable coupling arrangement of FIG. 38 with the housing portions thereof shown in transparent form to illustrate the positions of the internal components.
Figure 40:
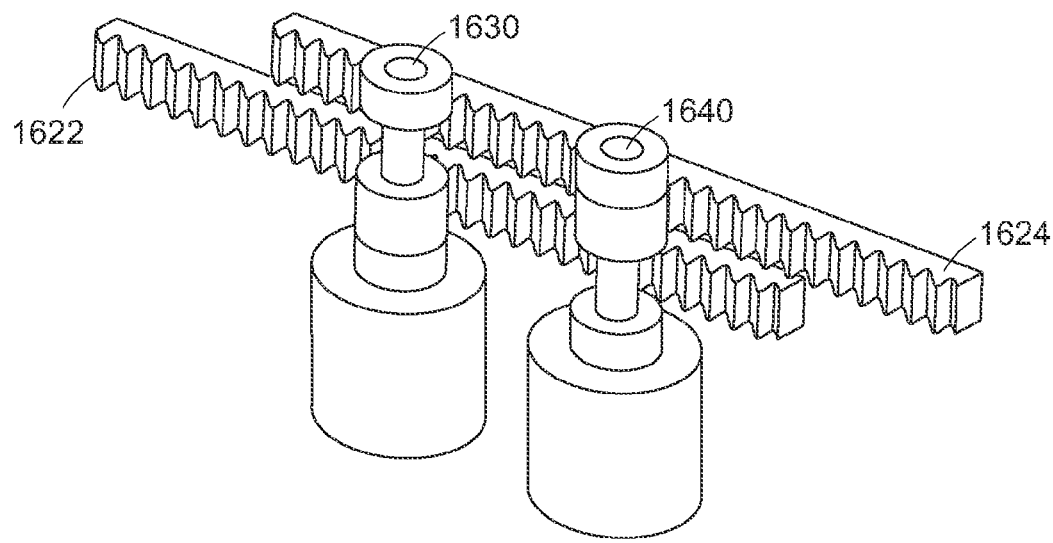
FIG. 40 is a perspective view of some of the upper and lower rack arrangements of the cable coupling arrangement of FIGS. 38 and 39.
Figure 40:
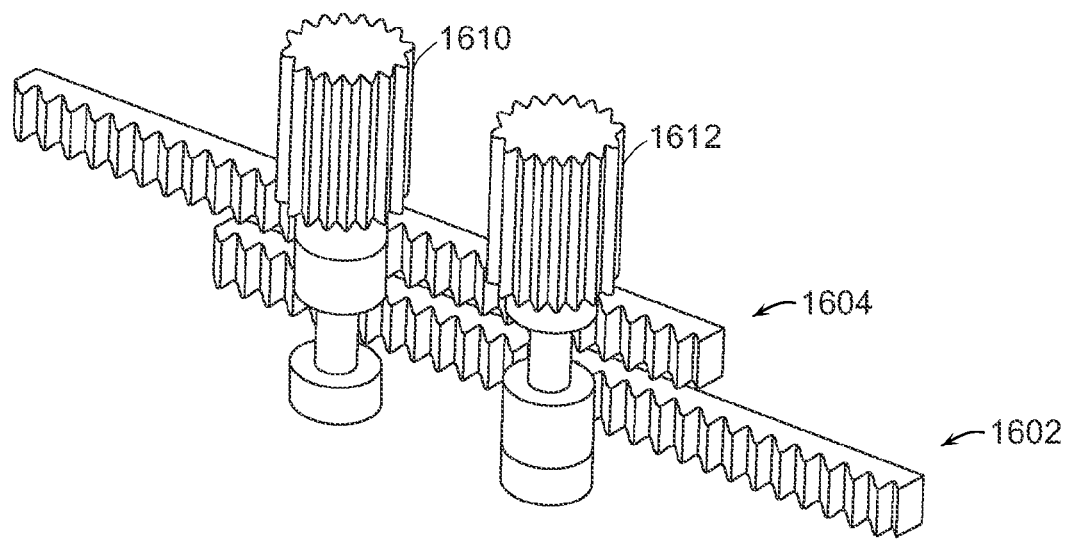

FIGS. 38-40 illustrate alternative cable coupling arrangement 1500' that may be effectively employed in the cable docking station 1100 without the use of the various pitch racks described above. For example, in this embodiment, the docking station 1100 would include a lower gear housing 1600 that slidably supports a series of first lower gear racks 1602. Each first lower gear rack 1602 held in slidable registration with a second lower gear rack 1604. Although not shown, the distal end of each cable 1012, 1014, 1022, 1024, 1032, 1034, 1042, and 1044 is attached to a corresponding lower gear rack 1604. A pair of pinion gear assemblies 1610, 1612 correspond to each pair of first and second lower gear racks 1602, 1604. Similarly the steerable guide tube assembly 1300 would have an upper gear housing 1620 therein that slidably supports a series of first upper gear racks 1622 and second upper gear racks 1624. The first and second upper gear racks 1622, 1624 interface with a corresponding pair of pinion gear assemblies 1630, 1640 that are adapted to meshingly engage with the pinion gear assemblies 1610, 1612 when the steerable guide tube assembly 1300 is docked onto the cable docking station 1100 in the manner described above.

Figure 41:
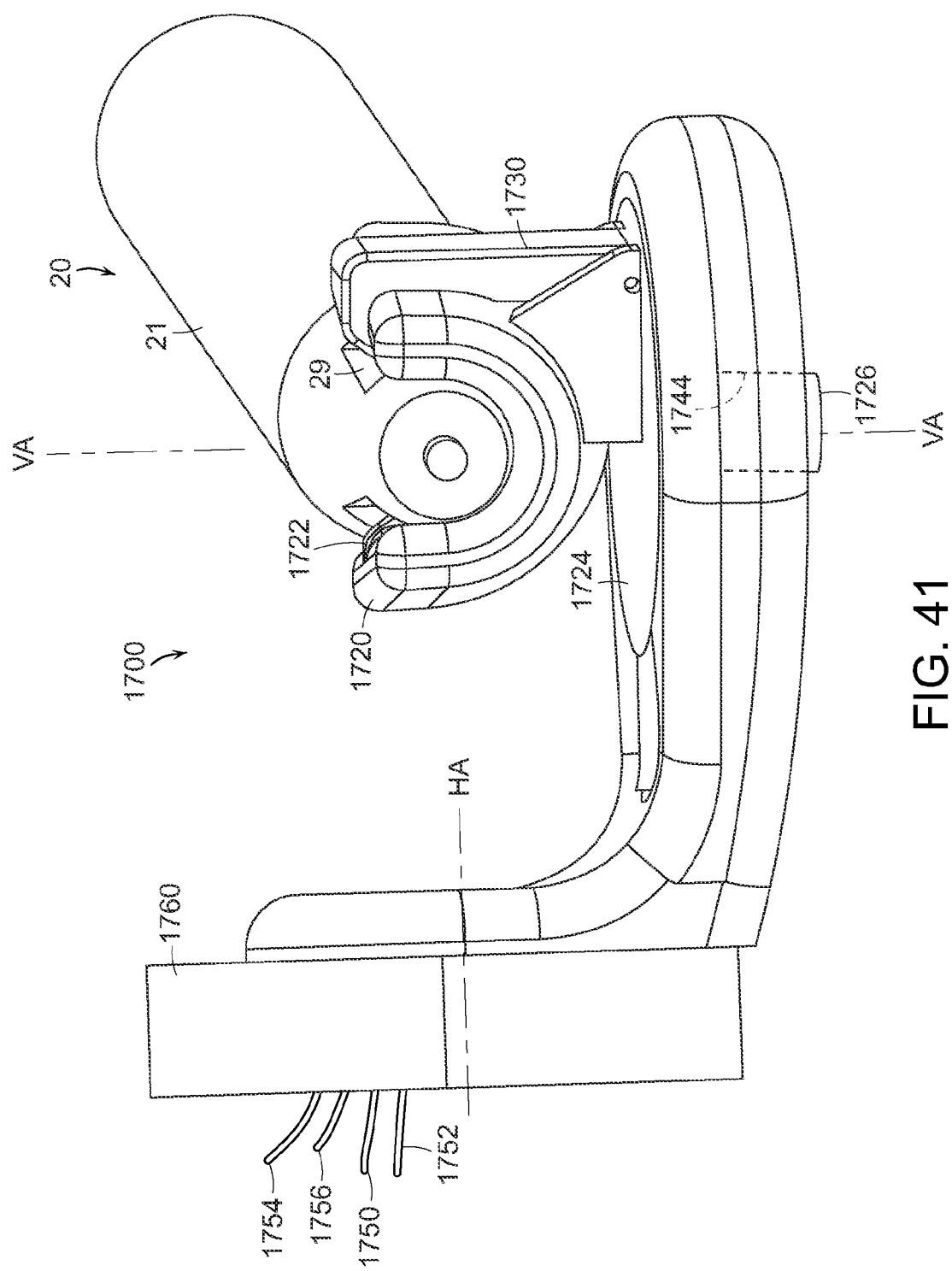
FIG. 41 is a front perspective view of another flexible user interface assembly embodiment of the present invention supporting a portion of an endoscopic surgical instrument.
Figure 42:
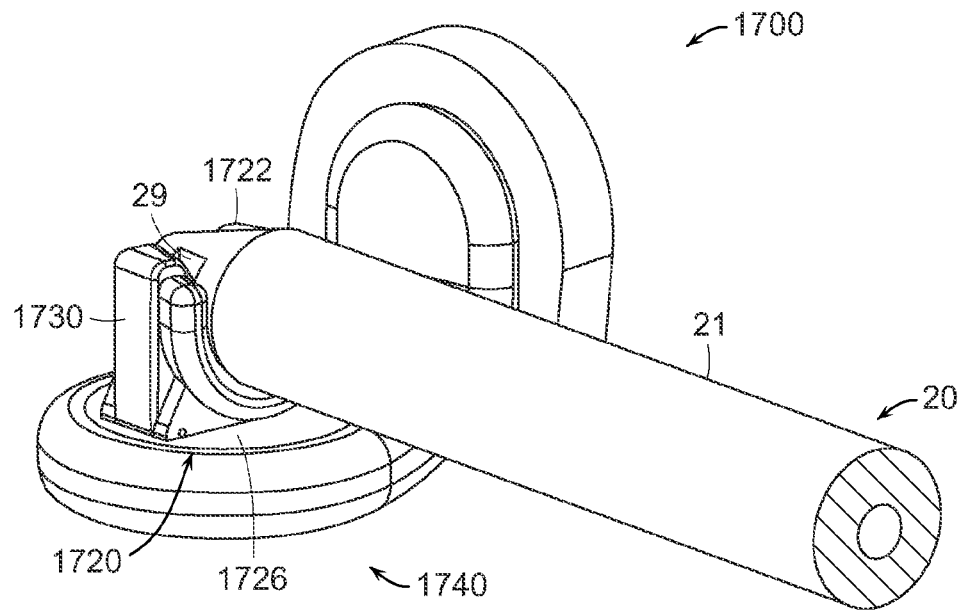
FIG. 42 is a rear perspective view of the flexible user interface assembly embodiment of FIG. 41.
Figure 43:
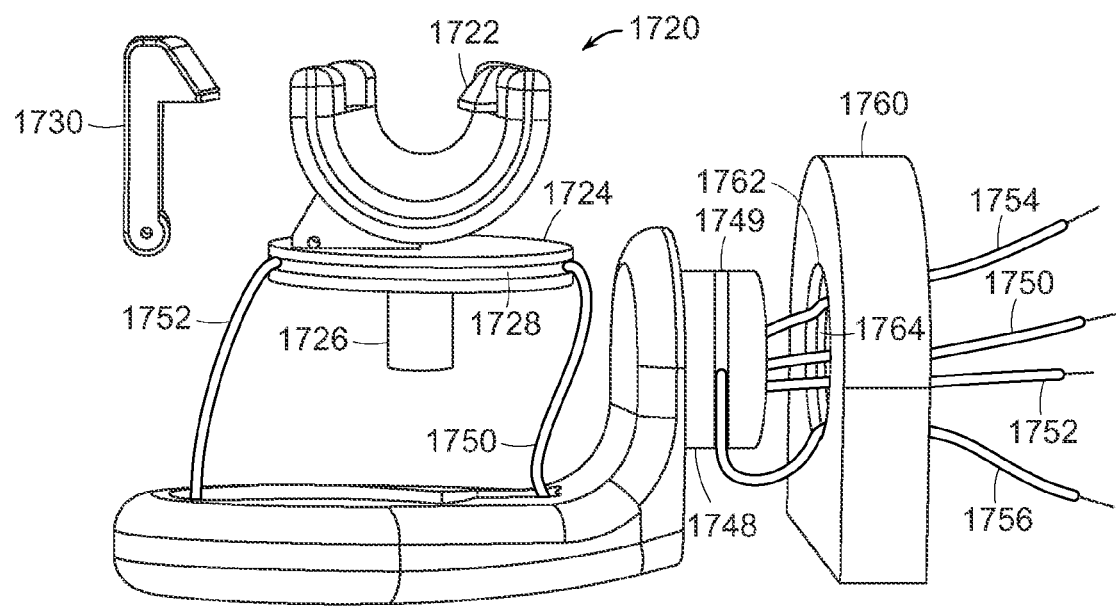
FIG. 43 is an exploded assembly view of the flexible user interface assembly embodiment of FIGS. 41 and 42.
Figure 44:
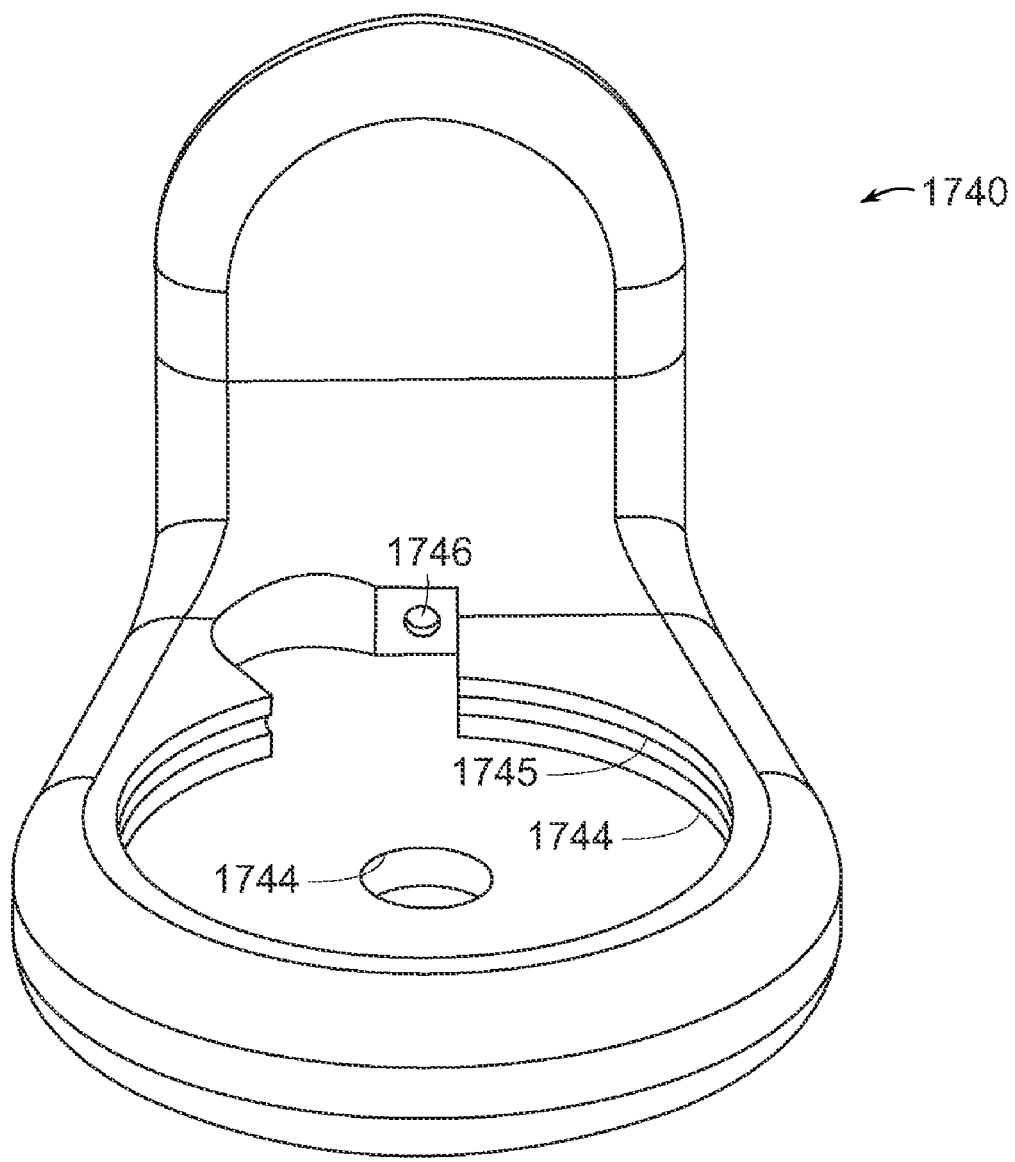
FIG. 44 is a perspective view of a second base embodiment of the flexible user interface assembly of FIGS. 41-43.
Figure 45:
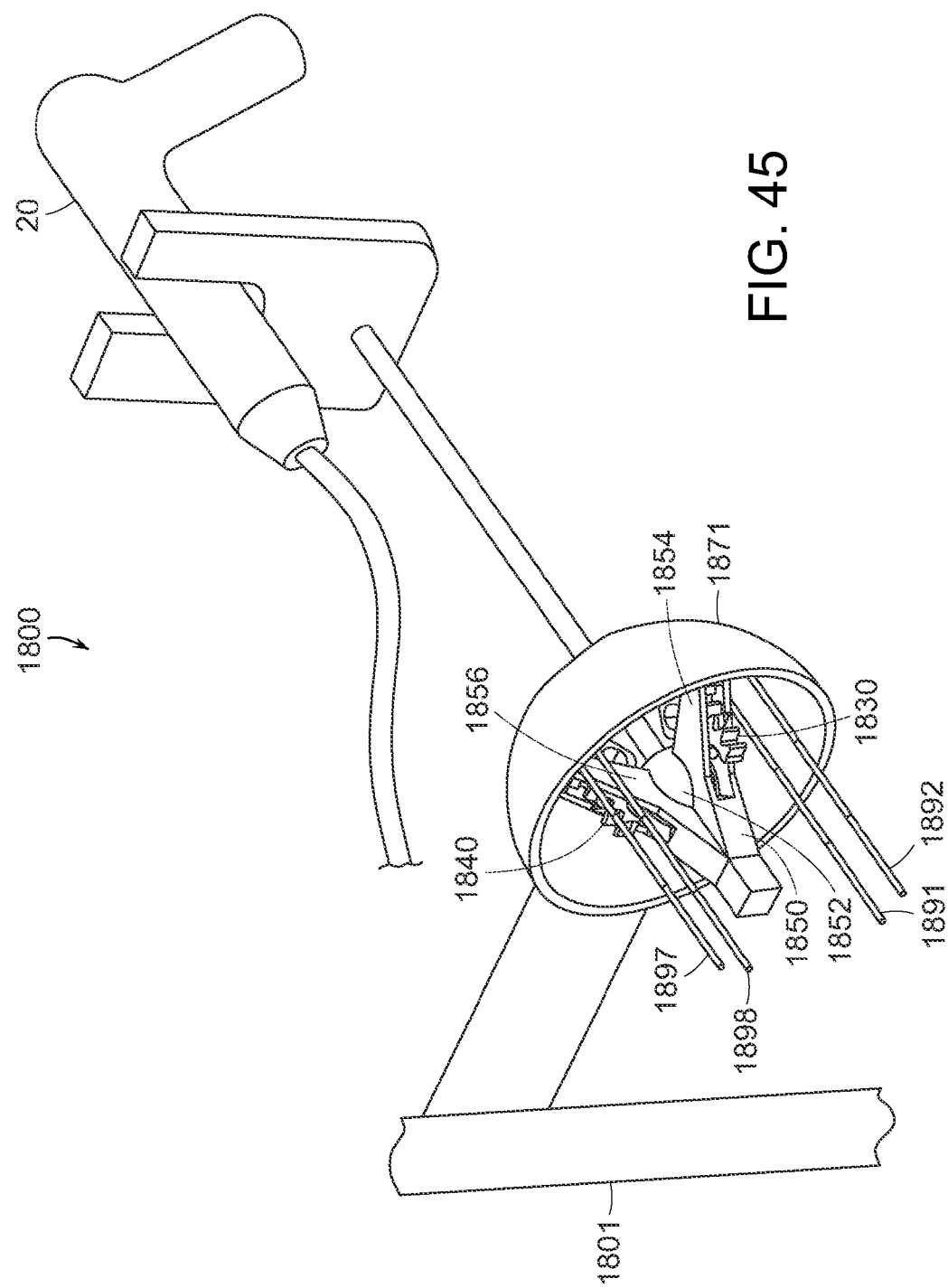
FIG. 45 is a perspective view of a portion of another flexible user interface assembly embodiment of the present invention supporting an endoscopic surgical instrument thereon.
Figure 46:
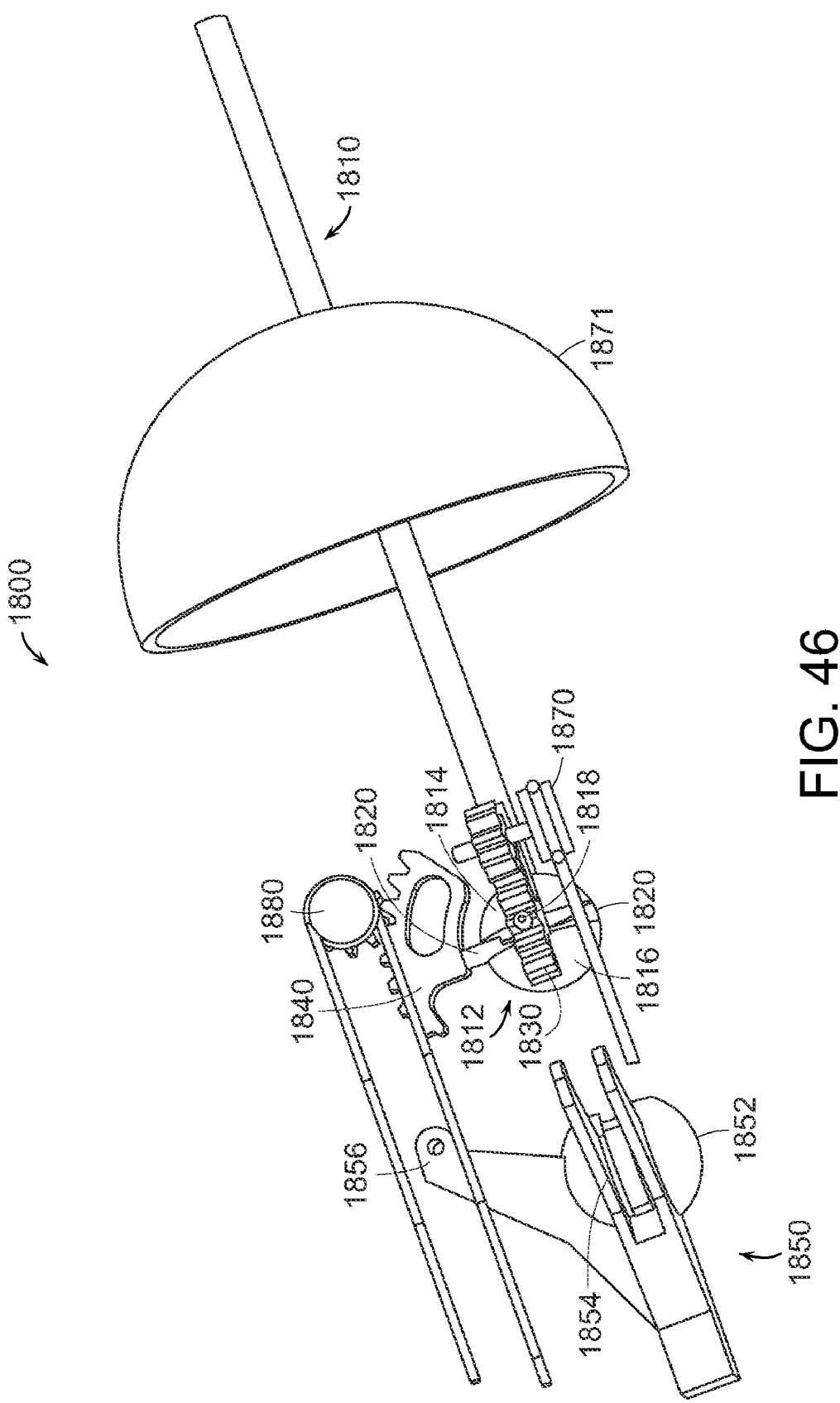
FIG. 46 is a partial exploded assembly view of the flexible user interface assembly of FIG. 45.
Figure 47:
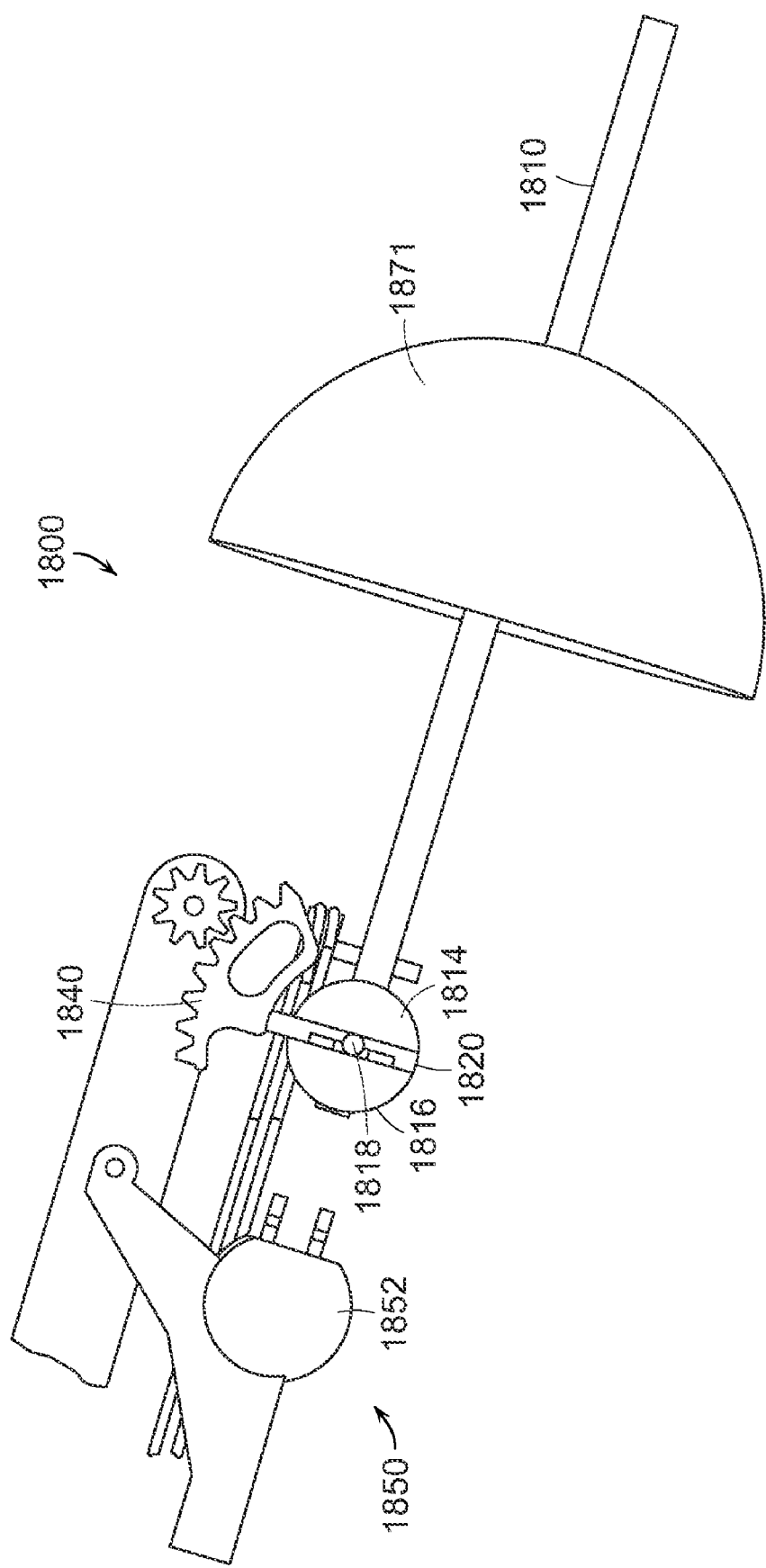
FIG. 47 is another partial exploded assembly view of a portion of the flexible user interface assembly of FIGS. 45 and 46.
Figure 48:
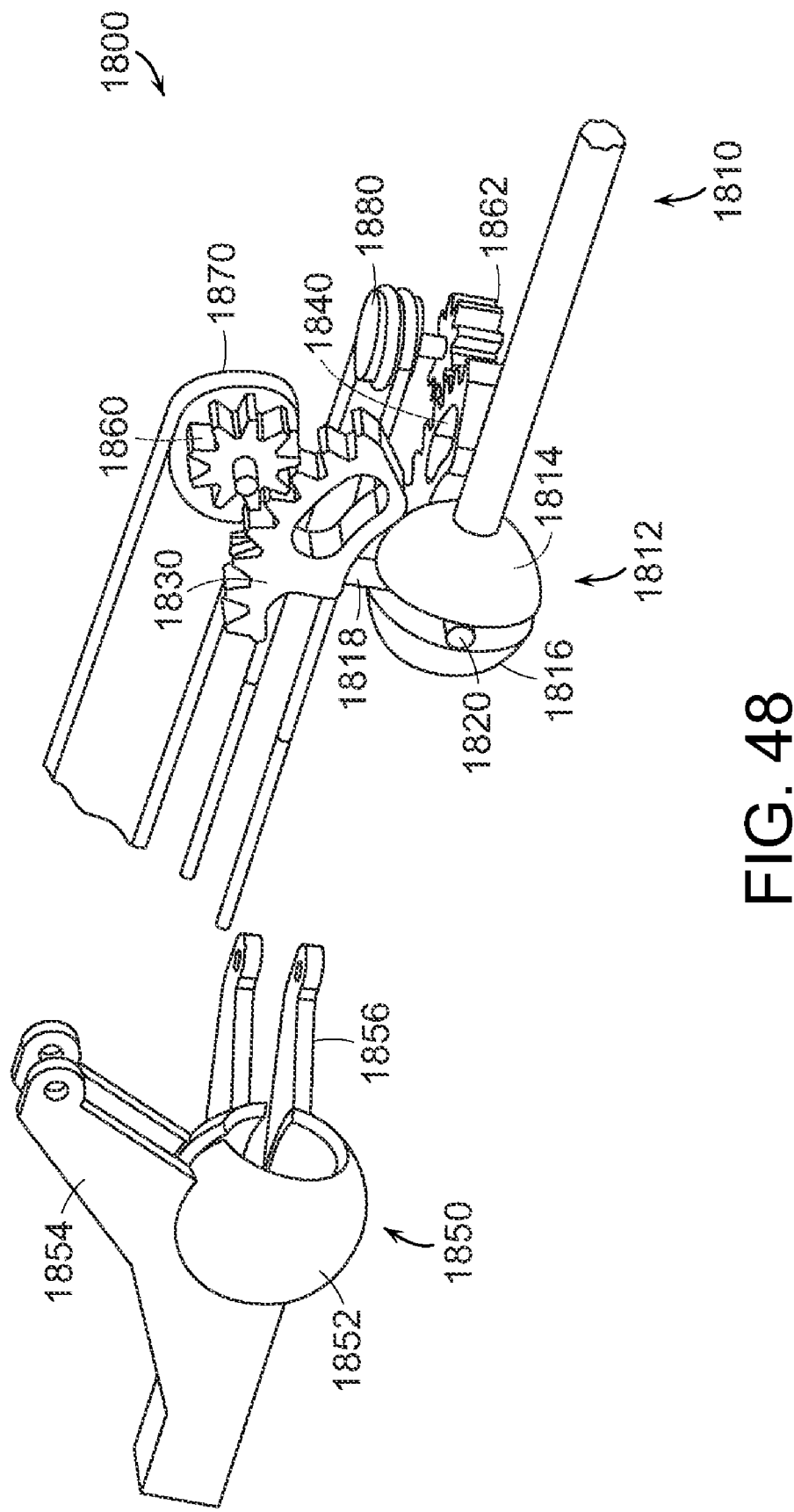
FIG. 48 is another partial exploded assembly view of a portion of the flexible user interface assembly of FIGS. 45-47.

FIGS. 41-44 illustrate another flexible user interface assembly 1700 of the present invention that may be used in connection with an endoscopic surgical instrument 20. In this embodiment, the distal end portion 21 of the endoscopic surgical instrument 20 may be provided with a radial slot segment 29 that is adapted to slidably receive a corresponding retention protrusion 1722 formed on a first rotator 1720. The first rotator 1720 may further include a latch 1730 that is configured to be pivoted into the radial slot segment 29 of the surgical instrument 20 when the distal end portion 21 is mounted to the first rotator 1720 as shown in FIGS. 41 and 42. A spring (not shown) may be employed to retain the latch 1730 in the latched position, yet enable the user to pivot the latch 1730 out of the radial slot segment 29 when it is desired to remove the surgical instrument 20 from the first rotator 1720.

The first rotator 1720 may further have a circular yoke base 1724 that is sized to be received in a circular cavity 1742 in a second base 1740. A lower axle 1726 protrudes from the yoke base 1724 and is sized to be rotatably received in a hole 1744 in the second base 1740 to facilitate pivotal travel of the first rotator 1720 relative to the second base 1740 about a vertical axis VA-VA. The lower axle 1726 may protrude out of the second base 1740 and have a snap ring (not shown) or other fastener arrangement to retain the lower axle 1726 within the hole 1744 while facilitating rotation of the lower axle 1726 therein about the vertical axis VA-VA.

A pair of first steering cables 1750 and 1752 may be attached to the yoke base 1724 and be received in a radially formed groove 1728 in the perimeter of the yoke base 1724 and a mating groove 1745 formed around the perimeter of the cavity 1724 in the second base 1740. The steering cables 1750, 1752 may extend through a passage 1746 in the second base 1740 that further extends through an axle portion 1748 formed thereon. See FIG. 44. Axle portion 1748 is sized to be rotatably received in a hole 1762 in a base portion 1760. Base portion 1760 may comprise a stand, a portion of a bed, a mounting bracket, etc. The axle portion 1748 facilitates rotation of the second base 1740 relative to the base portion 1760 about a horizontal axis HA-HA. A pair of second steering cables 1754, 1756 may be attached to the axle portion 1748 and be received in a radially formed groove 1749 in the perimeter of the axle portion 1748 and a corresponding radial groove 1764 formed in the base portion 1760. See FIG. 43. The flexible user interface assembly 1700 may function as a "two stage gimbal arrangement for applying t control to the steerable cables 1750, 1752, 1754, 1756 attached to a steerable guide tube assembly 1300 of the type described above.

Figure 35:
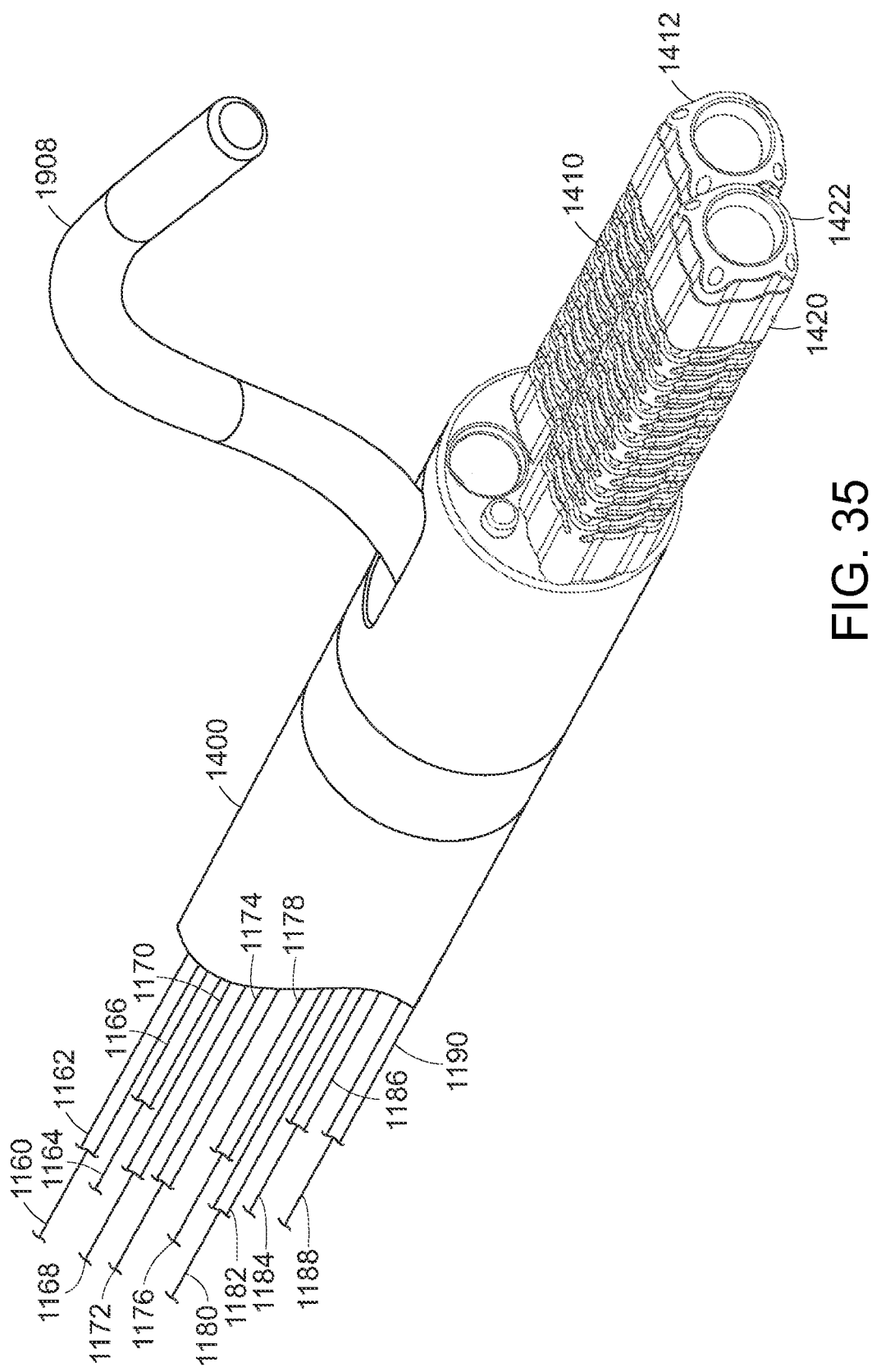
FIG. 35 is a partial perspective view of the distal end of the flexible sheath portion of the steerable guide tube assembly embodiment of the present invention.

FIGS. 44-47 illustrate yet another flexible user interface assembly 1800 of the present invention. This embodiment includes a tool mounting portion or rod 1810 to which an endoscopic surgical instrument 20 may be mounted. In various embodiments, the tool mounting rod 1810 has a ball assembly 1812 formed thereon. The ball assembly 1812 may comprise a first ball segment 1814 and a second ball segment 1816. Constrained between the ball segments 1814 and 1816 is a pair of cross members 1818, 1820 that are pinned together or are otherwise nonmovably fixed to each other. A first arcuate gear segment 1830 is attached to cross member 1816 and a second arcuate gear segment 1840 is attached to the other cross member 1820 at right angles to the first arcuate gear segment 1830. See FIG. 47. The ball assembly 1812 may be movably supported in a socket assembly 1850 that is nonmovably supported or attached to a portion of the housing. FIGS. 34 and 35 illustrate a portion 1871 of the housing that may be attached to a stand, bed, etc, generally depicted as 1801 in FIG. 33.

As can be seen in FIGS. 34 and 35, the socket assembly 1850 includes a ball portion 1852 that is configured to receive the ball assembly 1812 therein. The socket assembly 1812 may further include a first set of pinion support arms 1854 for supporting a first pinion gear 1860 thereon in meshing engagement with the first arcuate gear segment 1830 and a second set of pinion arms 1856 for supporting a second pinion gear 1862 in meshing engagement with the second arcuate gear segment 1840. When assembled, the first pinion gear 1860 and the second pinion gear 1862 are positioned at right angles to each other. In various embodiments a first pulley 1870 is attached to the first pinion gear 1860 for rotation therewith a second pulley 1880 is attached to the second pinion gear 1862 for rotation therewith. Thus, rotation of the ball assembly 1812 along a first plane defined by the first arcuate gear segment 1830 will result in the rotation of the first pinion gear 1860 and rotation of the ball assembly 1812 in a second plane that is orthogonal to the first plane will result in the rotation of the second pinion gear 1862.

In various embodiments, a first cable 1890 is sheaved around the first pulley such that ends 1891 and 1892 of the cable 1890 may be operably coupled to corresponding cable segments of a steerable guide tube assembly 1300 in any of the various manners described above or otherwise used to control a steerable guide tube. For example, as the first pulley is rotated in a first direction, end 1891 may get pulled in the first direction wherein end 1892 is pushed in an opposite direction. Similarly, a second cable 1896 is sheaved around the second pulley such that ends 1897 and 1898 may be operably coupled to corresponding cable segments of a steerable guide tube assembly 1300 in any of the various manners described above or otherwise used to control a steerable guide tube assembly. As the second pulley is rotated in another first direction, end 1897 may get pulled in that another first direction and end 1898 may get pushed in the opposite direction. As such, after the ends 1891, 1892 of the first cable 1890 and the ends 1897, 1898 of the second cable have been coupled to the cable segment used to control a steerable guide tube, movement of the surgical instrument 20 along a first plane may result in the manipulation of the distal end of the guide tube, for example, in up and down directions. In addition, manipulation of the surgical instrument 20 in a second plane that is orthogonal to the first plane may result in the manipulation of the distal end of the steerable guide tube in, for example, left and right directions.

Those of ordinary skill in the art will readily appreciate that the flexible user interface support assembly embodiments of the present invention translates laparoscopic-like manipulation to linear pull-push motion. The push-pull motion enables the use of cables to generate tool-tip articulation at the end of the steerable guide tube assembly, thereby providing the clinician with a familiar laparoscopic-like user experience during the surgical procedure. Furthermore, the flexible user interface embodiments described immediately above facilitates the translation of the tool/instrument articulation motions into rotary motions. The rotary motion is then translated through the drive shafts into the pulleys. The pulleys serve to translate the rotary motion to linear translation of the cables. The cables translate along the gooseneck inside coil pipe to allow the dynamic location of the steerable guide tube assembly. In addition, the unique and novel cable docking station embodiments enables the quick coupling of a cable-controlled interface with a cable-controlled guide tube assembly, without cables hanging out of the devices to become inadvertently tangled and possibly damaged.

Those of ordinary skill in the art will appreciate that the unique and novel aspects of the various embodiments of the flexible interface support assemblies of the present invention provide the clinician with the ability to control the articulation of a working channel into which a portion of a surgical instrument has been inserted, simply by manipulating the surgical instrument relative to a fixed position. In particular, various embodiments of the present invention provide separate control of right and left working channel horizontal articulation and separate control of right and left working channel up/down articulation. While the embodiment depicted in FIGS. 1-6 above is adapted for use with two separate surgical tools or instruments, other embodiments could be constructed to support a single surgical tool, while still other could be adapted to support more than two surgical tools. The use of the friction hinges enables the clinician to pivot the tools about a corresponding fixed vertical axis and retain the tool in that position when the clinician releases the tool. The unique and novel means for connecting the cables from the steerable guide tube assembly 200 to the mounting assembly facilitate quick and easy attachment employment of the flexible interface systems with a variety of different cable driven guide tube assemblies. The mobile nature of the stand and the flexible gooseneck arrangement enables the system to be advantageously located and positioned within the surgical suite.

While the embodiments have been described, it should be apparent, however, that various modifications, alterations and adaptations to the embodiments may occur to persons skilled in the art with the attainment of some or all of the advantages of the invention. For example, according to various embodiments, a single component may be replaced by multiple components, and multiple components may be replaced by a single component, to perform a given function or functions. This application is therefore intended to cover all such modifications, alterations and adaptations without departing from the scope and spirit of the disclosed invention as defined by the appended claims.

The devices disclosed herein can be designed to be disposed of after a single use, or they can be designed to be used multiple times. In either case, however, the device can be reconditioned for reuse after at least one use. Reconditioning can include a combination of the steps of disassembly of the device, followed by cleaning or replacement of particular pieces, and subsequent reassembly. In particular, the device can be disassembled, and any number of particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those of ordinary skill in the art will appreciate that the reconditioning of a device can utilize a variety of different techniques for disassembly, cleaning/replacement, and reassembly. Use of such techniques, and the resulting reconditioned device, are all within the scope of the present application.

Preferably, the invention described herein will be processed before surgery. First a new or used instrument is obtained and, if necessary, cleaned. The instrument can then be sterilized. In one sterilization technique, the instrument is placed in a closed and sealed container, such as a plastic or TYVEK® bag. The container and instrument are then placed in a field of radiation that can penetrate the container, such as gamma radiation, x-rays, or higher energy electrons. The radiation kills bacteria on the instrument and in the container. The sterilized instrument can then be stored in the sterile container. The sealed container keeps the instrument sterile until it is opened in the medical facility.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. An interface system for aiding clinicians in controlling and manipulating at least one endoscopic surgical instrument and a cable-controlled guide tube system, said interface system comprising:
   a tool docking assembly supportable relative to the cable-controlled guide system, said tool docking assembly comprising:
      a first tool docking station for retainingly supporting one of the at least one endoscopic surgical instruments for selective pivotal travel about a first axis upon application of a first pivotal motion thereto and about a second axis upon application of a second pivotal motion thereto;
      a first cable attachment assembly configured to couple a first cable from the cable controlled guide tube system to said first tool docking station;
      at least one friction brake assembly interacting with said first tool docking station for retaining said first tool docking station in a desired position upon discontinuing application of at least one of said first and second pivotal motions to said first tool docking station;
      a second tool docking station for retainingly supporting another one of the at least one endoscopic surgical instruments for selective pivotal travel about a third axis upon application of a third pivotal motion thereto and about a fourth axis upon application of a fourth pivotal motion thereto;
      a third cable attachment assembly configured to couple another cable from the cable-controlled guide tube system to said second tool docking station; and
      at least one other friction brake assembly interacting with said second tool docking station for retaining said second tool docking station in another desired position upon discontinuing application of at least one of said third and fourth pivotal motions to said second tool docking station.

2. The interface system of claim 1 further comprising a second cable attachment assembly configured to couple a second cable from the cable-controlled guide tube system to said first tool docking station.

3. The interface system of claim 1 wherein said tool docking assembly and the cable-controlled guide tube assembly are mounted on a common stand.

4. The interface system of claim 3 wherein said common stand mounts to the surgical table and includes height adjustment means.

5. The interface system of claim 3 wherein said common stand includes a lockable wheels and a height adjustment means.

6. The interface system of claim 1 wherein said tool docking assembly comprises:
   a central cross bar assembly; and
   a first tool mounting bracket selectively pivotable relative to said central cross-bar about a first axis and wherein said first tool mounting station comprises:
   a first tool docking plate pivotally attached to said first tool mounting bracket for selective pivotal travel about said second axis relative to said first tool mounting bracket.

7. The interface system of claim 6 wherein said first tool mounting bracket is pivotally mounted to said central cross bar assembly by a first pivot bar that defines said first axis and wherein said at least one said friction brake assembly comprises a first set screw that has a rounded end portion extending through said first tool mounting bracket to selectively frictionally contact a portion of said pivot bar to selectively apply a first amount of friction thereto.

8. The interface system of claim 7 wherein said at least one friction brake assembly comprises another friction brake assembly defining said second axis and coupling said first docking plate to said first tool mounting bracket.

9. The interface system of claim 8 wherein said another friction brake assembly comprises a first friction hinge.

10. The interface system of claim 7 wherein said rounded portion of said setscrew is received in a groove in said first pivot bar.

11. The interface system of claim 6 wherein said a tool docking assembly further comprises:
   a second tool mounting bracket spaced from said first tool mounting bracket and being selectively pivotable relative to said central cross-bar about a third axis upon application of a third pivotal motion thereto and wherein said second tool mounting station comprises:
   a second tool docking plate pivotally attached to said second tool mounting bracket for selective pivotal travel about a fourth axis relative to said second tool mounting bracket upon application of a fourth pivotal motion thereto.

12. An interface system for aiding clinicians in controlling and manipulating at least one endoscopic surgical instrument and a cable-controlled guide tube system, said interface system comprising:
   a central bar having a first end portion and a second end portion spaced from said first end portion;
   a first tool docking station movably coupled to said first end portion of said central bar for selective pivotal travel relative to said central bar about a first axis upon application of a first pivotal motion thereto and a second axis upon application of a second pivotal motion thereto, said first tool docking station configured to operably support one of the at least one endoscopic surgical instruments therein;
   a first friction brake assembly interacting with said first tool docking station for retaining said first tool docking station in a desired position about said first axis upon discontinuing application of said first pivotal motion to said first tool docking station;
   a second friction brake assembly interacting with said first tool docking station for retaining said first tool docking station in a desired position about said second axis upon discontinuing application of said second pivotal motion to said first tool docking station;
   a first cable attachment assembly configured to couple a first cable from the cable-controlled guide tube system to said first tool docking station;
   a second cable attachment assembly configured to couple a second cable from the cable-controlled guide tube system to said first tool docking station;
   a second tool docking station movably coupled to said second end portion of said central bar for selective pivotal travel relative to said central bar about a third axis upon application of a third pivot motion thereto and about a fourth axis upon application of a fourth pivotal motion thereto, said second tool docking station configured to operably support another one of the at least one endoscopic surgical instruments therein;
   a third friction brake assembly interacting with said second tool docking station for retaining said second tool docking station in a desired position about said third axis upon discontinuing application of said third pivotal motion to said second tool docking station;
   a fourth friction brake assembly interacting with said second tool docking station for retaining said second tool docking station in a desired position about said fourth axis upon discontinuing application of said fourth pivotal motion to said second tool docking station;
   a third cable attachment assembly configured to couple a third cable from the cable-controlled guide tube system to said second tool docking station; and
   a fourth cable attachment assembly configured to couple a fourth cable from the cable-controlled guide tube system to said second tool docking station.

13. A method for controlling a cable-controlled guide tube system, comprising:
   movably mounting a surgical instrument having a first elongated flexible portion to a first tool docking station positioned relative to the cable-controlled guide tube system;
   inserting the first elongated flexible portion through a first steerable working channel in the cable-controlled guide tube system;
   affixing a first cable attached to the first steerable working channel to said first tool docking station;
   affixing a second cable attached to the first steerable working channel to said first tool docking station; and
   moving the first tool docking station in a first direction to apply a first actuation motion to said first cable.

14. The method of claim 13 further comprising moving the first tool docking station in a second direction to apply a second actuation motion to said first cable.

15. The method of claim 14 wherein said second direction is opposite from said first direction.

16. The method of claim 14 further comprising moving the first tool docking station in a third direction to apply a third actuation motion to said second cable.

17. The method of claim 16 further comprising moving the first tool docking station in a fourth direction to apply a fourth actuation motion to said second cable.

18. The method of claim 13 further comprising moving a proximal handle portion of the surgical instrument in a vertical direction such that a tip portion of the first elongated flexible portion moves in another vertical direction that is opposite from said vertical direction.

19. The method of claim 18 further comprising moving the proximal handle portion of the surgical instrument in a horizontal direction such that the tip portion moves in another horizontal direction that is opposite from said horizontal direction.

20. The method of claim 13 further comprising moving a proximal handle portion of the surgical instrument in a vertical direction such that a tip portion of the first elongated flexible portion moves in said vertical direction.

21. The method of claim 20 further comprising moving the proximal handle portion of the surgical instrument in a horizontal direction such that the tip portion moves in said horizontal direction.

22. An interface system for aiding clinicians in controlling and manipulating at least one endoscopic surgical instrument and a cable-controlled guide tube system, said interface system comprising:
 a tool docking assembly supportable relative to the cable-controlled guide system, said tool docking assembly comprising:
  a first tool docking station for retainingly supporting one of the at least one endoscopic surgical instruments for selective pivotal travel about a first axis upon application of a first pivotal motion thereto and about a second axis upon application of a second pivotal motion thereto;
  a first cable attachment assembly configured to couple a first cable from the cable controlled guide tube system to said first tool docking station;
  at least one friction brake assembly interacting with said first tool docking station for retaining said first tool docking station in a desired position upon discontinuing application of at least one of said first and second pivotal motions to said first tool docking station;
 a second cable attachment assembly configured to couple a second cable from the cable-controlled guide tube system to said first tool docking station:
 a second tool docking station for retainingly supporting another one of the at least one endoscopic surgical instruments for selective pivotal travel about a third axis and a fourth axis;
 a third cable attachment assembly configured to couple a third cable from the cable-controlled guide tube system to said second tool docking station; and
 a fourth cable attachment assembly configured to couple a fourth cable from the cable-controlled guide tube system to said second tool docking station.

23. The interface system of claim 22 wherein said tool docking assembly and the cable-controlled guide tube assembly are mounted on a common stand.

24. The interface system of claim 23 wherein said common stand mounts to the surgical table and includes height adjustment means.

25. The interface system of claim 23 wherein said common stand includes a lockable wheels and a height adjustment means.

26. The interface system of claim 22 wherein said second axis is substantially transverse to said first axis and said fourth axis is substantially transverse to said third axis.

27. The interface system of claim 22 wherein said tool docking assembly comprises:
 a central cross bar assembly; and
 a first tool mounting bracket selectively pivotable relative to said central cross-bar about a first axis and wherein said first tool mounting station comprises:
  a first tool docking plate pivotally attached to said first tool mounting bracket for selective pivotal travel about said second axis relative to said first tool mounting bracket.

28. The interface system of claim 27 wherein said first tool mounting bracket is pivotally mounted to said central cross bar assembly by a first pivot bar that defines said first axis and wherein said at least one said friction brake assembly comprises a first set screw that has a rounded end portion extending through said first tool mounting bracket to selectively frictionally contact a portion of said pivot bar to selectively apply a first amount of friction thereto.

29. The interface system of claim 28 wherein said rounded portion of said setscrew is received in a groove in said first pivot bar.

30. The interface system of claim 28 wherein said at least one friction brake assembly comprises another friction brake assembly defining said second axis and coupling said first docking plate to said first tool mounting bracket.

31. The interface system of claim 30 wherein said another friction brake assembly comprises a first friction hinge.

32. The interface system of claim 27 wherein said a tool docking assembly further comprises:
 a second tool mounting bracket spaced from said first tool mounting bracket and being selectively pivotable relative to said central cross-bar about a third axis upon application of a third pivotal motion thereto and wherein said second tool mounting station comprises:
  a second tool docking plate pivotally attached to said second tool mounting bracket for selective pivotal travel about a fourth axis relative to said second tool mounting bracket upon application of a fourth pivotal motion thereto.

33. An interface system for aiding clinicians in controlling and manipulating at least one endoscopic surgical instrument and a cable-controlled guide tube system, said interface system comprising:
 a tool docking assembly supportable relative to the cable-controlled guide system, said tool docking assembly comprising:
  a first tool docking station for retainingly supporting one of the at least one endoscopic surgical instruments for selective pivotal travel about a first axis upon application of a first pivotal motion thereto and about a second axis upon application of a second pivotal motion thereto;
  a first cable attachment assembly configured to couple a first cable from the cable controlled guide tube system to said first tool docking station;
  at least one friction brake assembly interacting with said first tool docking station for retaining said first tool docking station in a desired position upon discontinuing application of at least one of said first and second pivotal motions to said first tool docking station;
  a central cross bar assembly;
  a first tool mounting bracket selectively pivotable relative to said central cross-bar about the first axis; and
  a first tool docking plate pivotally attached to said first tool mounting bracket for selective pivotal travel about the second axis relative to said first tool mounting bracket.

34. The interface system of claim 33 wherein said first tool mounting bracket is pivotally mounted to said central cross bar assembly by a first pivot bar that defines said first axis and wherein said at least one said friction brake assembly comprises a first set screw that has a rounded end portion extending through said first tool mounting bracket to selectively frictionally contact a portion of said pivot bar to selectively apply a first amount of friction thereto.

35. The interface system of claim 34 wherein said a tool docking assembly further comprises:
- a second tool mounting bracket spaced from said first tool mounting bracket and being selectively pivotable relative to said central cross-bar about a third axis upon application of a third pivotal motion thereto and wherein said second tool mounting station comprises:
- a second tool docking plate pivotally attached to said second tool mounting bracket for selective pivotal travel about a fourth axis relative to said second tool mounting bracket upon application of a fourth pivotal motion thereto.

36. The interface system of claim 34 wherein said rounded portion of said setscrew is received in a groove in said first pivot bar.

37. The interface system of claim 36 wherein said at least one friction brake assembly comprises another friction brake assembly defining said second axis and coupling said first docking plate to said first tool mounting bracket.

38. The interface system of claim 37 wherein said another friction brake assembly comprises a first friction hinge.

* * * * *